United States Patent [19]

Huang

[11] Patent Number: 6,069,231
[45] Date of Patent: May 30, 2000

[54] PR DOMAIN PEPTIDES

[75] Inventor: Shi Huang, San Diego, Calif.

[73] Assignee: La Jolla Cancer Research Foundation, La Jolla, Calif.

[21] Appl. No.: 08/516,859

[22] Filed: Aug. 18, 1995

Related U.S. Application Data

[63] Continuation-in-part of application No. 08/399,411, Mar. 6, 1995, Pat. No. 5,831,008, which is a continuation-in-part of application No. 08/292,683, Aug. 18, 1994, abandoned.

[51] Int. Cl.⁷ ............................. C06K 7/06; C06K 14/435
[52] U.S. Cl. ........................... 530/327; 530/300; 530/350
[58] Field of Search ................................... 530/300, 324, 530/350

[56] References Cited

PUBLICATIONS

George et al. Macromolecular Sequencing & Synthesis Selected Methods & Applications, pp. 127–149, 1988.
Bourne et al., "The GTPase superfamily: conserved structure and molecular mechanism." *Nature,* 349:117–127 (1991).
Boyd et al., "A region in the C–terminus of adenovirus 2/5 E1a protein is required for association with a cellular phosphoprotein and important for the negative modulation of T24–ras mediated transformation, tumorigenesis and metastasis." *EMBO. J.* 12:469–478 (1993).
Van Cherington et al., "Separation of simian virus 40 large T antigen transforming and origin–binding functions from the ability to block differentiation." *Mol. Cell. Biol.,* 8:1380–1384 (1988).
DeCaprio et al., "SV40 large tumor antigen forms a specific complex with the product of the retinoblastoma susceptibility gene." *Cell,* 54:275–283 (1988).
Defeo–Jones et al., "Cloning of cDNAs for cellular proteins that bind to the retinoblastoma gene product." *Nature,* 352:251–254 (1991).
Dowdy et al., "Physical interaction of the retinoblastoma protein with human D cyclins." *Cell* 73:499–511 (1993).
Durfee et al., "The retinoblastoma protein associates with the protein phosphatase type 1 catalytic subunit." *Genes Dev.,* 7:555–569 (1993).
Dyson et al., "Adenovirus E1A makes two distinct contacts with the retinoblastoma protein." *J. Virol.,* 66:4606–4611 (1992).
Ewen et al., "Functional interactions of the retinoblastoma protein with mammalian D–type cyclins." *Cell,* 73:487–497 (1993).
Ford et al., "Nuclear protein with sequence homology to translation initiation factor eIF–4A." *Nature,* 332:736–738 (1988).
Harlow et al., "Association of adenovirus early region 1A proteins with cellular polypeptides." *Mol. Cell. Biol.,* 6:1579–1589 (1986).

Hirling et al., "RNA helicase activity associated with the human p68 protein." *Nature,* 339:562–564 (1989).
Hu et al., "The regions of the retinoblastoma protein needed for binding to adenovirus E1A or SV40 large T antigen are common sites for mutations." *EMBO J.,* 9:1147–1155 (1990).
Huang et al., "Two distinct and frequently mutated regions of retinoblastoma protein are required for binding to SV40 T antigen." *EMBO J.,* 9:1815–1822 (1990).
Huang et al., "A cellular protein that competes with SV40 T antigen for binding to the retinoblastoma gene product." *Nature,* 350:160–162 (1991).
Huang et al., "The retinoblastoma protein region required for interaction with the E2F transcription factor includes the T/E1A binding and carboxy–terminal sequences." *DNA Cell Biol.,* 11:539–548 (1992).
Kaelin, Jr. et al., "Definition of the minimal simian virus 40 large T Antigen and adenovirus E1A–binding domain in the retinoblastoma gene product." *Mol. Cell. Biol.,* 10:3761–3769 (1990).
Keller and Maniatis, "Identification and characterization of a novel repressor of β–interferon gene expression." *Genes Dev.,* 5:868–879 (1991).
Kimelman et al., "E1a regions of the human adenoviruses and of the highly oncogenic simian adenovirus 7 are closely related." *J. Virol.,* 53:399–409 (1985).
M. Kozak, "An analysis of 5' noncoding sequences from 699 vertebrate messenger RNAs." *Nucl. Acids Res.* 15:8125–8148 (1987).
Krieg and Melton, "Functional messenger RNAs are produced by SP6 in vitro transcription of cloned cDNAs." *Nucl. Acids Res.,* 12:7057–7070 (1984).
Lane and Hoeffler, "SV40 large T shares an antigenic determinant with a cellular protein of molecular weight 68,000." *Nature,* 288:167–170 (1980).
Lillie et al., "Functional domains of adenovirus type 5 E1a proteins." *Cell,* 50:1091–1100 (1987).
Ludlow et al., "SV40 large T antigen binds preferentially to an under phosphorylated member of the retinoblastoma susceptibility gene product family." *Cell,* 56:57–65 (1989).
Mihara et al., "Cell cycle–dependent regulation of phosphorylation of the human retinoblastoma gene product." *Science,* 246:1300–1303 (1989).
E. Moran, "A region of SV40 large T antigen can substitute for a transforming domain of the adenovirus E1A products." *Nature,* 334:168–170 (1988).

(List continued on next page.)

*Primary Examiner*—Lila Feisee
*Assistant Examiner*—Christine Saoud
*Attorney, Agent, or Firm*—Campbell & Flores LLP

[57] ABSTRACT

The present invention provides PR domain peptides, which are about 100 to about 120 amino acids in length and contain three highly conserved sequences of about 10 to about 12 amino acids, separated by less conserved sequences of about 20 to about 35 amino acids.

18 Claims, 26 Drawing Sheets

OTHER PUBLICATIONS

Moran and Matthews, "Multiple functional domains in the adenovirus E1A gene." *Cell,* 48:177–178 (1987).

J.R. Nevins, "E2F: a link between the Rb tumor suppressor protein and viral oncoproteins." *Science,* 258:424–429 (1992).

Pawson and Gish, "SH2 and SH3 domains: from structure to function." *Cell* 71:359–362 (1992).

Qin et al., "Identification of a growth suppression domain within the retinoblastoma gene product." *Genes Dev.,* 6:953–964 (1992).

Quinlan et al., "Growth factor induction by the adenovirus type 5 E1A 12S protein is required for immortilization of primary epithelial cells." *Mol. Cell. Biol.,* 8:3191–3203 (1988).

Quinlan and Douglas, "Immortilization of primary epithelial cells requires first– and second–exon functions of adenovirus type 5 12S." *J. Virol.,* 66:2020–2030 (1992).

Ren et al., "Identification of a ten–amino acid proline–rich SH3 binding site." *Science,* 259:1157–1161 (1993).

Saraste et al., "The P–loop—a common motif in ATP– and GTP–binding proteins." *Trends. Biochem. Sci.,* 15:430–434 (1990).

Scheffner et al., "RNA unwinding activity of SV40 large T antigen." *Cell* 57:955–963 (1989).

Smith and Ziff, "The amino–terminal region of the adenovirus serotype 5 E1a protein performs two separate functions when expressed in primary baby rat kidney cells." *Mol. Cell. Biol.,* 8:3882–3890 (1988).

Subramanian et al., "Enhanced ras oncogene mediated cell transformation and tumorigenesis by adenovirus 2 mutants lacking the C–terminal region of E1a protein." *Oncogene,* 4:415–420 (1989).

Templeton et al., "Nonfunctional mutants of the retinoblastoma protein are characterized by defects in phosphorylation, viral oncoprotein association, and nuclear tethering." *Proc. Natl. Acad. Sci. USA,* 88:3033–3037 (1991).

Wang et al., "Identification of specific adenovirus E1A N–terminal residues critical to the binding of cellular proteins and the control of cell growth." *J. Virol.,* 67:476–488 (1993).

R.A. Weinberg, "Tumor suppressor genes." *Science,* 254:1138–1146 (1991).

Welch and Wang, "A C–terminal protein–binding domain in the retinoblastoma protein regulates nuclear c–Abl tyrosine kinase in the cell cycle." *Cell,* 75:779–790 (1993).

Whyte et al., "Association between an oncogene and an anti–oncogene: the adenovirus E1A proteins bind to the retinoblastoma gene product." *Nature* 334:124–129 (1988).

Whyte et al., "Cellular targets for transformation by the adenovirus E1A proteins." *Cell,* 56:67–75 (1989).

Walker et al., "Distantly related sequences in the α– and β–subunits of ATP synthase, myosin, kinases and other ATP–requiring enzymes and a common nucleotide binding fold." *Embo J.,* 1(8):945–951 (1982).

Chen et al., "Phosphorylation of the retinoblastoma gene product is modulated during the cell cycle and cellular differentiation." *Cell,* 58:1193–1198 (1989).

DeCaprio et al., "The product of the retinoblastoma susceptibility gene has properties of a cell cycle regulatory element." *Cell,* 58:1085–1095 (1989).

Iggo and Lane, "Nuclear protein p68 is an RNA–dependent ATPase." *EMBO J.,* 8(6):1827–1831 (1989).

Moran et al., "Identification of separate domains in the adenovirus E1A gene for immortilization activity and the activation of virus early genes." *Mol. and Cell. Biol.,* 6(10):3470–3480 (1986).

Buchkovich et al., "The retinoblastoma protein is phosphorylated during specific phases of the cell cycle." *Cell,* 58:1097–1105 (1989).

Chen et al., "Identification of a Human Homologue of Yeast Nuc2 Which Interacts with the Retinoblastoma Protein in a Specific Manner." *Cell Growth & Differ.* 6:199–210 (1995).

Bartholomew and Ihle, "Retroviral insertions 90 kilobases proximal to the Evi–1 myeloid transforming gene activate transcription from the normal promoter." *Mol. Cell. Biol.,* 11(4):1820–1828 (1991).

Morishita et al., "Expression of the Evi–1 zinc finger gene in 32Dc13 myeloid cells blocks granulocytic differentiation in response to granulocyte colony–stimulating factor." *Mol. Cell. Biol.,* 12(1):183–189 (1992).

Buyse et al., "The retinoblastoma protein binds to RIZ, a zinc–finger protein that shares an epitope with the adenovirus E1A protein." *Proc. Natl. Acad. Sci. USA,* 92:4467–4471 (1995).

Kreider et al., "Loss of erythropoietin responsiveness in erythroid progenitors due to expression of the Evi–1 myeloid–transforming gene." *Proc. Natl. Acad. Sci. USA,* 90:6454–6458 (1993).

Miyoshi et al., "t(8;21)breakpoints on chromosome 21 in acute myeloid leukemia are clustered within a limited region of a single gene, AML1." *Proc. Natl. Acad. Sci. USA,* 88:10431–10434 (1991).

Nucifora et al., "Consistent intergenic splicing and production of multiple transcripts between AML1 at 21q22 and unrelated genes at 3q26 in (3;21) (q26;q22)translocations." *Proc. Natl. Acad. Sci. USA,* 91:4004–4008 (1994).

Morishita et al., "Unique expression of the human Evi–1 gene in an endometrial carcinoma cell line: sequence of cDNAs and structure of alternatively spliced transcripts." *Oncogene,* 5:963–971 (1990).

Lee et al., "Dual roles of the retinoblastoma protein in cell cycle regulation and neuron differentiation." *Genes & Development,* 8:2008–2021 (1994).

Garriga et al., "Migrations of the *caenorhabditis elegans* HSNs are regulated by egl–43, a gene encoding two zinc finger proteins." *Genes & Development,* 7:2097–2109 (1993).

Turner et al., "Blimp–1, a novel zinc finger–containing protein that can drive the maturation of B lymphocytes into immunoglobulin–secreting cells." *Cell,* 77:297–306 (1994).

Weinberg Robert A., "The retinoblastoma protein and cell cycle control." *Cell,* 81:323–330 (1995).

Morishita et al., "EVI–1 zinc finger protein works as a transcriptional activator via binding to a consensus sequence of GACAAGATAAGATAAN$_{1-28}$ CTCATCTTC." *Oncogene,* 10:1961–1967 (1995).

Mitani et al., "Generation of the AML1–EVI–1 fusion gene in the t(3;21) (q26;q22) causes blastic crisis in chronic myelocytic leukemia." *EMBO J.,* 13(3):504–510 (1994).

Rechsteiner Martin, "Regulation of enzyme levels by proteolysis: the role of pest regions." *Adv. Enzyme. Regul.,* 27:135–151 (1988).

Huang Shi, "Blimp–1 is the murine homolog of the human transcriptional repressor PRDI–BF1." *Cell,* 78:9 (1994).

Morishita et al., "Retroviral activation of a novel gene encoding a zinc finger protein in IL–3–dependent myeloid leukemia cell lines." *Cell,* 54:831–840 (1988).

Morishita et al., "The Evi–1 zinc finger myeloid transforming gene is normally expressed in the kidney and in developing oocytes." *Oncogene*, 5:1419–1423 (1990).

Perkins et al., "Patterns of Evi–1 expression in embryonic and adult tissues suggest that Evi–1 plays an important regulatory role in mouse development." *Development*, 111:479–487 (1991).

GAATTCCCGG CTCACTGAAG CTTGGCACGT GCGCTCTGGA
ATATCTGAAT GATCTCAGTA CAATGAAGGA GTGCCTTTTC
CCTTTCTACC CTGCCTCCTT GAAGCATGCA TTAGAGTCGT
T (SEQ ID NO: 94)

```
RIZ           1125  CNVCESPFLSIKDLTKHLSVHAEEWPFKCEFCVQLFKVKTDLSEHRFLLHGVGNIFVCSVCKKEFAFLCNLQQHQRDLHPDEVCTH   1210
PRDI-BF1       543  CNVCAKTFGQLSNLKVHLRVHSGERPFKCQTCNKGFTQLAHLQKH-YLVHTGEKPHECQVCHKRFSSTSNLKTHLR-LHSGEKPYQ    626
CONSENSUS           CNVC...F.....L..HL.VH..E.PFKC..C..F.....L..H..L.H.......C.VC.K.F....NL..H.R.LH..E....
DNA-CONTACTS             *  *                          *   *                                  *  *     *
```

FIG. 2C-1

```
RIZ             39  TRIGVWATKPILKGKKFGPFVGDKKKRSQVRNNV- -YMWEVYYPNLGWMCIDATDPEKGNWLRYVNWACSGEEQNLFPL   115
PRDI-BF1        60  EVIGVMSKEYIPKGTRFGPLIGEIYTNDTVPKNANRKYFWRIYSRGELHHFIDGFNEEKSNWMRYVNPAHSPREQNLAAC   139
CONSENSUS           ..IGV......I.KG..FGP..G......V..N...Y.W..Y.......ID....EK.NW.RYVN.A.S..EQNL...

RIZ            116  EINRAIYYKTLKPIAPGEELLVWYNGEDNP                                                    145
PRDI-BF1       140  QNGMNIYFYTIKPIPANQELLVWYCRDFAE                                                    169
CONSENSUS           .....IY..T.KPI.....ELLVWY......
```

1. Clone 5Y

```
G GAG TGG GGG CCA GTC ACC CGG AGC CTT CAG CGC
  E   W   G   P   V   T   R   S   L   Q   R

AGC ACC AAG CAG GAG CTG AAG GAC TTG CAG    (95)
 S   T   K   Q   E   L   K   D   L   Q    (102)
```

2. Clone 1Y

```
GGG GCC GGC GAA ACA GCG GCG GCG GCG GCG GCC CTC
 G   A   G   E   T   A   A   A   A   A   A   L

GGT GCT CTG AGG CTG GGC CGG CGG GCG CGG    (96)
 G   A   L   R   L   G   R   R   A   R    (103)
```

* - Number in parentheses is SEQ ID NO:.

FIG. 9B

|  | 10 | 20 | 30 | 40 | 50 | |
|---|---|---|---|---|---|---|
|  | 1234567890 | 1234567890 | 1234567890 | 1234567890 | 1234567890 | |
|  | CCTACAGCTA | CCCTCACAAG | CATGAAGTGC | TGTGGCTGTT | CCTTATCCTA | 50 |
|  | ATGATGCGCT | TTTGTCCCGT | AAATGTTAAC | ACTCATGAAG | CATACCCCGG | 100 |
|  | CCTCTCAGTT | CTTGAGGGCC | TCCCCACCGC | AGCAGCAAGG | AAAGCTCACG | 150 |
|  | AACCCCAAAC | CTGGCAAGTC | ACCTGCAGCC | CATGGTGAGC | TCTGGGAAGT | 200 |
|  | GTGGTTGAGG | CCTTGGGGTC | ACTCCTTTTT | TGCATGTGCA | AATGTGCTGG | 250 |
|  | TCACCCTTCA | ACGCTCCCAG | ACGGTCAGGA | AAACTGTTCC | AATCATGAAA | 300 |
|  | AGGGGGGATG | ATTTTGTAAA | GTGGCATTTC | CTGGTCAGTG | GTGGTCTTCA | 350 |
|  | AGACGACAGC | TCTGTATCTG | CCATGTGAAG | AGAATTAACA | ATAAAAGTGT | 400 |
|  | GAAGAGCGAA | AAAAAAAAAA | AAAAAAAAAA | AAAAAAAAAA | AAAAAAAAAA | 450 |
|  | AAAAAAAAAA | AAAGCGCCGG | CCGC |  |  | 474 |

FIG. 9C

```
hRIZ         MQNMTEEVA ATETLAEVPE HVLRGLPEEV RLFPSAVDKT RIGVWATKPI LKGKKFGPFV   60
rRIZ         MQNMTEEVA ATETLAEVPE HVLRGLPEEV RLFPSAVDKT RIGVWATKPI LKGKKFGPFV   59
Consensus    MQN TE VA ATETLAEVPE HVLRGLPEEV RLFPSAVDKT RIGVWATKPI LKGKKFGPFV   60 hRIZ         GDKKKRSQVK NNVYMWEVYY PNLGWMCIDA TDPEKGNWLR YVNWACSGEE QNLFPLEINR  120
rRIZ         GDKKKKRSQVR NNVYMWEVYY PNLGWMCIDA TDPEKGNWLR YVNWACSGEE QNLFPLEINR  119
Consensus    GDKKKRSQV  NNVYMWEVYY PNLGWMCIDA TDPEKGNWLR YVNWACSGEE QNLFPLEINR  120 hRIZ         AIYYKTLKPI APGEELLVWY NGEDNPEIAA AIEEERASAR SKRSSPKSRK GKKKS ENKN  180
rRIZ         AIYYKTLKPI APGEELLVWY NGEDNPEIAA AIEEERASAR SKRSSPKSRR GKKKS ENKN  179
Consensus    AIYYKTLKPI APGEELLVWY NGEDNPEIAA AIEEERASAR SKRSSPKSR  GKKKS ENKN  180 hRIZ         KGNKIQDIQL KNSEHETTSA NMRISAEGPK EDEENPEASA LEQPAHLEV ASQEVFPELA  240
rRIZ         KGIRTHPTQL KPSEHDETHA NMRISAEGPK EELEIPEASA FEQPAFLEEV GNQDAVPQVA  239
Consensus    KG   L K SE   T A NMR SAEGPK E E   ASA  EQPA  LEV  Q      A     240 hRIZ         TPAPAQEPQP EFDERLHAAA CEVNDLQEEE EEDDDDDLE DEGEEEAAMP               300
rRIZ         IPLPAEPQP  EVDGKQEVTD CEVNDIVEEEE EEEEE---LG EDGUEEAAMP               295
Consensus    PA EPQP E D         CEVND  EEE EEE       E  EEA MP               300 hRIZ         NENSKEPEI RCEKPEDLL EEPKTISEL LEDCSEVTPA MQIPRTKEEA NGDVETFMF    360
rRIZ         NEESKEPEI RCEKPEDLL EEPQSMSNEA REDSPDVTPP PHTPRAREEA NGDVETFMF    355
Consensus    N  S KEPEI RC EKPEDLL EEP    E    S VTP         PR EEA NGDV ETFMF   360
```

FIG. 10A

```
hRIZ        PCQHCERKF  TKQGLERHMH IHISTNHAF KCKYCGK FG TQINRRRHER RHE GLKR P   420
rRIZ        PCQHCERKF  TKQGLERHMH IHISTNHAF KCKYCGK FG TQINRRRHER RHE GLKR P   415
Consensus   PCQHCERKF. TKQGLERHMH IHIST.N.AF KCKYCGK.FG TQINRRRHER RHE.GLKR.P   420 hRIZ        SVTLQ SED  ADGKA GENV  SKD SSPPS  LG DCLI NS EK SQTI NS S VEENGEVK  480
rRIZ        SVTLQ SEDP .DGK  GENV  SKD SSPPQ  LC DCLI NS EK IS QEV LNS S FEENGEVK 473
Consensus   S.TLQ SED. .DGK. GENV. SKD.SSPP.. LG.DCLI.NS EK.SQ.... NS.S.VEENGEVK  480 hRIZ        ELHPCKYCKK VFGTHTNMRR HQRRVHERHL IPKGVRRKGG L E PQPPAE QAQAT QNVYV   539
rRIZ        ELHPCKYCKK VFGTHTNMRR HQRRVHERHL IPKGVRRKGG L E PQPPAE QAPPS QNVYV   533
Consensus   ELHPCKYCKK VFGTHTNMRR HQRRVHERHL IPKGVRRKGG L.E.PQPPAE QA... QNVYV   540 hRIZ        PSTEPEEEGE DDVYIMDIS SNISENLNYY IDGKIQTN NN TSNCDVIEME S SA LYGIN      599
rRIZ        PSTEPEEEGE DDVYIMDIS SNISENLNYY IDGKIQTN SS TSNCDVIEME S SA LYGID      593
Consensus   PSTEPEEEGE DDVYIMDIS SNISENLNYY IDGKIQTN... TSNCDVIEME S.SA LYGI.      600 hRIZ        CLLTPVTVEI TQNIK TQVP VTEDL KEPL QSTNSE KKR RTASPP LPK IK ET SDPM      659
rRIZ        CLLTPVTVEI TQNIK TQVS VTDL KDSP SSTNCE SKKR RTASPP LPK IK ET SSDST     653
Consensus   CLLTPVTVEI TQNIK.TQV. VT.DL.K... .STN.E..KKR RTASPP.LPK IK.ET.SD..     660 hRIZ        VPSCSLSLPL SISTT  VSF HKEKS VYLSS KLKQLLQTQD KLT PAGTSA  E  KLGPVC   719
rRIZ        APSCSLSLPL SISTE  VSF HKEKS VYLSS KLKQLLQTQD KLT PAG SA  EIF KLGPVC   713
Consensus   .PSCSLSLPL SIST.. VSF HKEK. VYLSS KLKQLLQTQD KLT.PAG.SA. E.  KLGPVC   720
```

FIG. 10B

| | | |
|---|---|---|
| hRIZ | VSAPASMLPV TSSRFKRRTS SPPSSPQHSP ALRDFGKP D GKAAWTDAQL TSKKEKLESH | 779 |
| rRIZ | ASAPASMLPV TSSRFKRRTS SPPSSPQHSP ALRDFGKP D GKAAWTDTVL TSKKQKLESR | 773 |
| Consensus | SAPASMLPV TSSRFKRRTS SPPSSPQHSP ALRDFGKP D GKAAWTD L TSKK KLES | 780 |
| hRIZ | SDSPAWSLSG RDERETMSPP CFDEYKMSKE WTASSNFSSV CNQQPLDLSS GVKQKEGTG | 839 |
| rRIZ | SDSPAWSLSG RDERETISPP CFDEYKIISKE WTASSIFSSV CNQQPLDLSS GVKQKEGTG | 833 |
| Consensus | SDSPAWSLSG RDERET SPP CFDEYK SKE W ASS FSSV CNQQPLDLSS GVKQK EGTG | 840 |
| hRIZ | KTPVQWESVL DLSVHKKYCS HSVQPTCSAV KKKKPTTCML QKVLLNEYNQ | 899 |
| rRIZ | KTPVRWESVL DLSVHKKQPC HLAQP--AA KKKKPTTCML QKVLLNEYNQ | 889 |
| Consensus | KTPV WESVL DLSVHKK C H QP A KK KPTTCML QKVLLNEYNQ | 900 |
| hRIZ | ICLPMENPAD QTRSPSPCKS LEAQPDRHLG PISGFPAPTV ESHPIVC PS SPLQTFSLS | 958 |
| rRIZ | VSLPHEITPE VTRSPSPCKS PDTQPDRHLG PSSCSVPTR ESRPEWCPS SPLQTHSLS | 949 |
| Consensus | LP E TRSPSPCKS QPDR LG P PT ES P C PS SP LQT SLS | 960 |
| hRIZ | SGQLPPLLHP THPSSPPPPCP PVLTVATPPP PLLPTVPLPA PSSEASPHRC PSPHSNHTAQ | 1018 |
| rRIZ | SGQLPPLLHP THPSSPPPPCP PVLTVATPPP PLLPTVPLSH PSSSASPQQC PSPFSNITAQ | 1009 |
| Consensus | SGQLPPLL P T PSSPPPPCP PVLTVATPPP PLLPTVPL PSS ASP C PSP SN TAQ | 1020 |
| hRIZ | SPLPILSPTV SPSPSPIPPV EPLMSAASPG PPTLSSSSSS SSSSGSFSSS SUSSSPPPPP | 1078 |
| rRIZ | SPLPILSPTV SPSPSPIPPV EPLMSAASPG PPTLSSSSSS SSSFRSSSSS SUSSSPPPP - | 1067 |
| Consensus | SPLPILSPTV SPSPSPIPPV EPLMSAASPG PPTLSSSSSS SSS S S SPP P | 1080 |

FIG. 10C

| | | |
|---|---|---|
| hRIZ | LSAI SSVVSS GDNLEASLPM ISFKQEE EN EGLKP EEPQ SAAEQQ VVQ ETF KNF CN | 1138 |
| rRIZ | LSAV SSVVSS GDNLEASLPA VTFKQEE ES EGLKP VEEAP PAGQQS VVQ ETF KNF CN | 1126 |
| Consensus | LSA. SSVVSS GDNLEASLP. ..FKQEE .E. EGLKP .E. .... .A..Q.. VVQ ETF KNF .CN | 1140 |

| | | |
|---|---|---|
| hRIZ | VCESPFLSIK DLTKHLS HA EEWPFKCEFC VQLFK KTDL SEHRFLLHGV GNIFVCSVCK | 1198 |
| rRIZ | VCESPFLSIK DLTKHLS MHA EEWPFKCEFC VQLFK KTDL SEHRFLLHGV GNIFVCSVCK | 1186 |
| Consensus | VCESPFLSIK DLTKHLS .HA EEWPFKCEFC VQLFK. KTDL SEHRFLLHGV GNIFVCSVCK | 1200 |

| | | |
|---|---|---|
| hRIZ | KEFAFLCNLQ QHQRDLHPDK VCTHHEFESG TLRPQNFTDP SKA VEHM S LPE PLETSK | 1258 |
| rRIZ | KEFAFLCNLQ QHQRDLHPDE VCTHHEFESG TLRPQNFTDP SKA VEHM S LPE PLETSR | 1246 |
| Consensus | KEFAFLCNLQ QHQRDLHPD. VCTHHEFESG TLRPQNFTDP SKA VEHM S LPE PLETS. | 1260 |

| | | |
|---|---|---|
| hRIZ | EEE LNDSSE ELYTTIKIMA SGIKTKDPDV RLGLNQHYPS FKPPPFQYHH RNPMGIGVTA | 1318 |
| rRIZ | EEE LNDSSE ELYTTIKIMA SGIKTKDPDV RLGLNQHYPS FKPPPFQYHH RNPMGIGVTA | 1305 |
| Consensus | EEE LNDSSE ELYTTIKIMA SGIKTKDPDV RLGLNQHYPS FKPPPFQYHH RNPMGIGVTA | 1320 |

| | | |
|---|---|---|
| hRIZ | TNFTTHNIPQ TFTTAIRCTK CGKGVDNMPE LHKHILACAS ASDKKRYTPK KNPVPLKQTV | 1378 |
| rRIZ | TNFTTHNIPQ TFTTAIRCTK CGKGVDNMPE LHKHILACAS ASDKKRYTPK KNPVPLKQTV | 1365 |
| Consensus | TNFTTHNIPQ TFTTAIRCTK CGKGVDNMPE LHKHILACAS ASDKKRYTPK KNPVPLKQTV | 1380 |

| | | |
|---|---|---|
| hRIZ | QPKNGVVVLD NSGKNAFRRM GQPKRL FFV EL KMS NKL KL ALKKKNQ LVQKAILQKN | 1438 |
| rRIZ | QPKNGVVVLD NSGKNAFRRM GQPKRL FFV EL KMS NKL KL ALKKKNQ LVQKAILQKN | 1425 |
| Consensus | QPKNGVVVLD NSGKNAFRRM GQPKRL F.V EL. KMS. NKL KL ALKKKNQ LVQKAILQKN | 1440 |

FIG. 10D

```
hRIZ        KSAKQKADLK  NAQESSHIC PYCNREFTYI  GSLNKHAAFS  CPKKPLSPK  KVSHSSKKQ    1498
rRIZ        RAAKQKADLR  DTSEASSHIC PYCHREFTYI  GSLNKHAAFS  CPKKPLSPK  KVSHSSKKQ    1485
Consensus        AKQKADL       SSHIC PYC  REFTYI  GSLNKHAAFS  CPKKPLSP K  KVSHSSKKQ  1500 hRIZ        GHSSPASSDK  NSNSNHRRRT ADMEIKMQSM  QIPLGKTRAR  SEGPIQVFLP  SSSFRSRQNM   1558
rRIZ        GHASSSSSDR  NSCHHRRRT ADIEIKMQST  QNPLGKTRAR  STGPVCASLP  SSSFRSRQNM   1545
Consensus   GH  S  SSD   N     RRRT AD  EIKMQS   Q PLGKTRAR  S  GP  Q       LP  SSSFRS ONM  1560 hRIZ        KFAASVKSKK  HSSSSLRNSS PIRMAKITHV  EGKKPKAVAK  HSAQLSSKT  SRELHVRVQK   1618
rRIZ        KFAASVKSKK  NSSSSLRNSS PIRMAKITHV  EGKKPKAVAK  HSAQLSSKG  SRHLHVRVQK   1605
Consensus   KFAASVKSKK   SSSSLRNSS PIRMAKITHV  EGKKPKAVAK  HSAQLSSK    SR LHVRVQK  1620 hRIZ        SKAVIQSKST  LASKRTDRF NIKSRERSGG  PMTRSLQLAA  AADLSENKRE  DESAKQELKD   1678
rRIZ        SKAVMQSKTA  LASKRTDRF IVKSRERSGG  PITRSLQLAA  AADLSEFFRE  DESARHELKD   1665
Consensus   SKAV QSK    LASK RTDRF   KSRERSGG  P TRSLQLAA  AADLSE      RE D SA  ELKD  1680 hRIZ        FSYSLRLASR  CSPPAAFYIT RQTRKVKAIA  ARQFQGPFFK  E             1719
rRIZ        FSYSLRLASR  CSSSTAEYIT RQCRKVKAPA  ATFFQGPFFK  EX            1707
Consensus   FSYSLRLASR  C        A YIT RQ  RKVKA A  A   FQGPF K  E        1722
```

FIG. 10E

```
          10        20        30        40        50        60
123456789012345678901234567890123456789012345678901234567890
GTGTACTACCCAAATTTGGGGTGGATGTGCATTGATGCCACTGATCCGGAGAAGGGCAAC    60
ValTyrTyrProAsnLeuGlyTrpMetCysIleAspAlaThrAspProGluLysGlyAsn

TGGCTCCGCTATGTGAACTGGGCTTGCTCAGGAGAAGAACAGAATTTATTCCACTGGAA   120
TrpLeuArgTyrValAsnTrpAlaCycSerGlyGluGluGlnAsnLeuPheProLeuGlu

ATCAACAGAGCCATTACTATAAAACTTAAAGCCAATCGCGCCTGGCGAGGAGCTCCTG    180
IleAsnArgAlaIleTyrTyrLysThrLeuLysProIleAlaProGlyGluGluLeuLeu

GTCTGGTACAAATGGGAAGACAACCCCGAGATAGCAGCTGCGATTGAGGAAGAGCGAGCC  240
ValTrpTyrAsnGlyGluAspAsnProGluIleAlaAlaAlaIleGluGluArgAla

AGCGCCCGAGCAAGCGGAGCTCCCCGAAGAGCCGGAGAGGGAAGAAGAAATCACAGGAG  300
SerAlaArgSerLysArgSerSerProLysSerArgArgGlyLysLysSerGlnGlu

AATAAAAAACAAAGGCATCAGAACCCAGGCTGCAGCGCGGAAGGCGAGCGAGCTGGACTCC 360
AsnLysAsnLysGlyIleArgThrGlnAlaAlaAlaArgLysAlaSerGluLeuAspSer

ACCTCTGCAAACATGAGGGGCTCTGCAGAAG                               391
ThrSerAlaAsnMetArgGlySerAlaGlu
```

FIG. 14

PR DOMAIN PEPTIDES

This application is a continuation-in-part (CIP) of U.S. Ser. No. 08/399,411, filed Mar. 6, 1995, now U.S. Pat. No. 5,831,008, which is a CIP of U.S. Ser. No. 08/292,683, filed Aug. 18, 1994, now abandoned. The entire contents of each of the related applications are incorporated herein by reference.

This invention was made in part with government support under CA57496, awarded by the National Institutes of Health, and 5T30 CA30199, awarded by the Cancer Center Core. The United States government has certain rights in this invention.

BACKGROUND OF THE INVENTION

1. Field of the Invention

This invention relates to the field of molecular biology and, in particular, to nucleic acid molecules encoding an Rb-interacting zinc finger (RIZ) protein and a conserved domain of a RIZ protein that is involved in regulating gene transcription.

2. Background Information

The retinoblastoma Rb protein is known to play a key role in controlling normal cell proliferation and differentiation. The ability of a cell to divide requires the cell to pass through the various phases of the cell cycle. Although Rb is believed to keep normal cells from dividing by maintaining them in a phase of the cell cycle known as $G_1$ or $G_0$, the precise mechanism underlying Rb function is unknown. It is known, however, that Rb can bind various cellular proteins, includingproteins involved in regulating gene transcription. Thus, Rb may exert its action by interacting with such cellular proteins.

The role that Rb plays in controlling cell growth makes it an attractive target for promoting the growth of tissues that normally do not grow because of the action of Rb. For example, cardiac muscle tissue and nervous tissue that have lost function due to cell death are not usually repaired by subsequent proliferation of the remaining live cells. Thus, a method to block the growth controlling function of Rb can be useful for inducing tissue repair in situations of cardiac or neural cell death.

Rb also is known as a tumor suppressor since the abnormal growth of a cancer cell can result from inactivation of Rb protein. Such inactivation can occur either due to a mutation or to inactivation of Rb protein subsequent to binding a viral oncoprotein, a product of an oncogenic tumor virus. A particular region in Rb called the Rb pocket appears to be critical for its growth controlling function since Rb inactivation by mutation or by oncoprotein binding impacts this region.

The importance of the Rb pocket in the functioning of Rb and the understanding that viral oncoproteins can regulate Rb by binding the pocket suggest that there may be normal cellular proteins that can regulate the function of Rb by binding the pocket. The identification of such proteins will provide new approaches to regulate the control of cell proliferation mediated by Rb in diseases such as those that involve loss of cardiac or neural function or in the control of cancer.

Thus, a need exists to identify proteins that can bind to and regulate Rb in order to provide new approaches for controlling cell proliferation and differentiation. The present invention satisfies this need and provides related advantages as well.

SUMMARY OF THE INVENTION

The present invention provides substantially purified mammalian Rb-interacting zinc finger proteins (RIZ), including for example, human RIZ and rat RIZ. In addition, the invention provides active fragments of a RIZ such as the sequences EIRCEEKPEDL (SEQ ID NO: 6) and EIRCDEKPEDL (SEQ ID NO: 91), which bind Rb. The invention also provides antibodies that can specifically bind to a RIZ or a mutant RIZ.

The invention further provides nucleic acid molecules encoding mammalian RIZ and active fragments thereof, vectors containing the nucleic acid molecules and host cells containing the vectors. In addition, the invention provides nucleotide sequences that can specifically hybridize to a nucleic acid molecule encoding a RIZ or a mutant nucleic acid molecule encoding a RIZ.

In addition, the invention provides a peptide comprising a PR domain, which is conserved among various proteins and can be involved in regulating the transcription of a target gene. In general, a PR domain peptide contains about 100 to about 120 amino acids that characteristically are arranged as a series of three highly conserved sequences of about ten to about twelve amino acids each, which are separated from each other by less conserved sequences of about 24 to about 34 amino acids each. A PR domain of the invention is exemplified by the PR domain present in the RIZ protein disclosed herein and by the PR domain present in the proteins PRDI-BF1, Evi-1 and egl-43.

The present invention further provides fusion proteins comprising a PR domain of the invention operably linked to a peptide that can bind to a DNA regulatory element. For example, a fusion protein of the invention can comprise a PR domain operably linked to a peptide that binds to a particular gene promotor or enhancer, wherein binding of the fusion protein to a target gene, which is a gene containing the particular promotor or enhancer, can alter expression of the target gene. Thus, a fusion protein of the invention can be useful for regulating the transcription of one or more target genes.

In addition, the invention further provides methods of identifying transcription factors and oncogenic proteins that bind a PR domain peptide or a RIZ active fragment containing a PR domain. The identification of such factors and proteins provides new approaches to manipulate cell differentiation and transformation.

The invention also provides a screening assay useful for identifying agents that can effectively alter the association of a RIZ with a second molecule such as Rb or can effectively alter the activity of a RIZ. By altering the association of a RIZ with a second molecule or altering the activity of a RIZ, an effective agent can modulate a function of a cell such as cell proliferation.

The invention further provides methods for promoting the growth of a cell such as a neural cell or cardiac muscle cell by contacting the cell with an effective agent. For example, cell growth can be promoted by introducing into a cell an effective agent such as an expression vector having an expression control sequence operably linked to a nucleotide sequence encoding an active fragment of a RIZ, wherein the active fragment lacks the growth-suppressing properties of a complete RIZ protein. In addition, the invention provides methods for restoring normal controlled cell growth to cancer cells by introducing into the cancer cells an expressible nucleic acid molecule encoding a complete RIZ protein.

The invention also provides methods of detecting a RIZ in a sample by detecting the presence of the RIZ protein or of a nucleic acid molecule encoding the RIZ. Such methods can be used to diagnose a pathology characterized by an increased or decreased level of expression of a RIZ in a cell or by expression of a mutant RIZ. Such a method also can be used to diagnose a pathology characterized by a mutant nucleic acid molecule encoding a RIZ.

The invention further provides methods useful for isolating Rb tumor suppressor protein or a mutant Rb from a sample. For example, Rb can be isolated from a sample by affinity chromatography using a RIZ or a RIZ active fragment such as the sequences EIRCEEKPEDL (SEQ ID NO: 6) or EIRCDEKPEDL (SEQ ID NO: 91).

BRIEF DESCRIPTION OF THE FIGURES

FIGS. 1A and 1B show alternative nucleotide sequences (SEQ ID NOS: 1 and 94) and the deduced amino acid (a.a.) sequence (SEQ ID NO: 2) of full-length rat RIZ protein.

FIG. 1A shows the cDNA sequence (SEQ ID NO: 1) and the deduced a.a. sequence of full-length rat RIZ protein (SEQ ID NO: 2). Numbers at right indicate nucleotide position; numbers at left indicate amino acid position. The following features are underlined: an upstream in-frame stop codon (nucleotide position 100–102), a cr2 core motif (a.a. positions 304–309), 8 zinc fingers (a.a. positions 357–377, 478–499, 387–407, 1125–1203 (finger 4–6), 1323–1343 and 1445–1466) and a putative nuclear localization signal (a.a. positions 867–874). A putative leucine zipper is located from a.a. position 667–695; T, H and L residues within the zipper are underlined. Single letter amino acid symbols are used.

FIG. 1B shows an alternative nucleotide sequence (SEQ ID NO: 94), which is present at the 5'-end of a nucleotide sequence encoding rat RIZ (SEQ ID NO: 2). The alternative nucleotide sequence (SEQ ID NO: 94) replaces nucleotides 1 to 91 at the 5'-end of the nucleotide sequence shown in FIG. 1A (SEQ ID NO: 1).

Figures 2A, 2B-1, 2B-2:
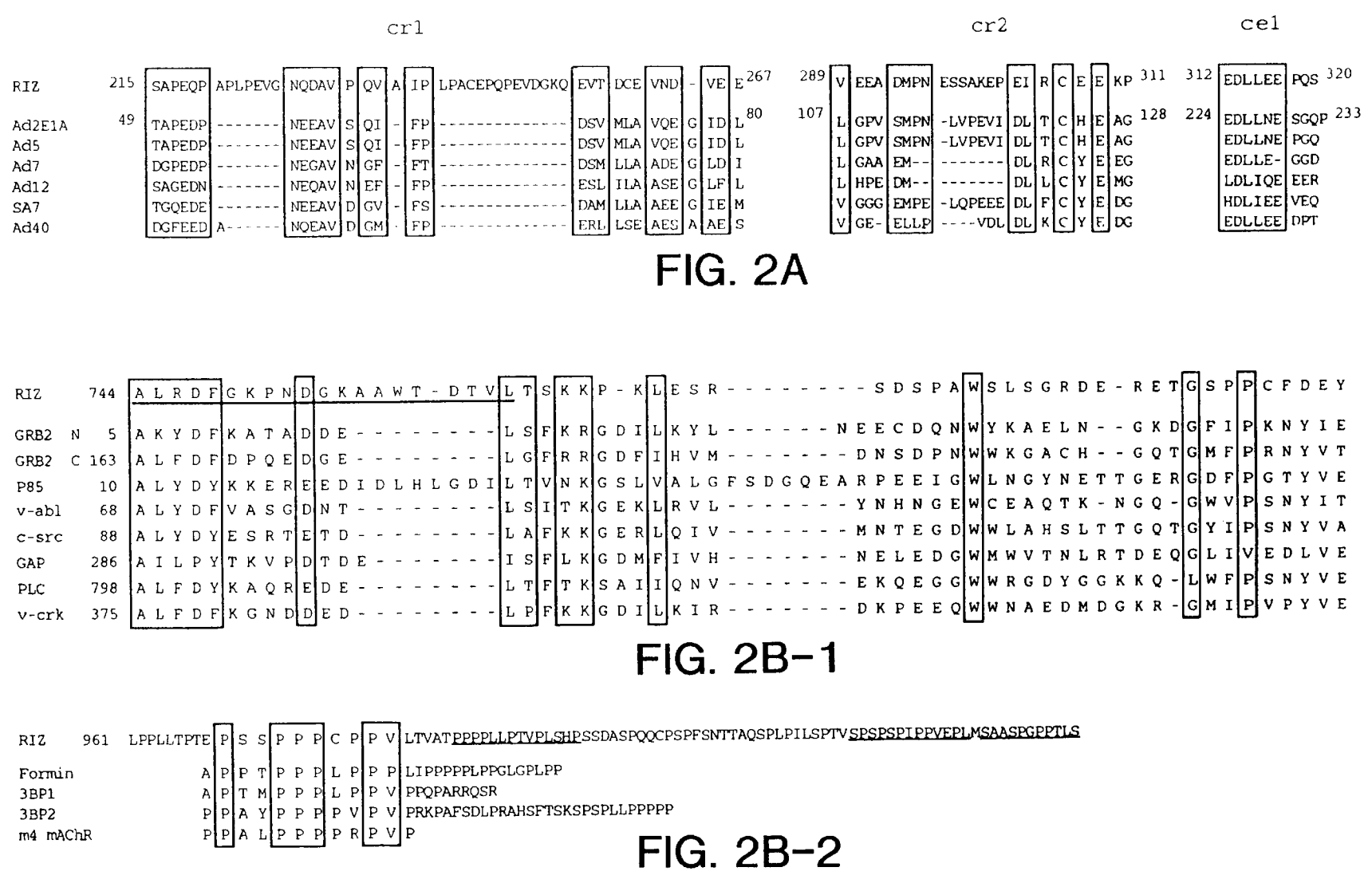

FIGS. 2A to 2C show homologies between rat RIZ and various other proteins. Single letter amino acid symbols are used. Numbers indicate amino acid positions in relation to the complete protein.

FIG. 2A compares RIZ amino acid sequences with various E1A sequences. E1A sequences of the different strains of adenoviruses are from Kimelman et al., *J. Virol.* 53:399–409 (1985), Moran and Mathews, *Cell* 48:177–178 (1987), and Ishino et al., *Virology* 165:95–102 (1988). Identical or closely related residues are boxed. Single letter amino acid symbols are used. Sequence domains, RIZ cr1 (SEQ ID NO: 79), Ad2E1A cr1 (SEQ ID NO: 44), Ad5 cr1 (SEQ ID NO: 45), Ad7 cr1 (SEQ ID NO: 46), Ad12 cr1 (SEQ ID NO: 47), EA7 cr1 (SEQ ID NO: 48), Ad40 cr1 (SEQ ID NO: 49), RIZ cr2 (SEQ ID NO: 65), Ad2E1A cr2 (SEQ ID NO: 66), Ad5 cr2 (SEQ ID NO: 67), Ad7 cr2 (SEQ ID NO: 68), Ad12 cr2 (SEQ ID NO: 69), EA7 cr2 (SEQ ID NO: 70), Ad40 cr2 (SEQ ID NO: 71), RIZ ce1 (SEQ ID NO: 72), Ad2E1A ce1 (SEQ ID NO: 73), Ad5 ce1 (SEQ ID NO: 74), Ad7 ce1 (SEQ ID NO: 75), Ad12 ce1 (SEQ ID NO: 76), EA7 ce1 (SEQ ID NO: 77) and Ad40 ce1 (SEQ ID NO: 78) are shown.

FIG. 2B shows RIZ putative SH3 and SH3-binding domains. Panel a: Sequence comparison of RIZ with other known SH3 domain-containing proteins (Lowenstein et al., *Cell* 70:431–442 (1992)). Identical or closely related residues are boxed and the phosphate-binding loop in RIZ (SEQ ID NO: 80) is underlined. Sequences from GRB2 N-terminus (SEQ ID NO: 50), GRB2 C-terminus (SEQ ID NO: 51), P85 (SEQ ID NO: 52), v-abl (SEQ ID NO: 53), c-src (SEQ ID NO: 54), GAP (SEQ ID NO: 55), PLC (SEQ ID NO: 56) and v-crk (SEQ ID NO: 57) are shown. Panel b: A RIZ putative SH3-binding motif compared with SH3 motifs from known SH3-binding proteins (Ren et al., *Science* 259: 1157–1161 (1993)). Identical or closely related residues are boxed. Sequences from (SEQ ID NO: 81) Formin (SEQ ID NO: 58), 3BP1 (SEQ ID NO: 59), 3BP2 (SEQ ID NO: 60) and m4mAChR (SEQ ID NO: 61) are shown.

FIG. 2C shows homology between RIZ and PRDI-BF1 proteins (Keller and Maniatis, *Genes Devel.* 5: 868–879 (1991)). Panel a: Alignment of RIZ zinc fingers 4 to 6 (SEQ ID NO: 82) with PRDI-BF1 zinc fingers 1 to 3 (SEQ ID NO: 62). A consensus sequence is shown with nonidentical residues indicated by dots. Potential DNA contact residues are marked by stars (Pavletich and Pabo, *Science* 252:809–817 (1991)). Panel b: Amino terminal homology between RIZ (a.a. position 39–115: SEQ ID NO: 83 and a.a. position 116–145: SEQ ID NO: 84) and PRDI-BF1 (a.a. position 60–139: SEQ ID NO: 63 and a.a. position 140–169: SEQ ID NO: 64)). A consensus sequence is shown with nonidentical residues indicated by dots.

FIG. 5A: Purified glutathionine S-transferase fusion protein containing a C-terminal RIZ fragment (a.a. position 245–573) was tested for binding to $^{35}$S-labeled Rb wild-type (wt-Rb) and to various deletion mutants (lanes 2–5) as shown in FIG. 5B. Wild-type (wt) full length Rb (A9), Cys to Phe mutation of full length Rb (H209), Rb deletion mutants from amino acid positions 515–619 (NM), 585–697 (PP) and 804–928 (B3) are shown.

FIG. 5B: Schematic map of Rb wild-type (wt-Rb) and Rb deletion mutants. The two sub-domains of the Rb pocket are represented by black boxes. Mutants that bind a glutathionine S-transferase (GST) RIZ (a.a. position 245–573) are indicated by a "+" sign. p56 Rb: 56 kD fragment of Rb from a.a. position 379–928.

FIG. 7A: SDS-PAGE (10% acrylamide) and Coomassie blue staining of GST; GSTZ13: GST-RIZ (a.a. position 245–573 containing zinc fingers 1–3); and GSTZ46: GST-RIZ (a.a. position 1114–1260 containing zinc fingers 4 to 6). KD indicates the migration of molecular weight markers.

FIG. 7B: Binding of $^{32}$P-labeled rat genomic DNA to GST, GSTZ13 and GSTZ46 in the presence of zinc ions.

FIG. 7C: As in FIG. 7B, except zinc ions were not added.

FIG. 8A: SDS-PAGE (10% acrylamide) and Coomassie blue staining of purified GST-G: GST-RIZ (760–949: RIZ GTPase domain fused C-terminal to glutathionine S-transferase).

FIG. 8B: $^{32}$P-GTP binding by GST (lane 1) and GST-G (lanes 2–6). Binding conducted in the absence or presence (lanes 3–6) of excess unlabeled nucleotides as indicated.

FIGS. 9A to 9C show alternative nucleotide sequences (SEQ ID NOS: 3 and 95–96), the deduced amino acid sequence (SEQ ID NO: 4) of full-length human RIZ and, additional 3' untranslated sequence of human RIZ cDNA (SEQ ID NO: 97).

FIG. 9A shows a complete nucleotide sequence (SEQ ID NO: 3) and the deduced amino acid sequence (SEQ ID NO: 4) of full-length human RIZ. Three letter amino acid symbols are used. Numbers at right indicate the nucleotide position.

FIG. 9B shows two alternative nucleotide sequences (SEQ ID NOS: 95–96), which replace the first 129 nucleotides present at the 5'-end of the nucleotide sequence shown in FIG. 9A (SEQ ID NO: 3). The encoded amino acid sequences for clones 5Y and 1Y are shown (SEQ ID NOS: 102 and 103, respectively).

FIG. 9C presents 3' untranslated sequence of human RIZ cDNA including the poly A tail (SEQ ID NO: 97). The sequence is located in human RIZ cDNA at the far 3' end of the cDNA, downstream of the 3' untranslated sequence shown in FIG. 9A (SEQ ID NO: 3). Additional untranslated sequence is present between the 3' end of SEQ ID NO: 3 and the 5' end of SEQ ID NO: 97.

FIG. 10 compares the complete human RIZ amino acid sequence (indicated as hRIZ; SEQ ID NO: 4) with the complete rat RIZ amino acid sequence (indicated as rRIZ; SEQ ID NO: 2). A consensus sequence is shown. Single letter amino acid symbols are used. Amino acids that are identical in hRIZ and rRIZ are shown as a ".".

FIG. 11A presents a northern blot of adult mRNA probed with $^{32}$P-labeled rat RIZ (1.9 Kb fragment representing a.a. position 245–883). Att-20 is a mouse pituitary cell line.

FIG. 11B presents an RNase protection experiment using RNA from a 16 day fetal rat (E16) and from an adult rat probed with $^{32}$P-labeled rat RIZ (representing a.a. position 463–574).

FIG. 14 shows the nucleotide sequence (SEQ ID NO: 104) and the deduced a.a. sequence (SEQ ID NO: 105) of coding exons 4–6 of mouse RIZ. Numbers at right indicate nucleotide position.

DETAILED DESCRIPTION OF THE INVENTION

Figure 3:
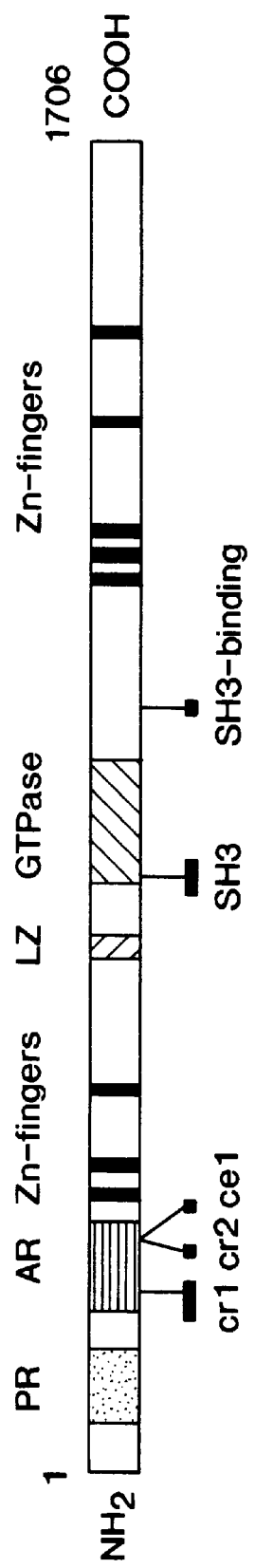
FIG. 3: Schematic representation of RIZ domain structure. PR: domain homologous to PRDI-BF1; AR: acidic region or E1A-related region; LZ: leucine-zipper; cr1 and cr2: conserved regions 1 and 2; ce1: common epitope 1. Zinc (Zn-) fingers, GTPase and SH3 and SH3-binding domains also are shown.

The present invention provides a novel mammalian Rb-interacting zinc finger protein, designated RIZ. RIZ is a nuclear phosphoprotein that acts as a cell differentiation factor. RIZ can modulate a function of a cell by binding to retinoblastoma (Rb) protein, which is involved in regulating cell proliferation. In addition, RIZ can act to regulate transcription.

Rb is a nuclear phosphoprotein of 110 kiloDaltons (kD) that can bind DNA and is expressed in all tissue types examined thus far. The complete absence of Rb function is associated with the development of childhood retinoblastoma. In addition, Rb is mutated in a variety of cancer types, including various carcinomas and sarcomas, indicating a role for Rb in oncogenesis. Expression of exogenous Rb in various types of tumor cells suppresses the tumor phenotype (for review, see Lee et. al., J. Cell Biochem. 38:213–227 (1988)).

The function of Rb at the biochemical level in a cell is poorly understood. Rb is present in phosphorylated and unphosphorylated forms in the cell. The phosphorylation status of Rb oscillates during the cell cycle with the hypophosphorylated form correlating with the maintenance of the cell in $G_1$ phase of the cell cycle. Thus, the state of phosphorylation plays an important role in Rb function.

Rb protein binds to several DNA tumor viral oncoproteins, including the adenoviral E1A protein, the SV40 large T antigen and the E7 protein of the human papilloma virus (DeCaprio et al., Cell 54:275–283 (1988); Whyte et al., Cell 56:67–75 (1989); Dyson et al., Science 243:934–937 (1989)). The oncoproteins E1A and large T antigen bind to a similar region of Rb protein known as the Rb pocket, which is formed by two non-contiguous amino acid sequences in the protein (Hu et al., EMBO J. 9:1147–1155 (1990); Huang et al., EMBO J. 9:1815–1822 (1990); Kaelin et al., Mol. Cell. Biol. 10:3761–3769 (1990), each of which is incorporated herein by reference). The binding to Rb by these viral oncoproteins can alter normal Rb function.

Rb also can bind various cellular factors, including, for example, c-Myc and N-Myc (Rustgi et al., Nature 352:541–544 (1991)), E2F (Bagchi et al., Cell 65:1063–1072 (1991)), activating transcription factor-2 (ATF-2; Kim et al., Nature 358:331–334 (1992)), c-Abl (Welch and Wang, Cell 75:779–790 (1993), MyoD (Gu et al., Cell 72:309–324 (1993)) and brahma-related gene-1 (BRG-1; Dunaief et al. Cell 79:119–130 (1994)). Since these cellular factors are involved, for example, in gene regulation and cell differentiation, Rb can have a role in regulating the activity of cell transcription and differentiation factors.

As disclosed herein, RIZ is a normal cellular protein that binds to the Rb pocket. RIZ binding to Rb is unlike that of an oncoprotein since RIZ functions as a differentiation factor that helps to maintain cells in the $G_0$ or $G_1$ phases of the cell cycle. This is based on the fact that RIZ can bind to Rb in the cell, the latter being a known regulator of cell proliferation and differentiation, and that RIZ is structurally related to a known differentiation and transcription factor PRD1-BF1/Blimp-1 (Huang, Cell 78:9 (1994)).

The ability to regulate cell growth has important implications for various human diseases or conditions. Cancer is an example of a disease that results from a breakdown in the ability of a cell to regulate its growth. In contrast, there are examples such as cardiac muscle cells and neural cells where the maintenance of cell growth control contributes to a sustained loss in organ or tissue function following a disease or injury that resulted in cell death. In these situations, the compromised tissue or organ fails to regenerate fully because the remaining live cells are incapable of undergoing proliferation to replace the lost function.

Heart disease provides an example where cardiac muscle cell death due to ischemia or other injury results in a loss of heart function. Generally, proliferation of the remaining live cardiac cells to regenerate the lost cardiac muscle function does not occur in adults. Although myocardial cell proliferation can occur during embryonic and neonatal development, this capacity to proliferate is lost soon after birth. In a similar manner, neural damage resulting from trauma or disease is not usually followed by regeneration of neural function because the remaining neural cells are maintained in the $G_1$ phase of the cell cycle. Transcriptional regulators such as Rb play an important role in controlling whether cells can enter the cell cycle and proliferate. In contrast, inactivation of Rb is involved in the unregulated growth of a cancer cell.

As disclosed herein, RIZ can bind to Rb and can regulate the ability of Rb to maintain cells in the $G_1$ phase of the cell cycle. Methods that affect the ability of Rb and RIZ to associate or that affect the activity of a RIZ can be used to modulate cell proliferation. RIZ can regulate the growth of normal adult cardiac muscle cells by preventing the cells from proliferating following cardiac muscle cell death. RIZ can function to maintain cells in $G_1$ by interacting with Rb through the cr2 domain of RIZ. In addition, the functional differentiation state of a cell, which involves maintenance of a cell in $G_1$, is affected, in part, through the action of other RIZ domains such as the PR domain, GTP binding domain and the zinc finger domains.

Figure 1A-1:
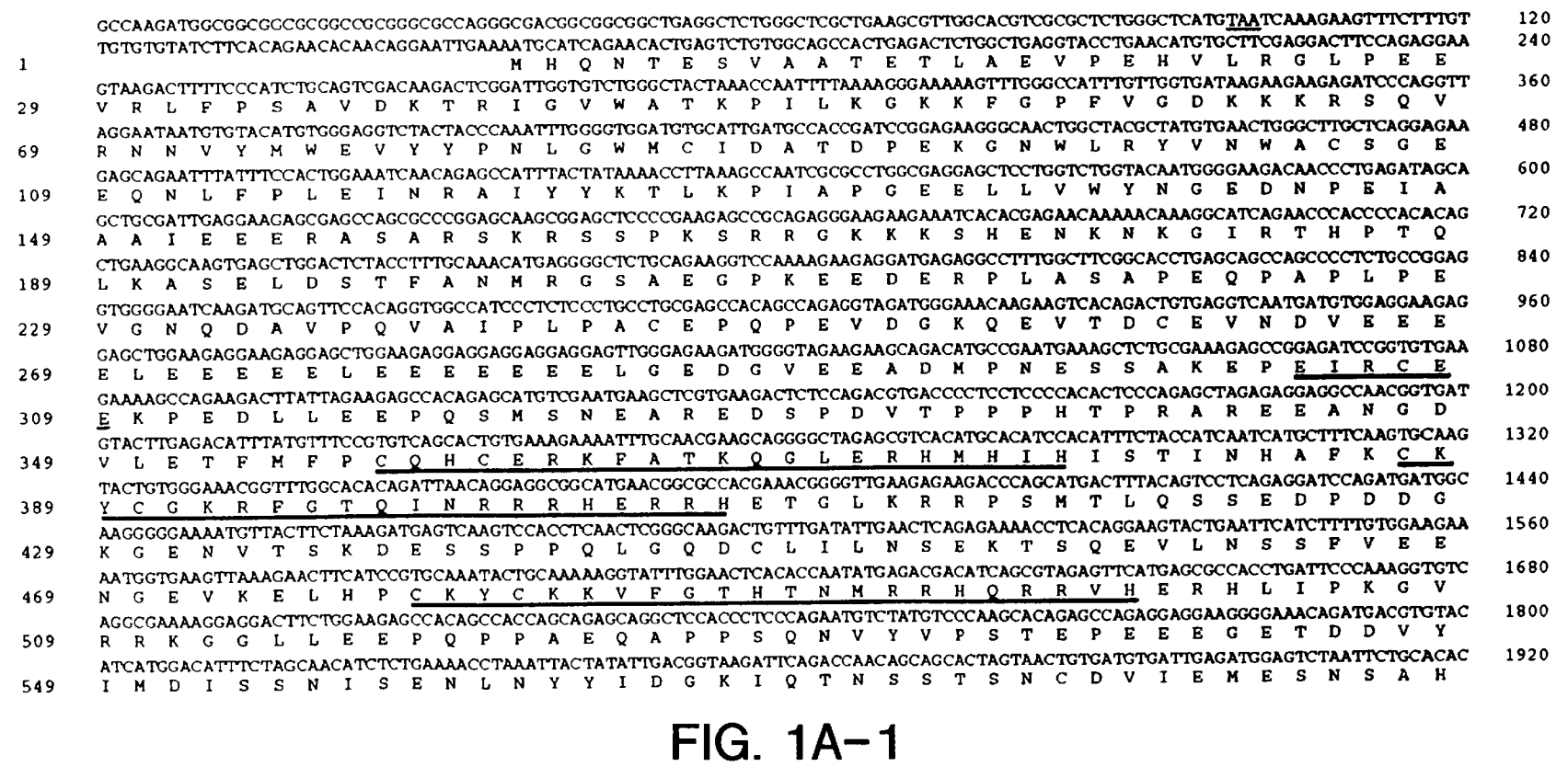

The present invention provides a substantially purified RIZ protein. In a particular embodiment, the invention provides substantially purified mammalian RIZ. The invention provides, for example, human RIZ having substantially the amino acid sequence shown in FIG. 9A (SEQ ID NO: 4) or FIG. 9A with the first three amino acids replaced by SEQ ID NO: 102 or 103 (shown in FIG. 9B), rat RIZ having substantially the amino acid sequence shown in FIG. 1A (SEQ ID NO: 2) and mouse RIZ having substantially the amino acid sequence shown in FIG. 14 (SEQ ID NO: 105).

As used herein, the term "substantially the amino acid sequence" means a sequence that is similar to the disclosed amino acid sequence. For example, an amino acid sequence that is substantially similar to human RIZ (SEQ ID NO: 4) or to rat RIZ (SEQ ID NO: 2) can have one or more amino acid additions, deletions or substitutions that do not substantially alter the ability of the encoded protein to function like a RIZ. In view of this definition, it should be recognized, for example, that the rat RIZ sequence shown in FIG. 1A (SEQ ID NO: 2), which is 84% homologous to the human RIZ sequence has substantially the amino acid sequence of human RIZ (SEQ ID NO: 4). Similarly, the rat RIZ cr2 fragment sequence EIRCEEKPEDL (SEQ ID NO: 6) is substantially the sequence of the human RIZ cr2 fragment sequence, EIRCDEKPEDL (SEQ IN NO: 91). The latter two sequences differ by a single conservative substitution of a Glu in the rat for an Asp in the human in the residue following the Cys.

As used herein, the term "substantially purified" means a protein that is in a form that is relatively free from contaminating lipids, proteins, nucleic acids or other cellular material normally associated with a protein in a cell. A substantially purified human RIZ protein can be obtained, for example, using well known biochemical methods of purification or by expressing a recombinant nucleic acid molecule encoding a RIZ such as the nucleic acid molecule shown as SEQ ID NO: 3. In addition, an amino acid sequence consisting of at least a portion of the amino acid sequence of SEQ ID NO: 4 can be chemically synthesized or can be produced by expressing a portion of the nucleotide sequence shown as SEQ ID NO: 3.

As used herein, the terms "protein" or "polypeptide" are used in the broadest sense to mean a sequence of amino acids that can be encoded by a cellular gene or by a recombinant nucleic acid sequence or can be chemically synthesized. In some cases, the term "polypeptide" is used in referring to a portion of an amino acid sequence encoding a full length protein. An active fragment of a RIZ is an example of such a polypeptide. A protein can be a complete, full length gene product, which can be a core protein having no amino acid modifications, or can be a post-translationally modified form of a protein such as a phosphoprotein, glycoprotein, proteoglycan, lipoprotein or nucleoprotein.

Figure 1A-2:
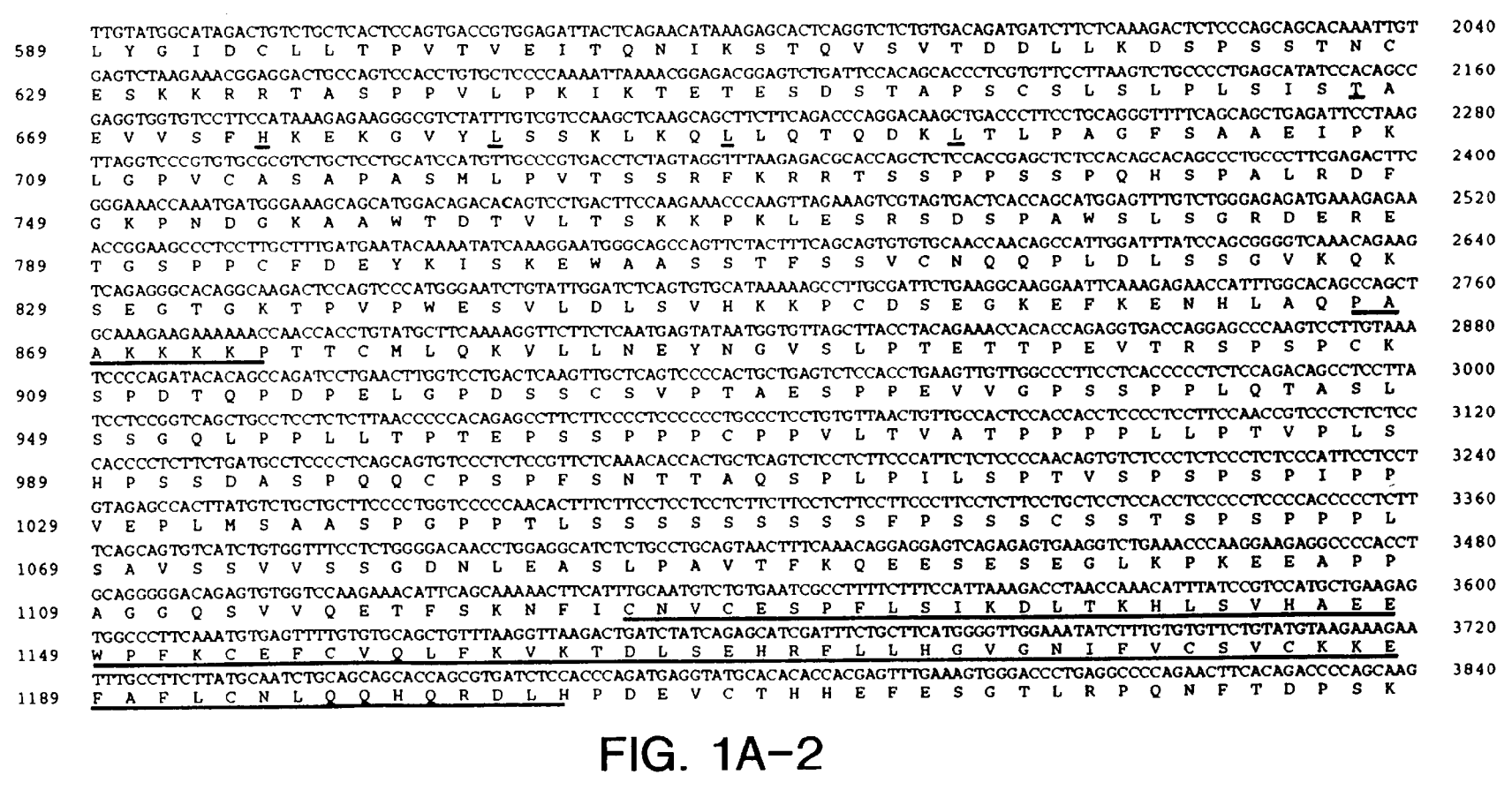
Figure 1A-3:
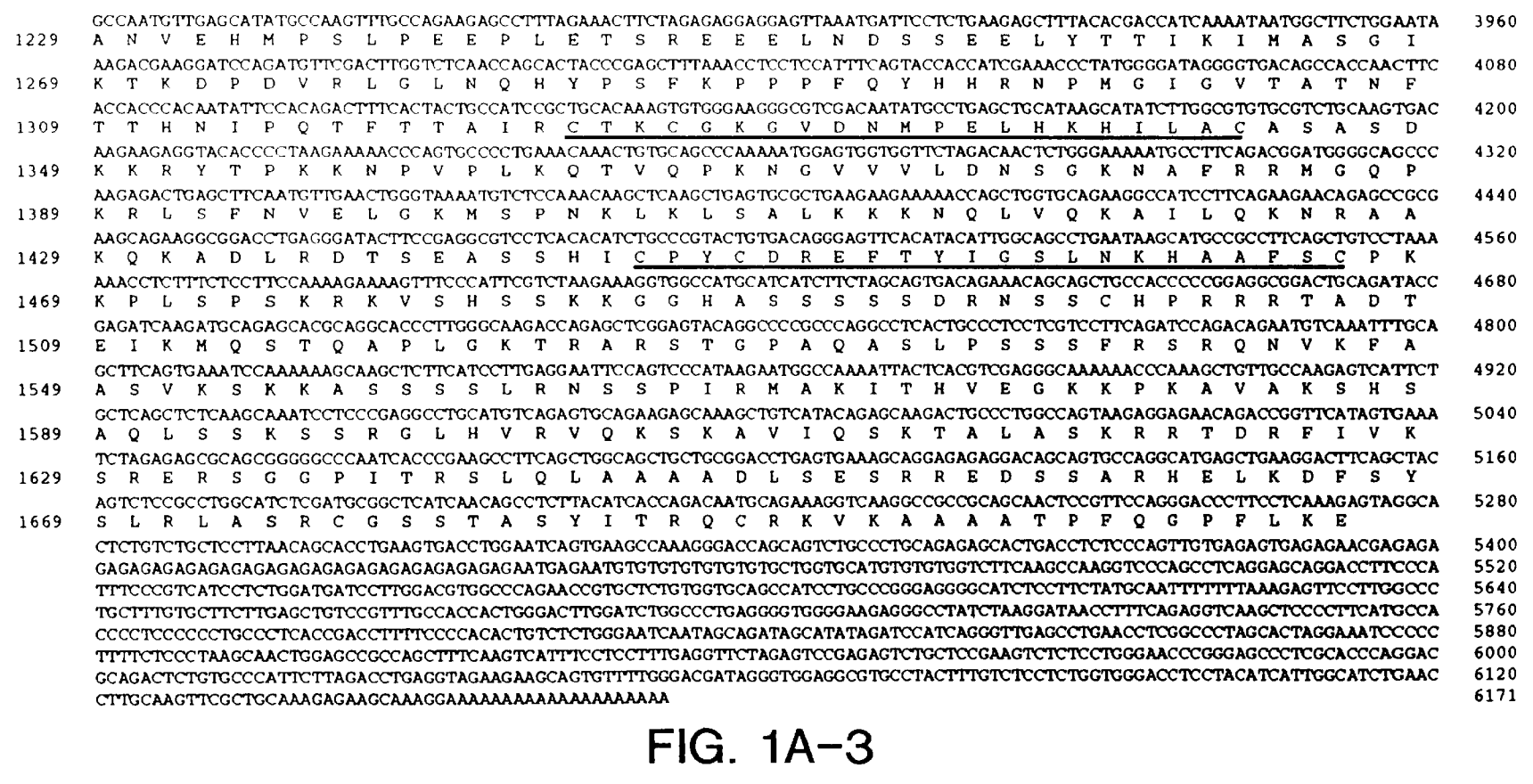

The full length rat RIZ protein contains 1706 amino acids and has a calculated molecular mass of 187,437 Daltons (FIG. 1A; SEQ ID NO: 2). The rat RIZ contains a 6 residue E1A related motif (a.a. position 304–309) known as the cr2 core motif, which is related to the LXCXE (SEQ ID NO: 5) core motif of E1A. Additional E1A related motifs in RIZ include the cr1 motif and a C-terminal motif designated "conserved epitope 1" (ce1) because of its antigenic relationship to a homologous motif in the C-terminus of E1A (see Example II). Rat RIZ also contains 8 zinc fingers, a putative GTPase domain, a putative leucine zipper and a putative nuclear localization signal (FIGS. 1 and 3).

All three E1A-related motifs in rat RIZ are located in an acidic region that consists of about 150 residues (AR; FIG. 3) and resembles a highly acidic region in the E1A 12S protein (Moran and Matthews, Cell 48:177–178 (1987)). In both RIZ and E1A, the related motifs are arranged in the same order and the spacing between cr1 and cr2 is similar. However, the ce1 motif is located much closer to cr2 in RIZ than in E1A (see FIG. 2A).

The rat RIZ protein sequence contains known GTPase motifs (Table 1) organized in an orderly fashion and separated by consensus spacings (Bourne et al., Nature 349:117–127 (1991)). The G1 or Walker type-A motif ($GX_4GKX_7(I/V)$; SEQ ID NO: 14), which represents the phosphate-binding loop (P-loop), occurs at a.a. position 749 in RIZ and identifies a guanine or adenine nucleotide-binding site (Walker et al., EMBO J. 1: 945–951 (1982);

Saraste et al., Trends Biochem. Sci. 15: 430–434. (1990)). The sequence around residue 749 also is similar to the src homology 3 (SH3) domain conserved in many non-receptor tyrosine kinases and other proteins (FIG. 2B panel a); Pawson and Gish, Cell 71:359–362 (1992)). RIZ also contains a proline-rich region that has several potential SH3-binding motifs (FIG. 2B, panel b); Ren et al., Science, 259:1157–1161 (1993)).

TABLE 1

Putative GTPase Domain in RIZ

|  | G1 | G2 | G3 | G4 |
|---|---|---|---|---|
| Consensus | GXXXXGK *(22) | D(X)$_N$T | DXXG (23) | XD (24) |
| RIZ | $^{749}$GKPNDGKA (85) | $^{785}$DERET (86) $^{796}$D(X)$_{12}$T (87) $^{821}$D(X)$_{11}$T (88) | $^{853}$DSEG (89) | $^{912}$TQPD (90) |
| FtsZ |  | $^{106}$GGTGTGAA (25) | $^{122}$DLGILT (26) $^{158}$DSLIT (27) $^{212}$DVRT (28) | $^{180}$DAFG (29) $^{253}$DLSG (30) | $^{295}$TSLD (31) |
| CDC42 | $^{10}$GDGAVGKT (32) | $^{32}$YVPT (33) | $^{57}$DTAG (34) | $^{115}$TQID (35) |
| DOG-SR2 | $^{419}$GVNGVGKS (36) | $^{455}$DT | $^{516}$DTAG (34) | $^{584}$TKFD (37) |
| EF-Tu | $^{13}$GHVDHGKT (38) | $^{50}$D(X)$_{10}$T (39) | $^{80}$DCPG (40) | $^{135}$NKCD (41) |
| Ha-Ras | $^{10}$GAGGVGKS (42) | $^{33}$DPT (43) | $^{57}$DTAG (34) | $^{116}$NKCD (41) |

Comparison of the putative G1–G4 GTPase domains in the RIZ protein sequence with the conserved sequence motifs in the GTPase superfamily (single letter code and X is any residue, Bourne et al., 1991) For reference to the listed sequences (except RIZ and FtsZ) see Bourne et al. (1991) For reference to FtsZ, see RayChaudhuri and Park, Nature 359:251–254, (1992).
*Number in parenthesis below each sequence indicates SEQ ID NO:.

Sequence homology shows that a mammalian RIZ protein contains eight zinc-finger motifs organized as two widely separated clusters in the N-terminal (fingers 1 to 3) and C-terminal (fingers 4 to 6) regions (FIG. 3). A search of the National Biomedical Research Foundation protein database revealed that the most significant homology for zinc fingers was for RIZ fingers 4 to 6, which are about 39% (33 out of 85) identical to fingers 1 to 3 of the human transcriptional repressor PRDI-BF1 (see FIG. 2C; Keller and Maniatis, supra, 1991).

RIZ also contains a region of about 100 residues near the N-terminus that is designated "PR" because it is 42% homologous with a similar N-terminal region from PRDI-BF1 (see FIG. 2C) and Blimp-1 (Huang, supra, 1994). PR, also referred to herein as the "PR domain peptide", is homologous to an N-terminal portion of the mammalian Evi-1 protein (Morishita et al., Cell 54:831–840 (1988); Morishita et al. Oncogene 5:936–971 (1990)) and to an N-terminal portion of the C. elegans egl-43 protein, which is a homolog of Evi-1 (Garriga et al., Genes Devel. 7:2097–2109 (1993); see FIG. 13).

The Evi-1 protein is the product of the ecotropic viral integration site-1 myeloid transforming gene. Aberrant expression of the Evi-1 gene occurs in human acute myelodysplastic leukemia (AML), myelodysplastic diseases (MDS) and chronic myelocytic leukemia (CML), due to translocations or inversions involving chromosome band 3q26 (see, for example, Morishita et al., Proc. Natl. Acad. Sci., USA 89:3937–3941 (1992)). The first 102 amino acids of the Evi-1 protein shown in FIG. 13 (SEQ ID NO: 100), are encoded by nucleotides previously reported to be 5'-untranslated sequence (Morishita et al., supra, 1990); the methionine present in position designated 108 in FIG. 13 (i.e., the 103rd amino acid shown in FIG. 13 for Evi-1) was assigned as the start codon. However, as disclosed herein, designation of an ATG codon further upstream as the start codon elucidates blocks A and B of the PR domain peptide of Evi-1 as shown in FIG. 13 (SEQ ID NO: 100).

Figure 13:
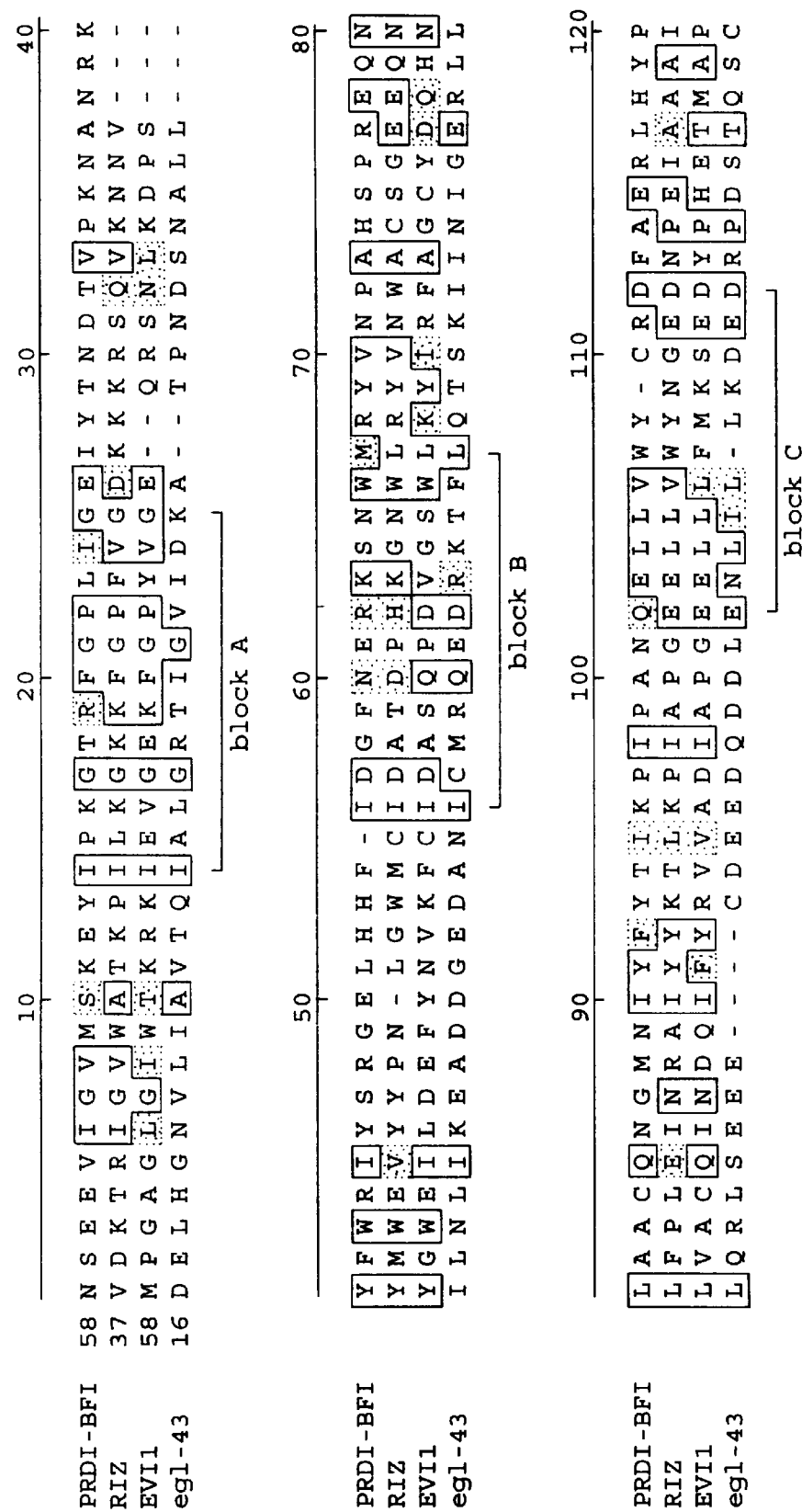
FIG. 13 presents an alignment of the PR domain peptides present in four transcription regulatory proteins. The sequences are aligned so as to maximize homology. A "–" indicates a space introduced to maintain homology. Numbers across the top of the sequences indicates the amino acid number in the PR domain peptide. Numbers at the beginning of each sequence indicate the amino acid position from the N-terminus of each respective protein. Identical or similar residues found at a particular position in at least three of the four peptides are shaded. Identical amino acids at a position in the PR domain peptide are indicated by black shading and conserved regions are indicated by gray shading. "PRDI-BF1" indicates human positive regulatory domain 1-binding factor 1 (SEQ ID NO: 98); "RIZ" indicates human RIZ protein (SEQ ID NO: 99); "EVI1" indicates human ecotropic viral integration site-1 myeloid transforming gene product (SEQ ID NO: 100); "egl-43" indicates the C. elegans egl-43 gene product (SEQ ID NO: 101).

In general, a PR domain peptide is about 100 to about 120 amino acids in length and contains three highly conserved sequences, designated blocks A, B and C, which consist of about 10 to about 12 amino acids, separated by less conserved sequences of about 20 to about 35 amino acids (see FIG. 13). Each of blocks A, B and C for RIZ, Evi-1 and egl-43 are encoded by an individual exon. The PR domain peptides of rat RIZ (a.a. positions 36 to 151; SEQ ID NO: 2) and human RIZ (a.a. positions 37 to 152; see FIG. 13, SEQ ID NO: 99) are identical except that the human RIZ contains a lysine at a.a. position 70, whereas the rat RIZ contains an arginine at the equivalent position (a.a. position 69). Additionally, analysis of a cDNA encoding a portion of the mouse RIZ protein that includes blocks B and C of a PR domain peptide (FIG. 14; SEQ ID NOS: 104 and 105) revealed that the deduced amino acid sequence (i.e. the first 75 amino acids in FIG. 14 (SEQ ID NO: 105) is identical to the corresponding region of the PR domain in human RIZ (i.e. amino acids designated as positions 45–120 for human RIZ in FIG. 13; SEQ ID NO: 99).

The homology among PR domain peptides is evident from inspection of the amino acid sequences shown in FIG. 13 (SEQ ID NOS: 98–101). If conserved amino acid substitutions are considered, the mammalian PR domain peptides (SEQ ID NOS: 98–100) are greater than about 33% homologous to each other over their entire length as shown. Moreover, the highly conserved blocks A, B and C are about 75%, 50% and 55% homologous, respectively, among the three mammalian proteins. In addition, the sequence designated X101, which lies between blocks B and C, is about 38% homologous among the mammalian PR domain peptides shown.

A PR domain peptide can be generally defined by the amino acid sequence, Y-A-X100-B-X101-C-Z, wherein Y is about 8 to 13 independently selected amino acids; X100 is about 20 to 35 independently selected amino acids; X101 is about 20 to 35 independently selected amino acids; Z is about 8 independently selected amino acids; A is Ile-X2-X3-Gly-X4-X5-X6-Gly-X7-X8-X9-X10, wherein X6 is Phe or Ile, X7 is Pro or Val, X10 is Gly or Lys, and X2, X3, X4, X5, X8 and X9 each is one independently selected amino acid, and, preferably, wherein X3 is Lys or Val, X5 is Arg or Lys, X6 is Phe, X7 is Pro, X9 is Ile or Val, and X10 is Gly; B is Ile-X11-X12-X13-X14-X15-X16-X17-X18-X19-X20-X21, wherein X11 is Asp or Cys, X15 is Pro or Glu, X16 is Glu or Asp, X20 is Trp or Phe, X21 is Met or Leu, and X12, X13, X14, X17, X18 and X19 each is an independently selected amino acid, and, preferably, X11 is Asp, X12 is Gly or Ala, X17 is Lys or Val, X18 is Ser or Gly, X19 is Asn or Ser, and X20 is Trp, and wherein C is X22-X23-L-X24-X25-X26-X27-X28-X29-X30-D, wherein X22 is Glu or Gln, X23 is Glu or Asn, X24 is Leu or Ile, X25 is Val or Leu, X30 is Arg or Glu, and X27 and X29 each is an independently selected amino acid, and X26 and X28 each independently is absent or is one amino acid; and, preferably, X23 is Glu, X24 is Leu, X26 is Trp or Phe, X27 is Tyr or Met, and X28, when present, is Asn or Lys.

The present invention provides a PR domain as a component of a transcriptional regulator by operably linking the domains to a peptide that binds to a particular gene promotor or enhancer, wherein binding of the fusion protein to the target gene can alter expression of the target gene. As used herein, the term "transcriptional regulation" includes transcriptional repression and transcriptional activation. Particularly preferred transcriptional regulators containing a PR domain include amino acids 17 to 900 of SEQ ID NO: 2 or 18 to 910 of SEQ ID NO: 4.

The present invention further provides the PR domain or RIZ active fragment containing a PR domain as a probe to identify transcription factors or oncogenic proteins in a cell that bind the PR domain. Methods to detect the interaction between a peptide and another cellular molecule are useful to detect binding between a PR domain and a transcriptional factor or oncogenic protein. Such methods are well known in the art and include, for example, the yeast two hybrid system (Fields and Song, *Nature* 340:245–246 (1989); Vojtek et al., *Cell* 74:205–214 (1993); Durfee et al., *Genes Devel.* 7:555–569 (1993), each of which is incorporated herein by reference). An in vivo transcription activation assay such as the yeast two hybrid system is particularly useful for identifying and manipulating the association of proteins. The results observed using such an assay likely mirror the interactions that naturally occur in a cell. Also, an in vitro assay utilizing, for example, a PR domain fused to GST (see Example II) can provide a simple, rapid and inexpensive method for identifying and isolating an PR domain binding target. Such an in vitro assay is particularly useful for confirming results obtained in vivo.

Figure 9A-1:
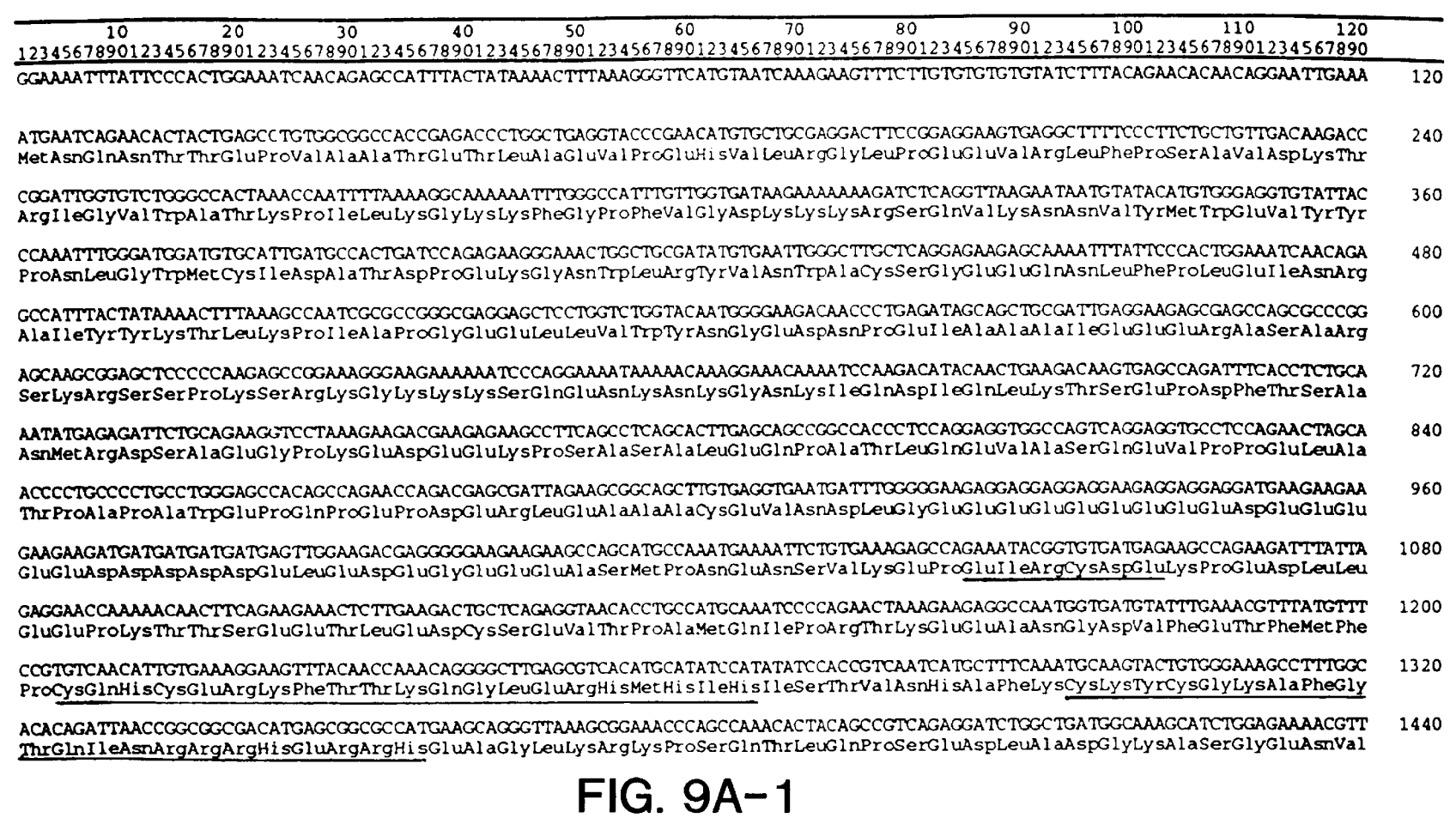
Figure 9A-2:
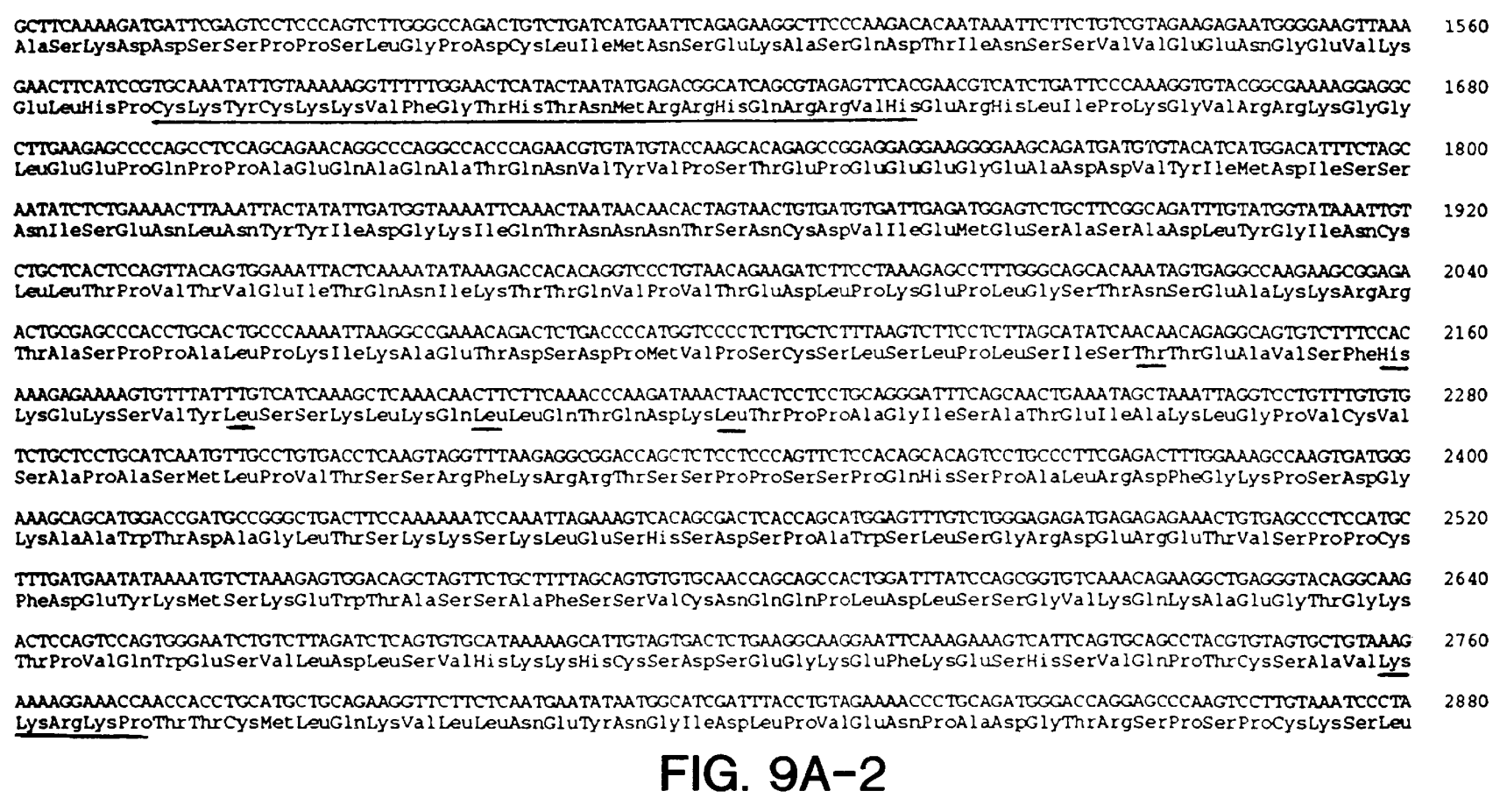
Figure 9A-4:
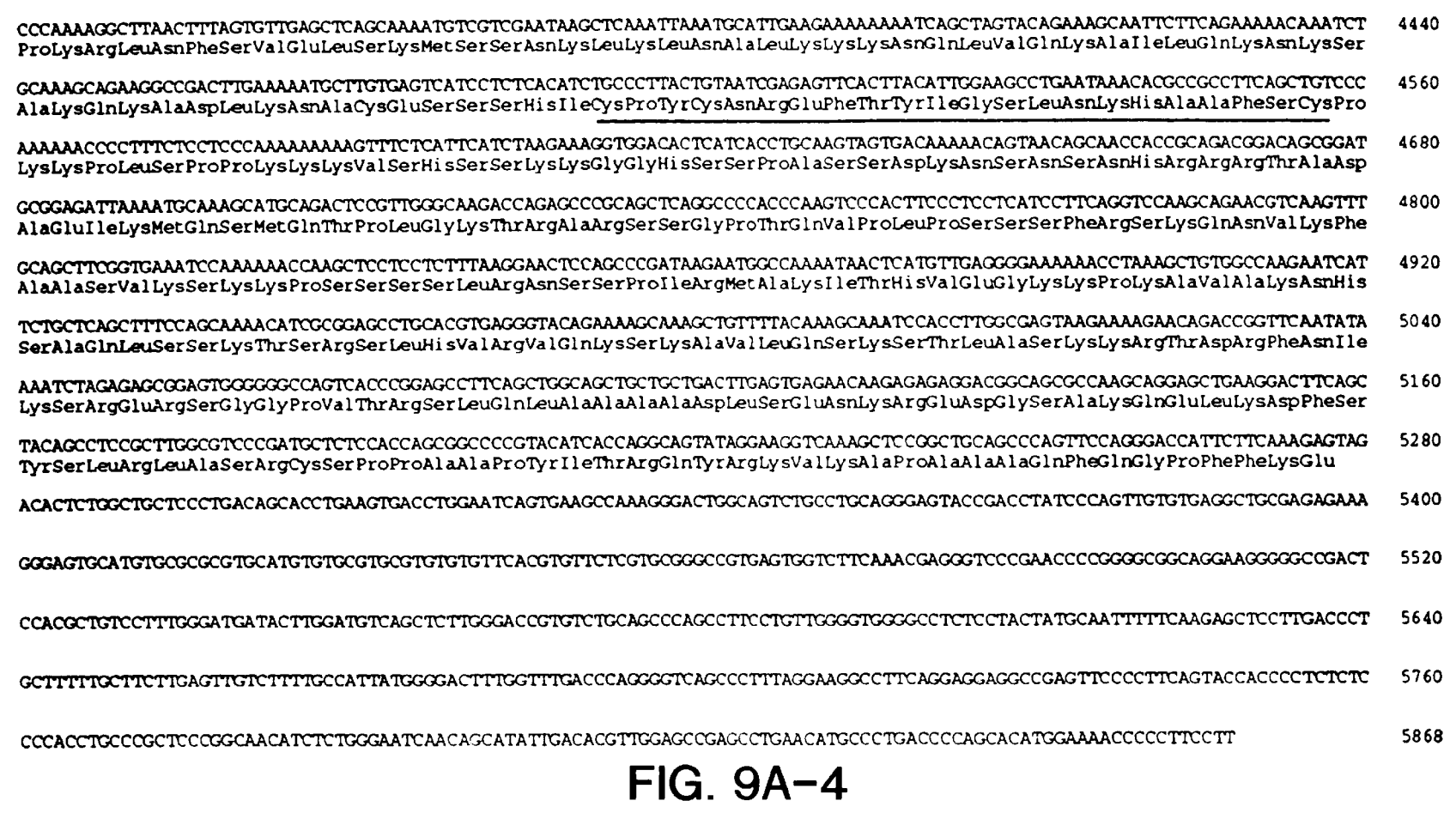

Human RIZ was cloned from human cDNA and genomic DNA libraries using the rat RIZ cDNA as a hybridization probe. A complete human RIZ cDNA sequence is shown in FIG. 9A (SEQ ID NO: 3), which encodes a polypeptide having 1719 amino acid residues (see FIG. 9A; SEQ ID NO: 4). Clones encoding two alternative 5'-termini of human RIZ were also obtained (see FIG. 9B; SEQ ID NOS: 95 and 96).

The human RIZ gene coding region is encoded by eight exons and is located on chromosome 1p36 (see Example VI). Allelic variants of the human RIZ gene are disclosed herein. The RIZ D283 allele contains an Asp residue at a.a. position 283 (SEQ ID NO: 4) while the RIZ E283 allele contains an Glu (See FIG. 9A for the D283 allele). The RIZ D283 allele is estimated to occur two times more frequently in the human population than the RIZ E283 allele. The difference between the two alleles is a T at nucleotide position 969 of FIG. 9A in the RIZ D283 allele (SEQ ID NO: 3) versus an A at the same position in the RIZ E283 allele.

The nucleotides encoding residue 283 of human RIZ (SEQ ID NO: 4) are contained within a region of triplet repeat nucleotides at nucleotide position 952–981 shown in FIG. 9A (SEQ ID NO: 3). The triplet region encoding the D283 allele is $(GAA)_5(GAT)_5$ (designated 5—5) while the E283 allele is $(GAA)_6(GAT)_4$ (designated 6-4). Other alleles or mutations include the $(GAA)_4(GAT)_4$ triplet sequence (designated 4—4) that was detected in one allele of the Malme 3M melanoma cell line and the $(GAA)_7(GAT)_4$ sequence (designated 7-4) that was detected in one allele of SK-MEl-64 and MeWo melanoma cell lines (see Example VI).

The deduced rat (SEQ ID NO: 2) and human (SEQ ID NO: 4) RIZ amino acid sequences are 84% homologous. The rat and human RIZ proteins have similar sequence motifs, including cr1, cr2, ce1, PR, zinc finger, SH3, SH2 and a nuclear localization signal, and are similar in size; rat RIZ (SEQ ID NO: 2) contains 1706 amino acids and has a calculated molecular weight of 187,437 Daltons while a human RIZ (SEQ ID NO: 4) contains 1719 amino acids and has a calculated molecular weight of 188,894 Daltons. A rabbit antiserum produced against rat RIZ (see Example II) cross reacts with human RIZ.

RIZ protein is present primarily in the cell nucleus. RIZ mRNA is expressed primarily in cells of neuroendocrine origin and is expressed in greater amounts in the fetus than in the adult (see FIG. 11). RIZ is expressed in rat cells as a 250 kD phosphoprotein.

As used herein, the term "RIZ" means a protein having substantially the amino acid sequence of human RIZ as shown in FIG. 9A (SEQ ID NO: 4) or of rat RIZ as shown in FIG. 1A (SEQ ID NO: 2). The term "RIZ" is meant to include normal variants such as the 5'-terminus variants of RIZ (see FIG. 9B; SEQ ID NOS: 95 and 96, 102 and 103.) and the allelic variants disclosed herein. Such normal variants can differ in amino acid sequence but share the same or similar functional activities such as binding to GTP, DNA or Rb (see Examples). A RIZ is referred to as a "normal RIZ" or a "wild-type RIZ", all of which are distinct from a mutant RIZ. In addition to the allelic variants, RIZ also can be a truncated RIZ protein encoded by a subset of the RIZ exons and that functions like a RIZ. Such a variant RIZ can be generated in the cell by alternative RNA splicing, which may be responsible for the three 5'-terminus variants of human RIZ (see FIG. 9A and 9B; SEQ ID NOS: 3, 4, 95, 96, 102 and 103).

The term "RIZ" also includes peptide fragments of a RIZ, including active fragments of a RIZ. As used herein, the term "active fragment" means a peptide portion of a full length RIZ protein that has at least one activity that is characteristic of the corresponding full length protein. A peptide portion of a rat RIZ having the sequence EIRCEEKPEDL (SEQ ID NO: 6) or a peptide portion of a human RIZ having the sequence EIRCDEKPEDL (SEQ ID NO: 91) are examples of active fragments of a RIZ that can bind to Rb. In addition, peptide portions of a RIZ containing a PR domain, for example, a.a. positions 36 to 151 of rat RIZ (SEQ ID NO: 2) or a.a. positions 37 to 152 of human RIZ (SEQ ID NO: 4; see, also, SEQ ID NO: 99), are examples of an active fragment of a RIZ protein, which may interact with transcription factors and can be involved in regulating transcription. In some cases, an active fragment of a RIZ protein is active only when present in the nucleus. In such a case, the active fragment can contain a nuclear localization signal such as that contained at a.a. positions 880 to 884 of human RIZ (SEQ ID NO: 4) or at positions 867 to 874 of rat RIZ (SEQ ID NO: 2). The nuclear localization signal is another example of an active fragment of a RIZ. Other RIZ activities that can be associated with an active fragment of a RIZ include the ability to bind DNA in a zinc ion-dependent manner, the ability to bind GTP or an anti-RIZ antibody, or the ability to act as a hapten or immunogen to obtain an anti-RIZ antibody.

The present invention provides active fragments of a RIZ, such as EIRCEEKPEDL (SEQ ID NO: 6), or EIRCDEKPEDL (SEQ ID NO: 91), which contain substantially the amino acid sequence of the RIZ cr2 core motif, where the cysteine residue is required when the activity of the fragment is Rb binding. The cr2 core-motif containing fragments of human RIZ or rat RIZ are examples of active fragments of a RIZ. Such active fragments can be produced by recombinant DNA methods, by peptide synthesis or by enzymatic cleavage of a RIZ protein. The present invention also provides a non-naturally occurring polypeptide having incorporated therein a RIZ cr2 core motif. Such a polypeptide can be produced, for example, using well known recombinant DNA methods or by peptide synthesis.

A RIZ protein or a RIZ polypeptide containing a cr2 sequence such as the amino acid sequences EIRCEEKPEDL (SEQ ID NO: 6) and EIRCDEKPEDL (SEQ ID NO: 91) can bind to Rb and, therefore, is useful for isolating Rb from a sample. Purified Rb can be used, for example, as a control target in a diagnostic test to detect whether a subject has a mutated Rb. Additionally, Rb can be used to as a reagent to detect whether a sample has a RIZ which can bind to Rb or a mutant RIZ that fails to bind Rb. Mutations that affect the function of Rb and are diagnostic for cancer are well known in the art (see, for example, Lee et al., In *Tumor Suppressor Genes*, Chapter 11, Marcell Decker (1990).

To purify Rb, RIZ protein can be contacted with the Rb containing sample under suitable conditions, which allow formation of a RIZ-Rb complex. Suitable conditions for complex formation can be determined empirically and include, for example, an appropriate buffer concentration and pH and time and temperature of incubation that permit binding of the RIZ to Rb. The RIZ-Rb complex can be separated from unbound material in the sample and Rb can be dissociated from the complex and obtained in substantially purified form.

Substantially purified Rb can be obtained, for example, by using affinity chromatography, in which a RIZ is bound to a solid support, the sample is applied to the support to allow binding of Rb to the RIZ, the support is washed to remove unbound material and Rb is eluted from the support. Useful solid supports include, for example, agarose, Sepharose™ or plastic. RIZ can be attached to a solid support by direct chemical coupling or by an indirect means such as an affinity interaction with an anti-RIZ antibody bound to the support. Other indirect means for coupling a RIZ to a support include incorporating one entity of a known ligand/receptor pair into the RIZ, with the corresponding entity coupled directly to the support. For example, biotin can be coupled to RIZ and avidin can be coupled directly to a solid support to bind the RIZ to the support. Also, RIZ can be expressed as a fusion to glutathionine S-transferase (see Example II) and the fusion protein can be bound to a glutathionine coupled support.

The present invention also provides a RIZ binding reagent. As used herein the phrase "RIZ binding reagent" means a chemical or biological molecule that specifically binds to a RIZ. As used herein with reference to a RIZ, the term "specifically binds" means that under a defined set of conditions, the RIZ binding reagent interacts with a RIZ but not with an unrelated molecule or with a mutant RIZ. Rb and anti-RIZ antibody are examples of a RIZ binding reagent.

The invention also provides a mutant RIZ binding reagent. As used herein, the phrase "mutant RIZ binding reagent" means a chemical or biological molecule that specifically binds to a mutant RIZ but not to a wild-type RIZ. In this case, the mutant RIZ binding reagent, under a defined set of conditions, interacts with the mutant RIZ but not with a wild-type RIZ.

Rb and an antibody specific for a RIZ are examples of reagents that can specifically bind to a RIZ. As used herein, the term "antibody" is used in its broadest sense to include polyclonal and monoclonal antibodies, as well as polypeptide fragments of antibodies that retain a specific binding activity for a specific antigen of at least about $1 \times 10^5$ $M^{-1}$. One skilled in the art would know that a fragment such as Fab, F(ab')$_2$, Fv and Fd fragments of an anti-RIZ antibody, for example, can retain specific binding activity for a RIZ and, thus, is included within the definition of an antibody. In addition, the term "antibody" as used herein includes naturally occurring antibodies as well as non-naturally occurring antibodies and fragments of antibodies that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference.

An antibody specific for a RIZ can be prepared using well known methods as described, for example, by Harlow and Lane, *Antibodies: A laboratory manual* (Cold Spring Harbor Laboratory Press, 1988), which is incorporated herein by reference. For example, RIZ protein or a portion of the RIZ protein can be used as an immunogen, which can be prepared from natural sources or produced recombinantly or, in the case of a portion of the RIZ protein, can be chemically synthesized. Non-immunogenic peptides of RIZ protein can be made immunogenic by coupling to a carrier molecule such as bovine serum albumin or keyhole limpet hemocyanin as described, for example, by Harlow and Lane, supra, 1988. In addition, a RIZ fusion protein can be expressed as described in Example II. Such a fusion protein can be readily purified and used as an immunogen (see Example II). These methods can be used to produce various anti-RIZ antibodies.

Polyclonal antibodies can be raised, for example, in rabbits or goats. In addition, monoclonal antibodies can be obtained using well known methods (see, for example, Reed et al., *Anal. Biochem.* 205:70–76 (1992)), which is incorporated herein by reference; see, also, Harlow and Lane, supra, 1988). For example, spleen cells from a RIZ immunized mouse can be fused to an appropriate myeloma cell line such as SP2/0 or P3×653.Ag8 myeloma cells to produce hybridoma cells. Cloned hybridoma cell lines can be screened using a labeled RIZ immunogen to identify clones that secrete monoclonal antibodies. Hybridomas that express antibodies having a desirable specificity and affinity can be isolated and utilized as a continuous source of antibodies. A dependable source of monoclonal antibodies is desirable, for example, for preparing diagnostic kits as described below.

An antibody specific for a mutant RIZ protein also can be prepared using the above methods by immunizing with either the full-length mutant RIZ protein or with a fragment of the protein containing the mutation. Methods to direct the immune response to the mutant sequence also are well known in the art and include, for example, use of particular adjuvants or pre-prior tolerization of the animal to the wild-type RIZ sequence. Such tolerization can be performed by immunizing the animal with the wild-type RIZ in conjunction with administration of anti-T cell antibodies or immunosuppressive drugs. A monoclonal antibody to the mutant sequence can be obtained by screening a population of hybridomas for those that express an antibody that binds the mutant RIZ sequence but not a wild-type RIZ sequence.

The invention also provides a substantially purified nucleic acid molecule, which encodes a RIZ such as a mammalian RIZ. For example, the invention provides substantially purified nucleic acid molecules having substantially the nucleotide sequences encoding human RIZ (FIG. 9A; SEQ ID NO: 3) and rat RIZ (FIG. 1A; SEQ ID NO: 1), including nucleotide sequences having alternative 5'-nucleotide sequences for human RIZ (FIG. 9B; SEQ ID NOS: 95 and 96) and rat RIZ (FIG. 1B; SEQ ID NO: 94). The cDNA sequence encoding human RIZ shown in FIG. 9A (SEQ ID NO: 3) includes further 3' untranslated sequence, a portion of which is shown in FIG. 9C (SEQ ID NO: 97). In addition, the invention provides substantially purified nucleic acid molecules encoding mouse RIZ that incldue substantially the nucleotide sequence shown in FIG. 14 (SEQ ID NO: 104).

As used herein, the term "substantially purified nucleic acid molecule" means a nucleic acid molecule that is in a form that is relatively free from contaminating lipids, proteins, nucleic acids or other cellular material normally associated with a nucleic acid molecule in a cell. A substantially purified nucleic acid molecule can be obtained, for example, by recombinant DNA methods as described herein (see, also, Sambrook et al., *Molecular Cloning: A laboratory manual* (Cold Spring Harbor Laboratory Press 1989), which is incorporated herein by reference) or can be chemically synthesized.

As used herein with reference to a RIZ, the term "substantially the nucleotide sequence" means, for example, the disclosed nucleotide sequences for human RIZ (SEQ ID NOS: 3, 95 and 96), as well as similar sequences that contain, for example, different nucleotides than shown in SEQ ID NOS: 3, 95 and 96, but that, as a result of the degeneracy of the genetic code, encode the same amino acid sequence as shown in SEQ ID NOS: 4, 102 and 103, respectively. In addition, the rat RIZ nucleotide sequences (SEQ ID NOS: 1 and 94) and the mouse RIZ nucleotide sequence (SEQ ID NO: 104) that corresponds to the rat RIZ sequence are considered to be substantially similar to the nucleotide sequence encoding human RIZ (SEQ ID NO: 3). For convenience, the coding strand for a nucleic acid molecule encoding a RIZ is shown. It should be recognized, however, that the complementary strand also is encompassed within the disclosed nucleic acid molecules. Thus, unless otherwise indicated, reference herein to a nucleic acid molecule or to a nucleotide sequence is meant to include the complementary sequence.

A nucleic acid molecule of the invention can encode a variant RIZ such as the allelic RIZ variants disclosed herein as well as variants of a RIZ that contain only particular exons of the gene that can be produced in a cell by alternative RNA splicing. In addition, a nucleic acid molecule of the invention can encode a portion of a RIZ such as an active fragment of a RIZ containing the polypeptide EIRCEEKPEDL (SEQ ID NO: 6) and EIRCDEKPEDL (SEQ ID NO: 91), which binds to the Rb pocket or a RIZ fragment containig a PR domain peptide (see, for example, FIG. 13; SEQ ID NOS: 98–101), which may bind to a transcription factor and be involved in transcriptional regulation.

The invention also provides a nucleotide sequence that specifically hybridizes to a portion of a nucleic acid molecule encoding a mammalian RIZ under relatively stringent hybridization conditions. As used herein with reference to a RIZ, the term "specifically hybridizes" means that under a defined set of hybridization conditions, the nucleotide sequence can interact with a RIZ encoding nucleic acid molecule but not with an unrelated nucleic acid molecule. A nucleotide sequence that specifically hybridizes to a RIZ can be complementary to a nucleotide sequence encoding a RIZ or can be a RIZ coding sequence or a portion thereof.

A nucleotide sequence that specifically hybridizes to a nucleic acid molecule encoding a RIZ or a mutant nucleic acid molecule encoding a RIZ should be at least ten nucleotides in length and can be prepared, for example, by restriction endonuclease digestion of a cloned nucleic acid molecule encoding a RIZ or by PCR amplification of a portion of the nucleic acid molecule shown in FIG. 1A or 1B (SEQ ID NOS: 1 and 94) or FIG. 9A, 9B or 9C (SEQ ID NOS: 3, 95, 96 and 97), or by chemical synthesis. A nucleotide sequence that can hybridize to one or more of the nucleotide sequences encoding the highly conserved block A, B or C of a RIZ PR domain peptide (see FIG. 13) can be particularly useful, for example, to identify nucleic acid molecules that encode other members of PR domain peptide-containing family of proteins.

Relatively stringent hybridization conditions can be determined empirically or can be estimated based, for example, on the relative GC:AT content of the hybridizing nucleotide sequence and the target sequence, the length of the hybridizing nucleotide sequence and the number, if any, of mismatches between the hybridizing nucleotide sequence and the target sequence. If desired, a hybridizing nucleotide sequence can be detectably labeled and used as a probe or can be used as a primer for PCR. Methods for detectably labeling a nucleotide sequence are well known in the art (see, for example, Sambrook et al., supra, 1989; see, also, Ausubel et al., *Current Protocols in Molecular Biology* vol. 2, chapter 10 (Greene Publ., NY 1989), which is incorporated herein by reference).

As used herein, the term "mutant nucleic acid encoding a RIZ" includes nucleic acid molecules having a mutation in an exon, thus encoding a mutant RIZ protein, as well as nucleic acid molecules having a mutation in a region of the RIZ gene other than the exons. A mutation in the RIZ gene occurring outside the exons can involve a regulatory element of the gene that modulates the expression of the RIZ in a cell. Such regulatory elements that can be mutated include, for example, the promoter, enhancer, ribosomal binding site or intron-exon splice junctions. The term "mutant RIZ" also includes peptides of a mutant RIZ, including active fragments of a mutant RIZ.

A mutation that occurs in a regulatory element of the RIZ gene can have a significant impact on the level of expression of a RIZ in a cell. In addition, a mutation in a RIZ exon that codes for a stop codon within the reading frame of the RIZ can produce a truncated RIZ that may be inactive, have an altered activity or be subject to rapid proteolysis in the cell. Similarly, a deletion involving a substantial portion of the gene encoding the RIZ can result in a loss of RIZ expression.

As used herein, the term "mutant RIZ" includes any RIZ having a mutation in a RIZ exon that results in the expression of a RIZ having a functional activity differing from that of a wild-type RIZ normally expressed by a cell. A change in a functional activity characteristic of a mutant RIZ can result from one or more amino acid additions, deletions or substitutions in the wild-type RIZ sequence. Such mutations can arise spontaneously or can be resident in the population and inherited from generation to generation as occurs, for example, with Rb. A mutant RIZ can have a change in the nucleotide at position 437 of FIG. 9A in human RIZ (SEQ ID NO: 3)from a G to an A, which results in the expression of mutant RIZ having a Tyr residue instead of a Cys residue at a.a. position 106 (SEQ ID NO: 4).

The present invention also provides a nucleotide sequence that specifically hybridizes to a mutant nucleic acid molecule encoding a RIZ under relatively stringent conditions but not to a wild-type RIZ. In this case, the hybridizing sequence should be complementary to a portion of the RIZ gene containing the mutation.

The expression of a particular RIZ allele can be altered in a cancer cell due to a mutation in the RIZ gene. As disclosed herein, some melanoma tumor cells fail to express mRNA encoding one of two RIZ gene alleles present in the cells (see Example VI). The unexpressed allele likely contains a mutation outside the RIZ coding sequence that affects RIZ expression. Detection of such mutations through the RIZ protein or the RIZ gene can be diagnostic of a pathology such as a cancer.

A mutant RIZ can be obtained, for example, by site directed mutagenesis of a nucleic acid molecule encoding a RIZ, then screening the mutagenized nucleic acid molecule to identify an encoded mutant RIZ. Mutations that affect a functional activity of a RIZ such as Rb binding, DNA binding or GTP binding can be detected by screening for mutants that have lost such activities. Expression in a cell of a mutant RIZ such as mutant human RIZ, which can bind Rb, for example, but lacks another RIZ activity, can alter the association of wild type RIZ with Rb and can affect a function of a cell such as the ability of the cell to proliferate.

The ability of a RIZ to be expressed in the nucleus together with its ability to bind DNA, Rb and GTP (see Example II and IV) and its homology with Blimp-1 (PRD1-BF1) differentiation factor indicates that RIZ can function as a transcriptional regulatory protein or cell differentiation factor. Thus, a function of a cell can be modulated by expressing a RIZ in a cell, where the expressed RIZ can bind to Rb and to DNA in the cell. Cell function can also be modulated through the ability of the complete RIZ protein or an active fragment of RIZ containing the PR domain peptide to act as a transcriptional regulator (see Example VII).

As used herein, the term, "a function of a cell" means a cell activity, including, for example, proliferation and differentiation. As used herein, the term "modulate" means increase or decrease. As disclosed herein, the function of a cell can be modulated due to an altered level of expression of a RIZ or expression of a mutant RIZ in a cell.

The present invention provides methods for modulating a function of a cell by expressing in the cell a DNA sequence encoding a RIZ or an active fragment of a RIZ. Such a DNA sequence can be expressed by introducing into a host cell an appropriate expression vector having gene regulatory elements operably linked with the RIZ encoding nucleotide sequence. The expression vector can provide constitutive expression of the polypeptide or, if desired, inducible expression. Expression vectors having the appropriate gene regulatory elements can be purchased from commercial sources or can be constructed using well known methods. For therapeutic purposes, cells can be transfected in tissue culture, then administered to a subject, or a viral vector can be used to introduce a RIZ encoding nucleic acid into a cell in a subject.

Because the transcriptional activity of RIZ requires localization of RIZ to the cell nucleus, active fragments of RIZ can, depending on the size of the fragment, require inclusion of a nuclear localization signal. For example, a RIZ active fragment can include the nuclear localization signal endogenous to rat RIZ at a.a. position 867–874 (SEQ ID NO: 2) or human RIZ at a.a. position 880–884 (SEQ ID NO: 4). Alternatively, the nuclear localization signal included in the RIZ active fragment can be derived from a non-RIZ protein. A variety of nuclear localization sequences are known in the art that can direct proteins to the cell nucleus (see for example, Dingwall et al. *EMBO J.* 8:69–71 (1987), which is incorporated herein by reference).

As disclosed herein, RIZ can regulate the growth of normal adult cardiac muscle cells and prevent proliferation of surviving cells following cardiac muscle cell death. RIZ can function to maintain cells in the $G_1$ phase of the cell cycle by interacting with Rb through the cr2 domain of RIZ. In addition, the functional differentiation state of a cell, which involves maintenance of a cell in the $G_1$ phase of the cell cycle can be affected through the action of other RIZ domains such as the GTP binding domain and the zinc finger domains.

The regeneration of cardiac muscle cells can be promoted in a subject with cardiac damage by directly decreasing the activity of a RIZ or by decreasing the activity of Rb that occurs subsequent to RIZ binding. The activity of a RIZ can be decreased in such cells by introducing into the cells an expression vector having an expression control sequence operatively linked to a nucleotide sequence encoding a mutant RIZ polypeptide or an active fragment that can bind to Rb but lacks the growth suppressing properties of RIZ. The sequences EIRCEEKPEDL (SEQ ID NO: 6) and EIRCDEKPEDL (SEQ ID NO: 91) are examples of such a peptide.

As used herein, the term "growth suppressing properties of RIZ" means the ability of RIZ to effect the differentiation and the maintenance of cells in $G_1$. In fact, the cell may be in an extended $G_1$ phase or a $G_0$ phase or may be blocked at the $G_0/G_1$ boundary. For convenience, any such cells are referred to as being maintained or suppressed in $G_1$. The growth suppressing or differentiating properties of a RIZ can be mediated by regions of the molecule outside the cr2 domain or in conjunction with cr2 that is involved in binding to the Rb pocket.

Neurons, like myocardial cells, normally do not proliferate in the adult. RIZ is preferentially expressed in neural cells (see Example V), indicating a role for RIZ in mediating $G_1$ suppression and differentiation of these cells. The ability to induce proliferation in neural cells can be useful for healing after injury of neural tissue treating neurodegenerative diseases such as Parkinson's disease, Huntington's disease or Alzheimer's disease or paralysis or motor neuron disorders. Thus, the disclosed methods for decreasing the activity of a RIZ protein in a muscle cell similarly can provide a therapy for a neurodegenerative disease.

As disclosed herein, the RIZ gene is in chromosome band 1p36; therefore, mutations in the nucleotide sequence encoding a RIZ can be involved in the development of cancer, particularly cancers such as melanoma, neuroblastoma, leukemia, and breast cancers known to be associated with deletions or rearrangements involving 1p36. Melanoma cells can show a reduction or absence of expression of a RIZ allele and, a reduction in the overall amout of RIZ protein expressed in the cell. These results indicate that melanoma can be characterized by a reduced level of RIZ protein and, thus, a reduced level of RIZ function, which may explain the selective growth advantage of melanoma tumor cells that occurs following alterations in distal chromosomal 1p (Dracopoli et al., *Proc. Natl. Acad. Sci., USA* 86:4614–4618 (1989)). Mutations in distal chromosome 1p that affect the level of expression of RIZ may be responsible for the increased risk of melanoma observed in survivors of heritable retinoblastoma, which occurs without homozygous inactivation of the Rb gene. Since Rb binds to RIZ, a decreased level of Rb-RIZ complex in a tumor cell, resulting from a reduced expression of a RIZ allele, can result in a loss in Rb tumor suppressor activity in the cell without Rb mutation.

Further support for the loss of RIZ function and the development of cancer is provided by the disclosure that RIZ is a differentiation factor. As such, a mutant RIZ can affect the regulation of cell growth by binding to the Rb pocket, a site in the Rb molecule that is involved in regulating cell proliferation. Thus, the present invention provides methods for restoring normal cell growth to a cancer cell that has a mutated or missing RIZ allele by expressing a normal RIZ protein in the cell. As shown in Example VI, increasing the expression of RIZ in a tumor cell by transfecting the cell with a RIZ expression vector results in decreased cell growth.

The disclosure that RIZ can modulate a function of a cell by binding to a second molecule such as Rb or a nucleic acid such as DNA or RNA provides a means to identify agents that can effectively alter the association of a RIZ with a second molecule in a cell and, as a result, modulate a function of a cell. Thus, the present invention provides a screening assay useful for identifying an effective agent, which can alter the association of a RIZ with a second molecule. A second molecule that binds to a RIZ can also be a transcription factor or an oncogenic protein. Such second molecules can bind to the PR domain of RIZ.

An effective agent that can decrease the association of a RIZ with a second molecule such as Rb or that can decrease the activity of a RIZ can be useful for releasing a cell from Rb-mediated $G_1$ arrest. Alternatively, an effective agent that increases the association of a RIZ with a second molecule such as Rb or DNA or increases the activity of a RIZ can be useful for reducing the unrestricted growth of a cancer cell by providing a stronger $G_1$ arrest signal in the cell.

A nucleotide sequence that specifically binds to a RIZ can be detected by using methods well known in the art (see for example, El-Deiry et al., *Nat. Genet.* 1:45 (1992), which is incorporated herein by reference). Genomic DNA can be processed, for example, by sonication to produce uniform-sized fragments, which can be screened for the ability to bind to a RIZ. Genomic DNA sequences that bind to a RIZ can be isolated using, for example, an anti-RIZ antibody and Protein A affinity chromatography. The isolated DNA sequences can be amplified by PCR, which can be facilitated by ligating the original genomic DNA fragments to "catch linkers" (El-Deiry et al., supra, 1992) suitable for annealing to PCR primers.

Random oligonucleotides consisting of at least about ten nucleotides and including "catch linkers" also can be screened to identify sequences that can bind a RIZ. For example, RIZ protein can be immobilized to a filter, then incubated with the oligonucleotides under conditions that allow the RIZ to bind relatively specifically to a RIZ binding sequence. Unbound oligonucleotides can be washed from the filter, then specifically bound sequences can be eluted and amplified by PCR. Following three or more cycles of binding, elution and amplification, a consensus RIZ binding sequence can be obtained. If desired, the consensus RIZ binding sequence can be used to screen a genomic DNA library to obtain genomic DNA sequences containing the RIZ binding sequence.

An agent can be a chemical or biological molecule such as a simple or complex organic molecule, a peptide, a peptido-mimetic, a protein, a carbohydrate or an oligonucleotide that has the potential for altering the association of a RIZ with a second molecule or altering an activity of a RIZ. With reference to a RIZ, the term "effective agent" means an agent that can, in fact, alter the association of RIZ with a second molecule or can alter the activity of a RIZ.

An effective agent can be, for example, a nucleic acid molecule that encodes a RIZ or a mutant RIZ or is complementary to a RIZ- or mutant RIZ-encoding nucleotide sequence. Such nucleic acid molecules can be contained within an expression vector having the RIZ encoding sequence operably linked to an expression control sequence. An effective agent also can be an antisense RIZ or a ribozyme complementary to a RIZ mRNA sequence. Such agents can reduce the level of expression of a RIZ in a cell and, as a consequence, can alter the amount of a RIZ that is associated with a second molecule in a cell.

As used herein with reference to a RIZ, the term "alter the association" means that the association of a RIZ and a second molecule either is increased or is decreased due to the presence of an effective agent. As a result of an altered association of RIZ with a second molecule in a cell, the activity of the RIZ or second molecule can be increased or decreased, which can modulate a function of a cell. As used herein with reference to a RIZ, the term "alter the activity" means that the effective agent can increase or decrease the activity of RIZ in a cell, such as by altering the association of a RIZ with the second molecule as described above by modifying, for example, an activity of a RIZ that occurs consequent to binding a second molecule.

An effective agent that alters the association of a RIZ with a second molecule can interfere with the ability of the RIZ and the second molecule to associate or can cause the dissociation of a bound RIZ-second molecule complex. In the presence of an effective agent, the association of a RIZ with a second molecule can be altered, which can alter the activity of the RIZ or the second molecule in the cell. As a result of the altered activity, a cell function such as the ability of a cell to proliferate can be modulated. Thus, the identification of an effective agent that alters the association of a RIZ with a second molecule provides a means to modulate cell proliferation.

An effective agent that alters the association of a RIZ and Rb can be useful as a medicament to treat a pathology characterized, in part, by excessive cell growth such as occurs in a cancer or by insufficient cell growth such as occurs in a tissue that fails to regenerate in response to cell death. A peptide having the sequence EIRCEEKPEDL (SEQ ID NO: 6) or EIRCDEKPEDL (SEQ ID NO: 91), which contains the cr2 core motif of RIZ, is an example of an effective agent. Either of the peptides can alter the association between a RIZ and Rb (see Example II) and can induce cells such as adult cardiac muscle cells or adult neural cells to proliferate, which can regenerate heart function or neural function, respectively, following injury or disease.

The present invention also provides in vitro screening assays to detect an effective agent. Such screening assays are particularly useful in that they can be automated, which allows for high through-put screening, for example, of randomly or rationally designed agents such as drugs, peptido-mimetics or peptides in order to identify agents that effectively alter the association of a RIZ and a second molecule or modulate a function of a cell.

An in vitro screening assay can utilize, for example, RIZ or a RIZ fusion protein such as a glutathione-S-transferase-RIZ fusion protein (GST-RIZ; see Example II). For in vitro screening assays, the RIZ or RIZ fusion protein can be attached to a solid substrate, provided the attached RIZ maintains the ability to associate with a particular second molecule. For example, when human RIZ is used in the assay, the solid substrate can contain a covalently attached anti-RIZ antibody to bind RIZ to the substrate (see Example II). Alternatively, a GST-RIZ fusion protein can be used in the assay and the solid substrate can contain covalently attached glutathione, which is bound by the GST component of the GST-RIZ fusion protein. Similarly, a second molecule or a GST-second molecule fusion protein can be used in an in vitro assay as described herein.

An in vitro screening assay can be performed by allowing, for example, a RIZ or RIZ-fusion protein to bind to the solid support, then adding a second molecule and an agent to be tested. Alternatively, a second molecule or a second molecule-fusion protein can be attached to the solid support and RIZ and an agent to be tested are added. Control reactions, which do not contain an agent, can be performed in parallel. Following incubation under suitable conditions, which include, for example, an appropriate buffer concentration and pH and time and temperature of incubation that permit binding of a RIZ and a second molecule, the amount of the RIZ and second molecule that have associated in the absence of an agent and in the presence of an agent can be determined.

The association of a RIZ and a second molecule can be detected, for example, by attaching a detectable moiety such as a radionuclide or a fluorescent label to the second molecule and measuring the amount of label that is associated with the solid support, wherein the amount of label detected indicates the amount of association of the second molecule and RIZ. By comparing the amount of specific binding in the presence of an agent as compared to the control level of binding, an effective agent, which alters the association of a RIZ and a second molecule, can be identified. Such an assay is particularly useful for screening a panel of agents such as a peptide library in order to detect an effective agent.

In an in vitro screening assay as disclosed herein, the order in which the components are added can be informative. For example, the agent to be detected can be combined with a RIZ prior to adding a second molecule, can be combined with a second molecule prior to adding a RIZ or can be added after allowing binding of the RIZ and the second molecule. Depending on the relative affinities of the components in the reaction mixture for each other, the order of addition and the time between mixing the first two components and adding the remaining component can be manipulated to detect effective agents with varying properties.

The methods for identifying an effective agent that alters the association of RIZ with a second molecule, can be performed to determine, for example, whether the agent can dissociate a bound RIZ-second molecule complex. For this purpose, a RIZ is first contacted with a second molecule under conditions suitable for forming a RIZ-second molecule complex and thereafter the complex is contacted with the effective agent.

The invention also provides methods for identifying an effective agent that alters the association of a RIZ and a second molecule in a test sample containing the RIZ and the second molecule. As used herein, the term "test sample" means a cell or tissue specimen that is obtained from a subject and is to be examined for expression of RIZ protein or a nucleic acid molecule encoding RIZ. A test sample can be obtained, for example, during surgery or by needle biopsy. The test sample can be, for example, a soluble lysate of a cell preparation obtained by treating the cells with a solubilizing agent such as a non-ionic detergent.

A soluble lysate or other form of test sample can be examined by a gel-shift assay to determine the proportion of a RIZ and a second molecule that are associated as a complex. In this assay, the test sample is electrophoresed in a non-denaturing gel such as a low percentage polyacrylamide gel with a buffer containing 50 mM Tris (pH 8.5), 0.4 M glycine, 2 mM EDTA and 3% glycerol. By adjusting the buffer conditions, gel concentration or other parameters of electrophoresis well known in the art, electrophoretic separation of a free second molecule, a free RIZ and a second molecule-RIZ complex in the test sample can be achieved. After electrophoresis, the identity of proteins in the gel can be determined by immunoblotting using antibodies specific for the second molecule or the RIZ. Methods for performing immunoblotting using an enzyme or radioisotope labeled primary or secondary antibody are well known in the art (see, for example, Harlow and Lane, supra, 1988).

If desired a separate gel can be produced and immunoblotted with either anti-second molecule antibodies or anti-RIZ antibodies. Each gel can contain known amounts of both the second molecule and the RIZ to be detected to provide standards for quantitation and specificity of the blot. The amount of a second molecule-RIZ complex in a test sample treated with an agent suspected of being able to alter the association of the second molecule with RIZ can be compared to a control test sample not treated with the agent in order to identify an effective agent, which increases or decreases the proportion of the second molecule-RIZ complex in the treated relative to the control test sample.

The present invention provides methods to modulate a function of a cell by contacting the cell with an effective agent. As used herein, the term "contacting" means providing within sufficient proximity such that the effective agent can interact with a target. Thus, an effective agent can be contacted with Rb in vitro, or can be contacted with a cell, provided the effective agent can enter the cell to interact with RIZ or a second molecule. For example, a small molecule effective agent can enter a cell passively such as through pores in the cell membrane or through the lipid bilayer of the cell. An effective agent also can enter a cell by active means such as through pinocytosis, endocytosis, phagocytosis or through an energy driven specific transport mechanism.

Methods for introducing and expressing a RIZ in a cell can be performed using well known expression vectors and gene transfer methods (for example, see Sambrook et al., supra, 1989; see, also, Kriegler, *Gene Transfer and Expression: A Laboratory Manual* (W. H. Freeman and Co.; New York, 1990), which is incorporated herein by reference). Such gene transfer methods include, for example, transfection methods such as calcium phosphate precipitation, electroporation or lipofection, or viral infection. For convenience, the term "transfected cell" is meant to include any cell having an exogenous nucleic acid molecule introduced therein. Transfected cells useful for expressing large amounts of RIZ protein can be prokaryotic or eukaryotic and include, for example, bacterial cells such as *E. coli*, yeast cells, insect cells or mammalian cells such as COS cells or Chinese hamster ovary (CHO) cells.

An expression vector useful for expressing a RIZ or a mutant RIZ in a cell contains an expression control sequence operatively linked to a nucleotide sequence encoding a RIZ. An expression control sequence that is operatively linked to a nucleic acid sequence can direct the transcription and translation of the nucleic acid sequence in vitro or in an appropriate host cell. Expression control elements are well known in the art and include, for example, promoters, enhancers and appropriate start and stop codons. In particular, a tissue specific expression control element can provide a means to selectively express a RIZ or mutant RIZ in a cell. Tissue specific control elements are well known in the art and include, for example, the muscle creatine kinase enhancer for restricting expression to muscle cells and the Purkinje cell protein-2 promoter for restricting expression to Purkinje cells (Vandaele et al., *Genes Devel.* 5:1136–1148 (1991), which is incorporated herein by reference).

Viral vectors that are compatible with a targeted cell are particularly useful for introducing a nucleic acid molecule encoding a RIZ or a mutant RIZ into a cell. For example, recombinant adenoviruses having general or tissue-specific promoters can be used to deliver a nucleic acid encoding RIZ into a variety of cell types in various tissues and can direct expression of the nucleic acid in the target cell (Lebkowski et al., U.S. Pat. No. 5,354,678, issued Oct. 11, 1994, which is incorporated herein by reference). Recombinant adeno-associated viruses also are useful for introducing a nucleic acid molecule encoding RIZ into a cell and have the added advantage that the recombinant virus can stably integrate into the chromatin of even quiescent non-proliferating cells such as neurons of the central and peripheral nervous systems (Lebkowski et al., *Mol. Cell. Biol.* 8:3988–3996 (1988), which is incorporated herein by reference).

Such viral vectors are particularly useful where it is desirable to introduce a nucleic acid molecule encoding a RIZ or a mutant RIZ into a cell in a subject, for example, for gene therapy. Viruses are specialized infectious agents that can elude host defense mechanisms and can infect and propagate in specific cell types. The specificity of viral vectors for particular cell types can be utilized to target predetermined cell types. Thus, the selection of a viral vector will depend, in part, on the cell type to be targeted. For example, if a neurodegenerative disease is to be treated by decreasing the level of RIZ in neuronal cells affected by the disease, then a viral vector that targets neuronal cells can be used. A vector derived from a herpes simplex virus is an example of a viral vector that targets neuronal cells (Battleman et al., *J. Neurosci.* 13:941–951 (1993), which is incorporated herein by reference).

A viral vector that is specific for a particular blood cell or its precursor cell can be used to introduce a nucleic acid molecule encoding a RIZ or a mutant RIZ into a hematopoietic cell from a subject having a pathological condition of the hematopoietic system. A vector based on a human immunodeficiency virus is an example of such a viral vector (Carroll et al., *J. Cell. Biochem.* 17E:241 (1993), which is incorporated herein by reference). In addition, a viral vector or other vector can be constructed to express a nucleic acid S encoding a RIZ in a tissue specific manner by incorporating a tissue-specific promoter or enhancer into the vector (Dai et al., *Proc. Natl. Acad. Sci. USA* 89:10892–10895 (1992), which is incorporated herein by reference).

Retroviral vectors can be particularly useful for introducing a nucleic acid molecule encoding a RIZ or a mutant RIZ into a cell in vivo. Retroviral vectors can be constructed either to function as infectious particles or as non-infectious particles that undergo only a single initial round of infection. In the former case, the genome of the virus is modified so that it maintains the necessary genes, regulatory sequences and packaging signals to synthesize new viral proteins and RNA. However, genes conferring oncogenic potential of these viruses are destroyed or removed. After the viral proteins are synthesized, the host cell packages the RNA into new viral particles, which can undergo further rounds of infection. The viral genome also is engineered to encode and express the desired recombinant gene.

In the case of non-infectious viral vectors, a helper virus genome is required to provide the structural genes necessary to encode for the viral structural proteins. However, the helper virus is mutated to destroy the viral packaging signal required to encapsulate the helper viral RNA into viral particles. Thus, only the recombinant viral vector containing the gene of interest and a functional packaging signal, but lacking viral structural genes can be incorporated into a virus particle. Although this new virus can infect a target cell, no further infectious virus can be produced since there are not viral structural genes provided. Methods for constructing and using viral vectors are known in the art and reviewed, for example, in Miller and Rosman, *Biotechniques* 7:980–990 (1992), which is incorporated herein by reference. The specific type of vector will depend upon the intended application. These vectors are well known and readily available within the art or can be constructed by one skilled in the art.

For gene therapy, a vector containing a nucleic acid encoding a RIZ or a mutant RIZ can be administered to a subject by various methods. For example, if viral vectors are used, administration can take advantage of the target specificity of the vectors. In such cases, there is no need to administer the vector locally at the diseased site. However, local administration can be a particularly effective method of administering a nucleic acid molecule. In addition, administration can be via intravenous or subcutaneous injection into the subject. Following injection, the viral vectors will circulate until they recognize host cells with the appropriate target specificity for infection. Injection of viral vectors into the spinal fluid also can be an effective mode of administration, for example, in treating a neurodegenerative disease.

Receptor-mediated DNA delivery approaches also can be used to deliver a nucleic acid molecule encoding a RIZ or a mutant RIZ into a cell in a tissue-specific manner using a tissue-specific ligand or an antibody that is non-covalently complexed with the nucleic acid molecule via a bridging molecule (Curiel et al., *Hum. Gene Ther.* 3:147–154 (1992); Wu and Wu, *J. Biol. Chem.* 262:4429–4432 (1987), each of which is incorporated herein by reference). Direct injection of a naked or a nucleic acid molecule encapsulated, for example, in cationic liposomes also can be used for stable gene transfer into non-dividing or dividing cells in vivo (Ulmer et al., *Science* 259:1745–1748 (1993), which is incorporated herein by reference). In addition, a nucleic acid molecule encoding a RIZ can be transferred into a variety of tissues using the particle bombardment method (Williams et al., *Proc. Natl. Acad. Sci. USA* 88:2726–2730 (1991), which is incorporated herein by reference). Such nucleic acid molecules can be linked to the appropriate nucleotide sequences required for transcription and translation.

A particularly useful mode of administration of a nucleic acid encoding a RIZ or mutant RIZ is by direct inoculation locally at the site of the disease or pathological condition. Local administration can be advantageous because there is no dilution effect and, therefore, the likelihood that a majority of the targeted cells will be contacted with the nucleic acid molecule is increased. Thus, local inoculation can alleviate the targeting requirement necessary with other forms of administration and, if desired, a vector that infects all cell types in the inoculated area can be used. If expression is desired in only a specific subset of cells within the inoculated area, then a promotor, an enhancer or other expression element specific for the desired subset of cells to be targeted can be inked to the nucleic acid molecule. Vectors containing such nucleic acid molecules and regulatory elements can be viral vectors, viral genomes, plasmids, phagemids and the like. Transfection vehicles such as liposomes also can be used to introduce a non-viral vector into recipient cells. Such vehicles are well known in the art.

An alternative method of modulating a function of a cell is to introduce a nucleic acid molecule having a nucleotide sequence encoding an antisense RIZ or a ribozyme specific for a RIZ mRNA into the cell. Such a nucleotides sequence is included within the meaning of an effective agent since it can alter the expression level of RIZ and thus alter the association of a RIZ with a second molecule.

An antisense RIZ or a ribozyme specific for a RIZ mRNA can be complementary to the nucleotide sequence of a RIZ such as the nucleotide sequence of FIG. 1A (SEQ ID NO: 1), FIG. 9A (SEQ ID NO: 3) or FIG. 14 (SEQ ID NO: 104). An antisense RIZ or ribozyme specific for RIZ mRNA can be introduced into a cell using the methods and vectors described above. Chemically synthesized nucleotide sequences also can be administered directly to cells. Synthetic antisense or ribozyme oligonucleotides can be prepared using well known methods or can be purchased from commercial sources and, if desired, can incorporate nucleotide analogs to increase the resistance of the oligonucleotide to degradation by nucleases in a cell. Synthetic antisense or ribozyme sequences can be active in a cell after contact with and uptake by the cell.

An effective agent can be administered in vivo as a pharmaceutical composition containing the effective agent and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters. Methods to formulate pharmaeuctical compositions are well known in the art (see, for example, Renaso et al. *Remington Pharmaceutical Sciences*, Mack Publishing Co., Eaton, Pa. (1990), which is incorporated herein by reference).

A pharmaceutically acceptable carrier can contain physiologically acceptable compounds that act, for example, to stabilize or to increase the absorption of an effective agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. One skilled in the art would know that a pharmaceutical composition containing an effective agent can be administered to a subject by various routes including, for example, by direct instillation, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to modulate a function of a cell, an effective agent is administered in an effective amount, which can be determined using methods well known to those in the art (see, for example, Renaso et al. supra, 1990). As used herein, the term "effective amount" means the amount that produces a desired effect. Thus, an effective amount of an effective agent can alter the association of a RIZ and Rb in a cell and can have a functional effect on the ability of a target cell to increase or decrease its ability to enter the cell cycle. Administration of an effective amount of an effective agent in vivo can reduce symptoms associated with a disease being treated.

The total effective amount can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of an effective agent needed to obtain an effective amount in a subject depends on many factors including the age and general health of the subject as well as the route of administration and the number of treatments to be administered, as well as the chemical form of the effective agent (see, for example, Renaso et al. supra, 1990). In view of these factors, the skilled artisan would adjust the particular dose so as to obtain an effective amount for subject being treated.

The present invention also provides methods for detecting the presence of a RIZ in a test sample by detecting the RIZ protein or a nucleic acid molecule encoding RIZ. In addition, methods are disclosed for diagnosing a pathology that is characterized, in part, by an increased or decreased ability of a cell to enter the cell cycle by determining whether cell proliferation or lack thereof is due, for example, to increased or decreased expression of a RIZ or a mutant RIZ in the cell. The identification of such a pathology can allow for intervention therapy using an effective agent as described above.

A test sample can be obtained from a subject having a pathology characterized by increased or decreased cell function and can be compared to a control sample from a normal healthy subject to determine whether the cells in the test sample have an increased or decreased level of a RIZ or a mutant RIZ. The level of RIZ protein in a cell can be determined by contacting a sample with a RIZ binding reagent such as an anti-RIZ antibody or Rb. For example, the level of RIZ in a cell can be determined by well known immunoassay or immunohistochemical methods using an anti-RIZ antibody (see, for example, Reed et al., supra, 1992; see, also, Harlow and Lane, supra, 1988). In addition, the expression of a mutant RIZ can be detected, for example, by an antibody that specifically binds to the mutant RIZ but not to wild-type RIZ.

The detection of a RIZ by binding to an antibody and to Rb can provide complementary information. For example, the antibody can be used to determine the total level of RIZ expressed, while Rb binding can be used to determine the fraction of RIZ that is bound to Rb. Because Rb can bind to other proteins in a cell, it is advantageous to first isolate RIZ from a cell prior to detecting the fraction of RIZ that is bound to Rb.

An increased or decreased level of expression of a RIZ in a cell in a test sample can be determined by comparison to an expected normal level for the RIZ in a particular cell type. A normal range of RIZ levels in various cell types can be determined by sampling a statistically significant number of normal cell types, which can be obtained from healthy subjects. In addition, a control sample can be evaluated in parallel with a test sample in order to determine whether a pathology characterized by increased or decreased cell function is due to increased or decreased expression of a RIZ or to expression of a mutant RIZ. The test sample can be examined using, for example, immunohistochemical methods as described above or the sample can be further processed and examined. For example, an extract of a test sample can be prepared and examined to determine whether RIZ that is expressed in cells in the sample can associate with Rb in the same manner as RIZ from control cells or whether a variant RIZ, which does not properly associate with Rb, is expressed in the cells in the test sample.

A diagnostic assay kit incorporating a reagent such as an anti-RIZ antibody or Rb can be useful for detecting a pathology due to altered RIZ expression or to expression of a mutant RIZ in a cell. Such a kit is particularly useful because it allows for standardization of assay conditions. A kit can contain, in addition to a reagent, a reaction cocktail that provides suitable reaction conditions for performing the assay and, if desired, a control sample that contains a known amount of RIZ. In addition, the kit can contain an antibody that is specific for the reagent. Where Rb is used as a reagent to detect RIZ, the kit also can contain a competitor molecule such as EIRCEEKPEDL (SEQ ID NO: 6) or EIRCDEK-PEDL (SEQ ID NO: 91), which inhibits the association of RIZ and Rb and, therefore, can confirm the specificity of the binding reaction.

A diagnostic assay should include a simple method for detecting the amount of RIZ in a sample that is bound to the reagent. Detection can be performed by labeling the reagent and detecting the presence of the label using well known methods (see, for example, Harlow and Lane, supra, 1988; chap. 9, for labeling an antibody). A reagent can be labeled with various detectable moieties including a radiolabel, an enzyme, biotin or a fluorochrome. Materials for labeling the reagent can be included in the diagnostic kit or can be purchased separately from a commercial source. Following contact of a test sample and, if desired, a control sample, with a labeled reagent, specifically bound reagent can be identified by detecting the particular moiety.

A labeled antibody that can specifically bind the reagent also can be used to identify specific binding of an unlabeled reagent. For example, if the reagent is an anti-RIZ antibody, a second antibody can be used to detect specific binding of the anti-RIZ antibody. A second antibody generally will be specific for the particular class of the first antibody. For example, if an anti-RIZ antibody is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody, then the sample is contacted with the labeled second antibody, which specifically binds to the first antibody and results in a labeled sample.

A method for diagnosing a pathology characterized by an abnormal level of expression of a RIZ can involve measuring the level of expression of a DNA or RNA in the sample. Similarly, diagnosing a pathology characterized by expression of a mutant RIZ or by the presence of a mutant nucleic acid molecule encoding a RIZ can involve detecting the mutation in the RIZ gene or in the RNA encoded by the gene.

For example, a nucleic acid molecule encoding a RIZ can be detected in a test sample using a complementary nucleotide sequence. If desired, the target nucleic acid molecule can be extracted from a test sample by methods well known in the art (See Sambrook et al., supra, 1988). Methods to detect the presence of a particular nucleic acid molecule within a population of nucleic acid molecules are well known to those in the art and include, for example, Southern blotting, northern blotting, slot blotting and PCR amplification (see, for example, Sambrook et al., supra, 1989). In situ hybridization also can be used to identify nucleic acids directly in a sample containing cells or free chromosomes (see, for example, Pardue, in *Nucleic Acid Hybridisation: A practical approach* (IRL Press, 1991), which is incorporated herein by reference).

To detect a nucleic acid molecule encoding a RIZ in a sample, the sample is contacted with the complementary nucleotide sequence, which can hybridize to a nucleic acid molecule encoding the RIZ under relatively stringent conditions. The nucleotide sequence can carry a detectable label such as a radioisotope. The presence of a nucleic acid molecule encoding the RIZ in the sample can be determined, for example, by detecting the level of the specifically bound nucleotide sequence. The normal level of binding of the nucleotide sequence also can be determined in a control sample. An increase or a decrease in the level of nucleic acid molecules encoding a RIZ in the test sample compared to the control sample indicates a pathology characterized by an abnormal expression of the RIZ. A complementary nucleotide sequence for a RIZ can also be used as a primer in a PCR reaction to amplify the RIZ for hybridization by a probe.

A mutant RIZ can be detected by hybridizing with a complementary nucleic acid molecule under relatively stringent conditions essentially as described above except that the complementary sequence is of sufficiently small size to enable selective hybridization to the mutant sequence but not to the wild-type sequence under the conditions chosen for hybridization. Alternatively, the RIZ gene or RNA can be purified directly from a test sample and, if desired, amplified from the sample by PCR and the mutant sequence determined by standard nucleotide sequencing methods (see, for example, Sambrook et al. supra, 1989). The mutant nucleic acid encoding a RIZ or the nucleic acid encoding a mutant RIZ also can be detected in a sample of cells or free chromosomes by in situ hybridization techniques (see, for example Pardue, supra, 1991).

The following Examples are intended to illustrate but not limit the invention.

EXAMPLE I

Cloning of Mammalian RIZ cDNAs

This section describes methods to clone nucleic acid molecules encoding a RIZ from mammalian cDNA and genomic libraries.

A rat RIZ cDNA was obtained from a rat neonatal cardiac myocyte λgt11 cDNA expression library (Zhu et al., *Mol. Cell Biol.*, 13:4432 (1993), which is incorporated herein by reference). The library was screened using a 56 kD fragment containing the pocket binding site of Rb and the EE epitope (p56EERb) according to previously described methods (Macgregor et al., *Oncogene*, 5:451–458 (1991), which is incorporated herein by reference).

p56EERb was generated by cloning a synthetic pair of complementary polynucleotides that hybridize to form a double stranded linker encoding the EE-epitope, EEEYMPME (SEQ ID NO: 8; Grussenmeyer et al., *Proc. Natl. Acad. Sci., USA.*, 82:7952–7954 (1985) and Walter, *J. Immune Meth.*, 88:149–161 (1986), both of which are incorporated herein by reference) and having Bsm I cohesive ends. The ends of the linker were phosphorylated by T4 kinase and the linker was ligated into the plasmid pET8Rbc (Huang et al., *Nature*, 350:160–162 (1991), which is incorporated herein by reference) to produce the plasmid p56EERb. The synthetic nucleotides used to make the linker were: 5'-AATCGATGAA GAAGAAGAAT ATATGCCTAT GGAACA-3' (SEQ ID NO: 9), and 5'-TTCCATAGGC ATATATTCTT CTTCTTCATC GATTTG-3' (SEQ ID NO: 10). A clone with four tandem copies of the EE linker was selected and used to direct expression of p56EERb in the *E. coli* strain BL21 (DE3)pLysS as previously described (Huang et al., supra, 1991).

After induction of 56EERb, the bacterial cells were lysed as described (Huang et al., supra, 1991) and 56EERb was precipitated by ammonium sulfate (60% of saturation). The precipitate was dialyzed in dialysis buffer (20 mM Tris-HCl, pH 7.5, 50 mM NaCl, 1 mM EDTA, 1 mM DTT, 1 mM PMSF) and subjected to further purification by diethylaminoethyl (DEAE) Sepharose™ chromatography (Pharmacia; Piscataway N.J.). Partially purified p56EERb was eluted from DEAE by a salt gradient of 50 mM to 500 mM NaCl. Both the DEAE partially purified fraction and the dialyzed ammonium sulfate precipitate of 56EERb were used for screening the cDNA library.

For binding-specificity control, p56EERb was preincubated with 5 μM poly-L-lysine (Sigma) or 50 μM T- or K-peptide (Huang et al., supra, 1991) before applying onto filters. T peptide is an 18 residue synthetic peptide derived from residues 101–118 of SV40 large T antigen, while K peptide is the same as T peptide except for a lysine residue substituted for a glutamic acid residue at position 107 of SV40 large T antigen (Huang et al., supra, 1991). The T peptide binds to the Rb pocket while the K peptide does not.

The binding of p56EERb to a clone expressing a RIZ protein was detected using an anti-EE monoclonal antibody obtained as spent culture medium of the anti-EE hybridoma (Walter, supra, 1986) and an alkaline phosphatase conjugated goat anti-mouse IgG antibody specific for mouse immunoglobulin (Promega; Madison Wis.).

Filters containing $1 \times 10^6$ library phage plaques were screened using p56EERb and ten positive clones that survived three rounds of plaque purification were selected. Five clones, which maintained their reactivity with p56EERb in the presence of a non-specific inhibitory substance, poly-L-Lysine, but were inhibited from binding p56EERb in the presence of T peptide but not K peptide, were selected for further study. Inhibition by T peptide indicated that the selected clones expressed a product that binds the Rb pocket.

Of the final five clones, four contained an identical 1.9 kilobase (kb) insert. One of the clones, clone 7.1, was subjected to nucleotide sequencing. Sequencing was performed on both strands of the DNA and utilized Sequenase™ (United States Biochemical Corp.; Arlington Hts. Ill.). Clone 7.1 contained a partial cDNA sequence having a predicted open reading frame encoding 638 amino acids, which formed two types of readily recognizable motifs: a cr2 core motif and 3 zinc finger motifs (see below). The protein encoded by clone 7.1 was designated RIZ for "Rb-interacting zinc finger" protein.

The 1.9 kb insert was used to further screen the cardiac myocyte library and to screen a rat brain B49 cell cDNA library produced in the λZAP vector (Stratagene) according to standard methods (see Sambrook et al., supra, 1989) or purchased from a commercial source. Several clones containing overlapping open reading frames were obtained. The overlapping sequences were assembled into a contiguous stretch of 6171 nucleotides to obtain the cDNA sequence for rat RIZ (FIG. 1A; SEQ ID NO: 1).

Screening of the rat brain cDNA library also revealed clone 12.1, which contained a nucleotide sequence that encoded an alternative 5'-untranslated sequence as compared to the sequence shown in FIG. 1A (see FIG. 1B; SEQ ID NO: 94). Thus, at least two forms of RIZ mRNA are expressed in rat brain, suggesting that RIZ mRNA molecules can arise by alternative splicing.

Analysis of the complete rat RIZ cDNA sequence (SEQ ID NO: 1) revealed a large open reading frame beginning at nucleotide 157 and ending at nucleotide 5274 (see SEQ ID NO: 2). The initiation codon at nucleotide 157 was considered the translational start site based on its being the first ATG following an in-frame upstream stop codon at nucleotide 100 and by its match with the Kozak consensus sequence (Kozak, *Nucl. Acids Res*. 15: 8125–8148 (1987)). The identity of the start site was confirmed by analyzing an independent cDNA clone that revealed a divergent sequence upstream of nucleotide 92 but otherwise was identical to the assembled cDNA sequence of rat RIZ.

The complete rat RIZ cDNA sequence predicted a protein consisting of 1706 amino acids having a molecular weight of 187,437 Daltons (FIG. 1A; SEQ ID NO: 2). Northern blot analysis showed a 7.2 kb major rat RIZ mRNA species. Southern blot analysis indicated that the rat RIZ genome contains a single copy of the RIZ gene. This result, along with the identification of alternative 5'-termini in cDNA molecules encoding rat RIZ, indicates that the different mRNA molecules arise via alternative splicing.

A nucleic acid molecule encoding human RIZ was cloned from a human fetal brain cDNA library (Clonetech; Palo Alto Calif.) and a human placental genomic cosmid DNA library (Stratagene; San Diego Calif.) using the rat RIZ cDNA coding regions as a hybridization probe (clone 7.1). The human RIZ cDNA encodes a polypeptide of 1719 amino acids residues (see FIG. 9A; SEQ ID NO: 4). In addition to the coding sequence, the human RIZ cDNA contains 5' untranslated as well as a partial 3' untranslated sequence (FIG. 9A; SEQ ID NO: 3). Additional 3' untranslated sequence (not determined) for the human RIZ cDNA is located downstream of SEQ ID NO: 3 and upstream of the 3' untranslated sequence shown in FIG. 9C (SEQ ID NO: 97; sequence obtained from Washington University-Merck EST Project; Genbank accession number R56425). The human RIZ gene obtained from the genomic library showed that RIZ coding sequence was divided between eight separate exons.

An allelic variant of the human RIZ gene also was identified. This variant contains a single nucleotide change of $T_{969}$ to $A_{969}$, leading to a change of amino acid residue $D_{283}$ to $E_{283}$. The $T_{969}$ allele is estimated to be two times more frequent than the $A_{969}$ allele.

Nucleotide sequences encoding additional human RIZ proteins were isolated from a cDNA library prepared by standard procedures from Y79 retinoblastoma cells. As shown in FIG. 9B, cDNA molecules encoding two alternative 5' sequences of human RIZ were identified (SEQ ID NOS: 95 and 96; clones 5Y and 1Y, respectively). Clones 5Y (SEQ ID NO: 95) and 1Y (SEQ ID NO: 96), which replace the first 129 nucleotides shown in FIG. 9A (SEQ ID NO: 3), do not encode an ATG initiation codon (see SEQ ID NOS: 102 and 104, respectively). These results indicate that various RIZ proteins can be encoded by alternatively spliced mRNA molecules.

Both the rat and human RIZ proteins have similar sequence motifs including cr1, cr2, ce1, zinc finger, SH3, SH2 and a nuclear localization signal. The deduced rat and human RIZ amino acid sequences show 83% identity. In addition, a rabbit antiserum prepared to rat RIZ cross reacts with human RIZ.

In addition, a 391 nucleotide sequence encoding a portion of mouse RIZ was obtained by combining sequences of several clones selected from the mouse genomic library 129SVJ (Strategene) by a rat cDNA PR domain probe. The mouse cDNA encodes 130 amino acids (SEQ ID NO: 105) that are equivalent to a.a. positions 77 to 206 of rat RIZ (SEQ ID NO: 2) and a.a. positions 78 to 207 of human RIZ (SEQ ID NO: 4). In particular, the encoded mouse peptide contains blocks B and C of the PR domain peptide. The encoded portion of the mouse PR domain peptide is identical to the corresponding human and rat RIZ PR domain peptide sequences.

EXAMPLE II

Detection and Characterization of RIZ-Rb Binding

This section describes methods for demonstrating binding of RIZ and Rb and for identifying an agent that effectively alters the binding of a RIZ and Rb.

To characterize the interaction between RIZ and Rb, a $^{35}$S-labeled fragment of rat RIZ from amino acid position 245–883 (RIZ (245–883)) was produced by subcloning the 1.9 kb insert of clone 7.1 into pBKS+ (Stratagene) to yield plasmid pBKS+7.1. Following subcloning, the RIZ insert was then removed and inserted downstream of the 5' untranslated sequence of β-globin in the vector pSP64-xβm (Krieg and Melton, *Nucl. Acids Res.*, 12:7057–7070 (1984). SP6 RNA transcripts encoding RIZ (245–883) were produced by linearizing the plasmid encoding this fragment with Sal I and translating the RIZ fragment using a rabbit reticulocyte lysate in vitro protein translation system (Promega) containing $^{35}$S-methionine. The labeled RIZ fragment had an apparent molecular weight of 125 kD by sodium dodecyl sulfate polyacrylamide gel electrophoresis (SDS-PAGE), which was about 55 kD greater than the predicted molecular mass for this fragment of RIZ. The larger size obtained by SDS-PAGE is likely due to anomalous mobility of the RIZ fragment on the gel.

A 56 kD fragment of Rb produced by bacterial expression from p56Rb plasmid, as described previously (Huang et al., supra, 1991), was tested for binding to radiolabeled RIZ (245–883). Binding was detected by immunoprecipitation with an anti-Rb antiserum and Protein A-Sepharose™ (Huang et al., supra, 1990), which is incorporated herein by reference; and Huang et al., supra, 1991) followed by SDS-PAGE and autoradiography (see Harlow and Lane, supra, 1988). The rabbit anti-Rb antiserum was produced to purified p56Rb using previously described methods (see Harlow and Lane, supra, 1988).

The amount of binding of RIZ by Rb in the immunoprecipitation reaction was dependent on the concentration of Rb added. Full binding of $^{35}$S-labeled RIZ (245–883) was achieved by 10 nM Rb but not 3.3 nM Rb (not shown). These results indicted that RIZ binds Rb.

A competition experiment was used to compare the relative binding affinity of RIZ for Rb as compared to another Rb binding protein, SV40 large T antigen. The full length large T antigen cDNA was subcloned from Y-62-25-2 into plasmid pSP64 for in vitro transcription/translation and $^{35}$S-methionine labeling as described above. When approximately equal amounts of T antigen and RIZ were mixed individually or together with the same amount of Rb, similar amounts of T antigen and RIZ, or somewhat more RIZ, were co-precipitated (not shown). These data indicate that RIZ has a similar binding affinity for Rb as does large T antigen.

Several mutations were generated to identify the regions of RIZ that were involved in binding to Rb. A single amino acid substitution was introduced into full length RIZ cDNA in the plasmid pCMVRIZ to change cysteine at a.a. position 307 to glycine. pCMVRIZ was produced by subcloning the full-length RIZ cDNA into the pRc-CMV vector (Invitrogen, San Diego, Calif.). Mutagenesis of the cr2 motif changing Cys to Gly was performed using the T7 GENE mutagenesis kit (United States Biochemical, Arlington Heights, Ill.) as follows: Briefly, the primer, 5'-CCGGAGATCC GGGCTGAAGA AAAGCCA -3' (SEQ ID NO: 11), was used to direct DNA synthesis on a single stranded antisense template prepared from pBSK-5.4. Vector pBSK-5.4 was produced by cloning the cDNA RIZ amino terminal clone 5.4 obtained from the B49 λZAP DNA library into vector pBSK+. An Nsi I to Spe I fragment (nucleotide 1–1718) containing the point mutation was sequenced and subcloned into pRc-CMV to produce pCMVmRIZ (RIZ$^{307\text{-}Gly}$). A $^{35}$S labeled fragment of RIZ from amino acid position 1–575 (RIZ (1–575)) and $^{35}$S-RIZ (1–575)$^{307\text{-}Gly}$ were produced by in vitro transcription/translation of Spe I linearized template as described above.

Binding between labeled RIZ (1–575) and the glycine mutant with 33 nM Rb was evaluated by immunoprecipitation with anti-Rb antiserum followed by SDS-PAGE and autoradiography. The results showed that the 56 kD Rb bound the $^{35}$S-RIZ (1–575) fragment but not to the $^{35}$S-RIZ (1–575)$^{307\text{-}Gly}$ cr2 mutant (not shown). These results indicate that the RIZ cr2 motif is involved in Rb binding.

To determine whether the RIZ cr2 motif is functional and sufficient for binding Rb, the 11 amino acid peptide EIRCEEKPEDL (SEQ ID NO: 6), representing a portion of the cr2 motif of RIZ (RIZ-Pep), and a cysteine to glycine mutant of this peptide (RIZ-Pep*) were synthesized according to standard procedures and tested at various concentrations for their ability to inhibit the binding of labeled RIZ (1–575) to 56 kD Rb. Binding was inhibited with wild-type peptide but not the C→G mutant peptide (see FIG. 4). These data indicate the cr2 motif of RIZ is sufficient for binding to Rb and that the cysteine at a.a. position 307 in the cr2 motif of RIZ is involved in the binding.

Figure 4:
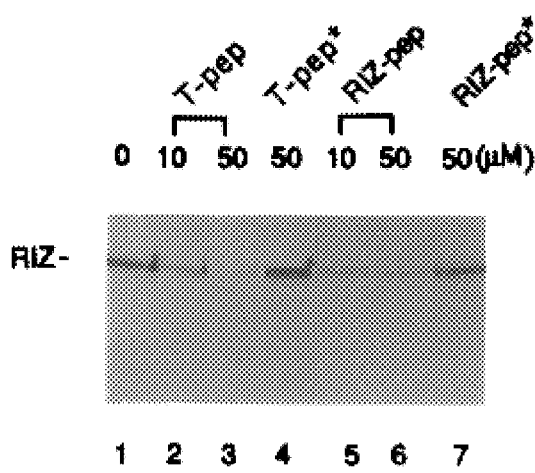
FIG. 4 demonstrates that $^{35}$S-labeled RIZ (a.a. position 1–575) specifically binds to Rb in vitro. Binding assays were performed in the absence or presence of peptides derived from RIZ or SV40 large T antigen. T-pep: peptide of large T antigen (a.a. position 101–118); T-pep*: single amino acid residue mutant of T-pep ($107^{Glu}$); RIZ-pep: peptide of RIZ (a.a. position 304–314); RIZ-pep*: single amino acid mutant of RIZ pep ($307^{Gly}$).

In a similar manner, the binding between radiolabeled RIZ (1–575) and 56 kD Rb was tested for inhibition using the 17 amino acid Rb binding peptide (101–118: T-pep) from the SV40 large T antigen oncoprotein and a position 107 Glu to Lys mutant of T-pep (T-pep*) that lacks Rb binding activity (Huang et al., supra, 1990, and Huang et al., supra, 1991). Binding was inhibited with T-pep but not with the mutant (FIG. 4). These results indicate that RIZ and large T antigen bind to a similar region on Rb.

The 56 kD Rb fragment that binds to RIZ is a C-terminal fragment containing the Rb pocket binding region and a C-terminal extension. To further define the portion of 56 kD Rb that binds to RIZ, several Rb mutant polypeptides were tested for binding to RIZ. Mutant and full length Rb were cloned and in vitro transcribed/translated as described previously (Huang et al., supra, 1990). H209 is a point mutation resulting in a single amino acid change in Rb that was identified in the small cell lung cancer H209 cell line (American Type Culture Collection (ATCC) #HTB 172). The various Rb forms were tested for binding to glutathionine S-transferase (GST) fused to a fragment of RIZ from amino acid position 245–573 (GST-RIZ (245–573)). This RIZ fragment contains all of the E1A motifs related to binding Rb and was constructed by cloning a Stu I-Hpa I RIZ fragment (nucleotide 795–3068) into vector pBSK+ to make pBSK+SH. An Eco RI fragment was removed from PBSK+SH and ligated into pGEX-KG to produce vector pKG7.1S containing GST-RIZ (245–573).

The binding between purified GST-RIZ (245–573) and the above radiolabeled Rb wild-type and deletion mutants was determined by immunoprecipitation with an anti-RIZ antiserum followed by SDS-PAGE and autoradiography. The antiserum was generated by injecting rabbits with the purified GST fused to a fragment of RIZ from amino acid position 245–573 (RIZ (245–573)), which contains zinc fingers 1–3, according to commonly used procedures (see Harlow and Lane, supra, 1988). GST-RIZ (245–573) used for immunizing rabbits was produced by expression of plasmid pKG7.1S in *E. coli* strain XL-1 blue. The bacteria were lysed and the GST-RIZ fusion protein isolated by glutathionine agarose column chromatography. pKG7.1S was constructed by ligating the 1.9 kb RIZ insert from pB7.1 into vector pGEX-KG. The resulting plasmid was linearized with Spe I, treated with Klenow fragment of DNA polymerase I and religated, thereby introducing a stop codon at the former Spe I site (nucleotide 1876).

The anti-RIZ antiserum specifically bound to in vitro translated RIZ (245–883) expressed from pB7.1. This binding was inhibited by the addition of the immunogen, GST-RIZ (245–573).

Figures 5A, 5B:
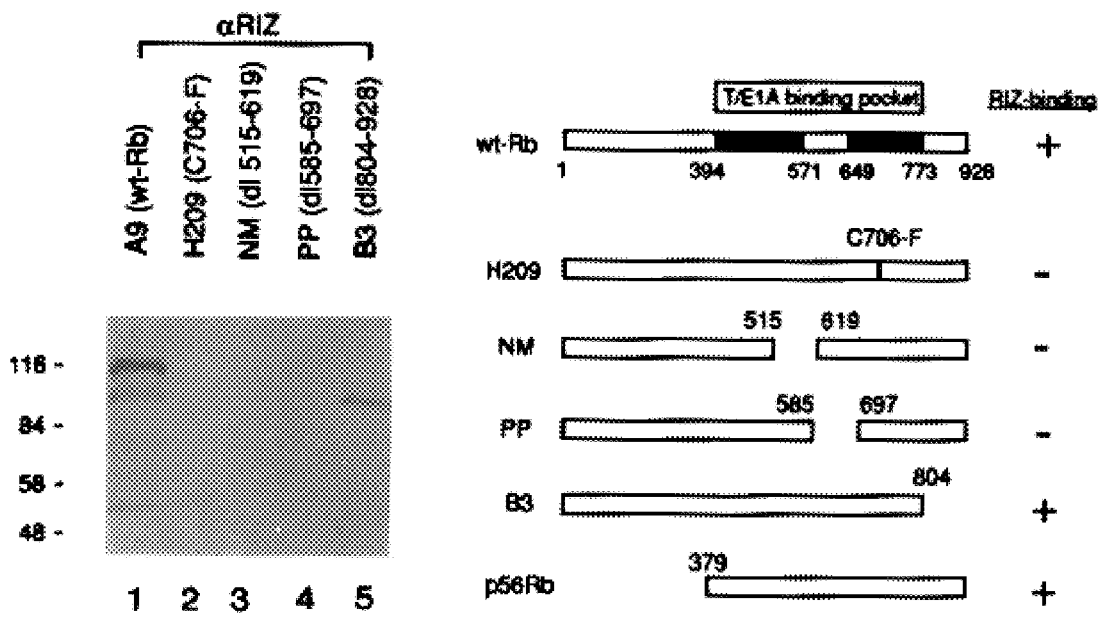
FIGS. 5A and 5B: Use of Rb deletion mutants to map the RIZ binding site of Rb.

Purified GST-RIZ (245–573) showed binding to wild-type Rb and the B3 mutant of Rb, which contains a deletion C-terminal to the Rb binding pocket, but failed to bind three different forms of Rb having a deletion within the pocket (FIG. 5A). These results indicate that the Rb pocket, which was initially defined for its role in binding of oncoproteins such as the large T antigen or E1A, also is required for binding to RIZ. RIZ-binding by Rb does not require the C-terminal sequence distal to the pocket, as do certain cellular proteins such as E2F (see Huang et al., *DNA Cell Biol.*, 11:539–548 (1992); Qin et al., *Genes Devel.*, 6:953–964 (1992)) and c-Abl oncoprotein (see Welch and Wang, *Cell* 75:779–790 (1993)). The binding results map the C-terminal boundary of the RIZ-binding domain of Rb to residue 803 of Rb, in close proximity to the beginning of the C-terminal boundary of the Rb pocket (FIG. 5B).

Rat RIZ was tested for binding to Rb in HT1080 cells (ATCC #ICCL 121). The cells were grown in DMEM supplemented with 10% fetal calf serum. Cells were lysed in ELB buffer (50 mM HEPES, pH 7.5, 250 mM NaCl, 0.1% NP-40) supplemented with 5 mM EDTA, 50 mM NaF, 1 mM Na orthovanadate, 1 mM of DTT, aprotinin, leupeptin, and PMSF. The lysate was cleared of cell debris by centrifugation at 12,000 rpm for 10 min in a microfuge.

Binding between 4 μg GST-RIZ (215–462) and Rb from HT1080 cell extract was evaluated by first mixing the two, then binding GST-RIZ and any associated Rb to glutathione-agarose beads. The beads were washed in binding buffer and the bound complexes were eluted by boiling in SDS buffer and analyzed by immunoblotting with anti-Rb antiserum. Immunoblotting was performed by standard techniques (see, for example, Harlow and Lane, supra, 1988).

Figure 6:
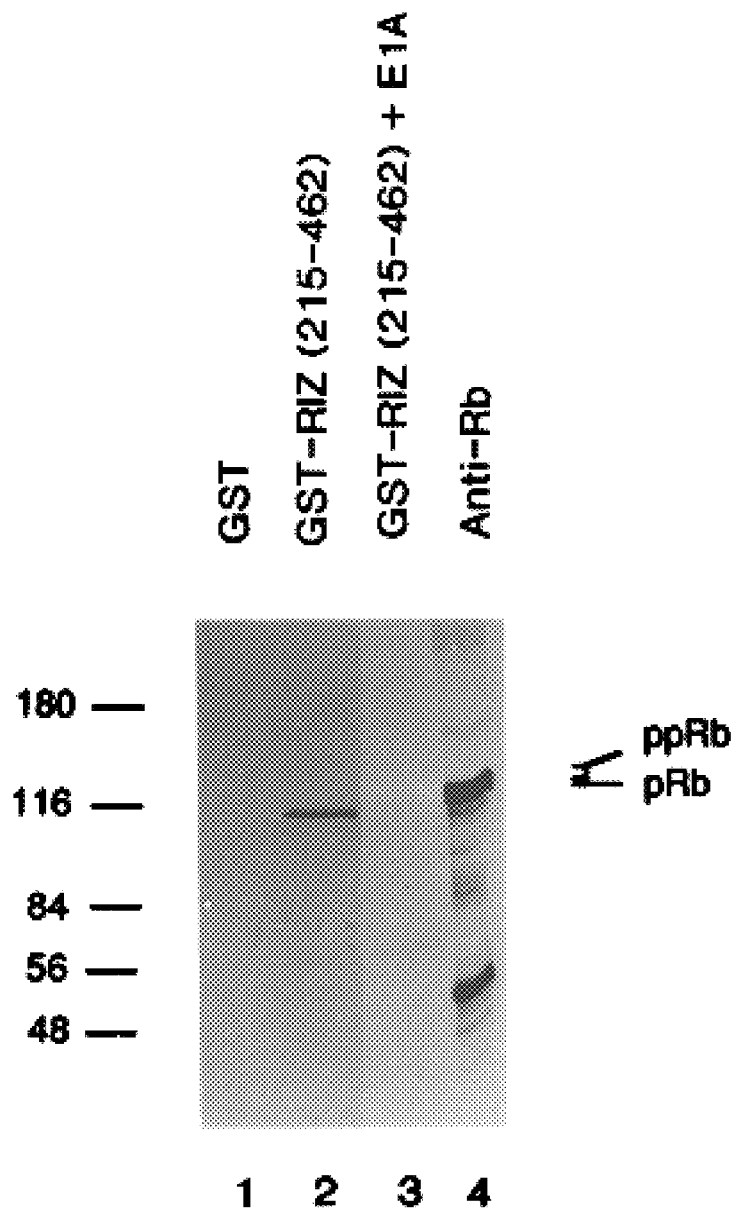
FIG. 6 shows in vitro binding of Rb from HT1080 cells with purified rat RIZ (a.a. position 215–462) fused C-terminal to glutathionine S-transferase (GST). The positions of hypophosphorylated Rb (pRb) and phosphorylated Rb (ppRb) from HT1080 cell extract are indicated in lane 4. Numbers to left indicate the migration of molecular weight markers (kiloDaltons).

GST-RIZ (215–462) bound to the fastest migrating forms of Rb, representing hypophosphorylated Rb (FIG. 6, lane 2). The specificity of the interaction between RIZ and hypophosphorylated Rb was demonstrated by showing that the addition of a source of E1A protein inhibited binding (FIG. 6, lane 3). A cell lysate from 293 stably transfected to express E1A was used as the source of E1A.

EXAMPLE III

Structural and Functional Comparison between RIZ and E1A

The similarity in sequence of particular domains between RIZ and Adenovirus E1A (see FIG. 2A) and the shared property of Rb binding indicated significant structural similarity between RIZ and E1A. To investigate this relationship further, the anti-RIZ antiserum raised against the GST-RIZ (245–573) fusion protein containing the cr2, ce1 and part of the cr1 motifs, was tested for cross reactivity with E1A. For these experiments, E1A was labeled with $^{35}$S-methionine during in vitro transcription/translation using methods described above.

Anti-RIZ antiserum cross reacted weakly with E1A (not shown). To further verify binding between anti-RIZ and E1A, the cross reactive antibodies from the anti-RIZ antiserum were purified by affinity chromatography on a column containing E1A 12S protein. The column was prepared by coupling Affi-gel 10™ beads (Bio-Rad Labs; Hercules Calif.) with the purified GST-E1A 12S fusion protein expressed from pGSTE1A12S (Taylor et al., *Mol. Cell. Biol.* 13:4714–4727 (1993), which is incorporated herein by reference). Antibody affinity purification was conducted by high pH elution according to standard procedures (see Harlow and Lane, supra, 1988).

Anti-RIZ antibodies purified from the E1A affinity column were tested for binding to RIZ and E1A. Both proteins were bound by the antibodies, confirming the original cross reactivity of the anti-RIZ antiserum with E1A 12S (not shown). The E1A-affinity purified RIZ antibodies were designated "anti-ce1" for cross reacting E1A antigen.

Anti-ce1 antibodies were tested for binding to various deletion mutants of RIZ and E1A 12S in order to map the location of the ce1 epitope on each molecule. A RIZ mutant truncated after residue 304 (RIZ304) was produced by in vitro transcription/translation of a BAM HI digested fragment derived from a BAM H1 mutant of pCMVRIZ. A T7 GEN™ mutagenesis kit (U.S. Biochemical) was used to introduce a Bam HI restriction site into pCMVRIZ at RIZ nucleotide 1067 using the primer 5'-TTCACACCGG ATC-CCCGGCT CTTTCGC -3' (SEQ ID NO: 12). The Bam HI fragment was then excised and cloned into pRc-CMV to yield a vector encoding RIZ304.

A RIZ mutant truncated after residue 318 (RIZ318) was produced by PCR using full-length RIZ as the template and an upstream T7 primer (Stratagene) and a downstream RIZ primer 5'- TGGCTCTTCT AATAAGTC -3' (SEQ ID NO: 13). The PCR fragment was cloned into pCRSK+ (Stratagene) and used to produce the RIZ318 polypeptide by in vitro T7 transcription/translation.

E1A 12S, truncated at residue 223 (E1A223) was produced by generating a PCR fragment of E1A using an upstream SP6 primer (Stratagene) a downstream E1A primer 5'- GATACATTCC ACAGCCTG -3' (SEQ ID NO: 19) and the plasmid pGEM1Ad5E1A12S as template. The resulting PCR fragment was cloned into pCRSK+, which was used to direct the synthesis of the mutant E1A 12S protein by SP6 in vitro transcription/translation. The full length E1A 12S (E1A243) was produced from vector pGEM1Ad5E1A12S by in vitro transcription/translation as described above for the other vectors.

Anti-ce1 antibody bound to RIZ truncated at residue 318 but failed to react with RIZ truncated at residue 304 (not shown). These results indicate that the ce1 cross reactive antigenic determinant lies within residues 304 to 318 of RIZ. Anti-ce1 antibody bound to full length E1A (EIA243) but failed to react with the C-terminal deletion mutant of E1A (E1A223; not shown). These results indicate that the ce1 epitope is located within the C-terminal 20 amino acids of E1A 12S.

The regions of RIZ and E1A 12S that contain the ce1 epitope show significant amino acid sequence homology (FIG. 2A). The sequence $^{312}$EDLLEE (SEQ ID NO: 20) in RIZ and the sequence $^{224}$EDLLNE (SEQ ID NO: 21) in E1A are likely sites for the ce1 epitope. To evaluate this possibility, an 11 amino acid peptide encompassing residues 310–320 in RIZ (ce1 peptide) KPEDLLEEPQS (SEQ ID NO: 7) and an overlapping 11 amino acid control peptide encompassing residues 304–314 containing the cr2 core motif of RIZ, peptide EIRCEEKPEDL (SEQ ID NO: 6), were synthesized by solid phase peptide synthesis and tested for their ability to block binding between anti-ce1 antibody and RIZ or E1A.

The ce1 peptide inhibited binding between anti-ce1 antibody and either $^{35}$S-RIZ318 or $^{35}$S-E1A 12S (E1A243); the cr2 peptide was not inhibitory (not shown). These experiments indicated that the ce1 epitope is located in the sequence $^{312}$EDLLEE (SEQ ID NO: 20) in RIZ and the homologous sequence $^{224}$EDLLNE (SEQ ID NO: 21) in E1A.

Anti-ce1 was tested for binding to a preformed RIZ-Rb complex to determine if the ce1 epitope is directly involved or closely associated with regions in the RIZ-Rb binding interface. In these experiments, $^{35}$S-labeled full-length Rb was preincubated with in vitro translated RIZ (215–462) to form the RIZ-Rb complex prior to adding anti-ce1 antibody for immunoprecipitation. In these experiments, the GST portion of GST-RIZ (215–462) had been previously removed by thrombin cleavage and was purified from any residual uncleaved fusion protein by adsorption with glutathionine-agarose.

The anti-ce1 antibody bound to the preformed RIZ-Rb complex (not shown). Although the binding could be characterized as weak, this was similar in reactivity with anti-ce1 binding with RIZ. Because no evidence of RIZ homo-oligomer formation was observed, Rb likely interacts directly with RIZ that also was bound by anti-ce1. The failure to observe homo-oligomer formation was based on the lack of binding between GST-RIZ (215–462) and $^{35}$S-labeled full length RIZ.

The above binding study also was performed in reverse order by first precomplexing $^{35}$S-labeled RIZ (1–575) with full-length Rb, then testing the complex for binding to anti-ce1 antibody. The result showed that the RIZ fragment bound anti-ce1 antibody regardless of whether RIZ had complexed with Rb (not shown). These experiments indicate that the ce1 epitope is not significantly involved in the interface between RIZ and Rb in the RIZ-Rb complex.

EXAMPLE IV

DNA- And GTP-Binding Activities of RIZ

To evaluate whether the zinc finger domains of RIZ can bind to DNA, the RIZ finger motifs 1 to 3 from amino acid position 245–573 or finger 4 to 6 from amino acid position 1114–1260 were expressed as GST fusion proteins, GSTZ13 and GSTZ46, respectively. The GST-RIZ fragments were purified by glutathionine agarose chromatography (Guan and Dixon, Anal. Biochem. 192:262–267 (1991), which is incorporated herein by reference) and evaluated for binding in a filter-based DNA-binding assay (Sukegawa and Blobel, Cell 72:29–38 (1993), which is incorporated herein by reference). To obtain GSTZ46, a fragment encoding RIZ (1114–1260) was made by PCR using primers 5'- GTGGTC-CAAG AAACATTC -3' (SEQ ID NO: 17) and 5'- TCGT-GTAAAG CTCTTCAG -3' (SEQ ID NO: 18) and pCM-VRIZ as template. The PCR fragment was cloned into pBKS+, then into pGEX-KG (Guan and Dixon, supra, 1991).

The filter-based DNA binding assay was performed by electrophoresing 0.5 μg of purified GST or GST-RIZ fusion proteins by SDS-PAGE and transferring the proteins to nitrocellulose. The proteins were renatured by incubating the nitrocellulose for 3 hr in binding buffer (50 mM Tris-HCl, pH 8, 100 mM KCl, 0.1% Triton X-100™, 10% glycerol, and 0.1 mM $ZnCl_2$). $^{32}$P-labeled, randomly sheared rat ovary genomic DNA was added to the buffer and the nitrocellulose was incubated for an additional 3 hr. Blots were washed 5 times in binding buffer, dried, then autoradiographed. In some experiments, the binding buffer contained 10 mM EDTA and 2 mM DTT but no $ZnCl_2$.

Figures 7A, 7B, 7C:
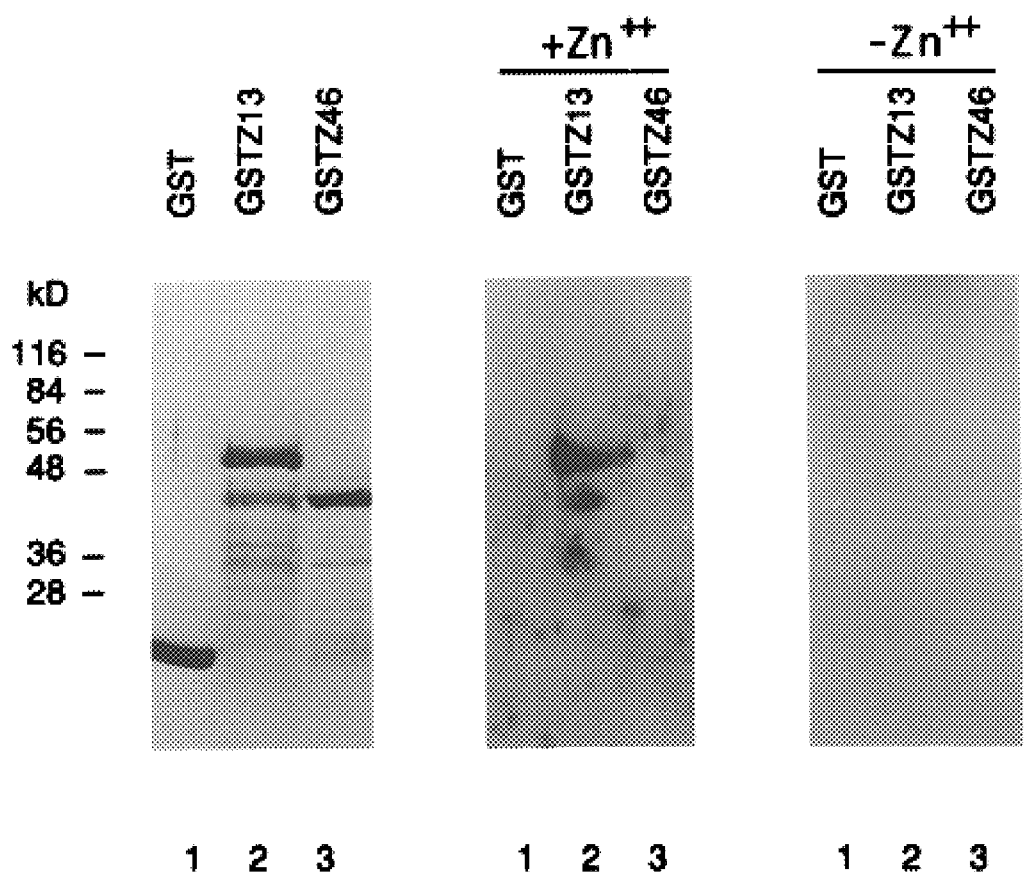
FIGS. 7A to 7C demonstrate that rat RIZ protein binds DNA.

The DNA filter binding assay showed that GSTZ13, containing zinc fingers 1 to 3 bound to rat DNA while GSTZ46, containing zinc fingers 4 to 6 did not bind (FIG. 7A and 7B). In addition, RIZ fragment containing zinc fingers 1–3 bound to DNA in a $Zn^{++}$ ion dependent manner (FIG. 7). These results indicate that RIZ zinc finger domains 1 to 3 are active in binding DNA.

The GTPase domain of RIZ, which was defined by sequence homology, was evaluated to determine if it was functionally active. For these studies, a fragment of RIZ from amino acid position 760–949 (RIZ 760–949), containing the putative GTPase domain was expressed as a fusion to GST from the plasmid pKG-G and tested for binding to radiolabeled nucleotides. pKG-G was produced by PCR amplification of the nucleotide sequence encoding RIZ (760–949) using primers 5'-TCTCCACAGC ACAGCCCT-3' (SEQ ID NO: 15), and 5'-GGATAAGGAG GCTGTCTG-3' (SEQ ID NO: 16) and pCMVRIZ as template. The fragment was cloned into pBSK+ and then into pGEX-KG, expressed and purified by glutathionine-agarose as described above. GST was also expressed from vector pGEX-KG and purified as described above.

To measure GTP-binding, 0.5 μg of GST-RIZ or control GST proteins were separated by SDS-PAGE and blotted onto nitrocellulose. Proteins were renatured in GTP-binding buffer (50 mM Tris-HCl, pH8, 100 mM KCl, 10% glycerol, 0.1% Triton X-100, and 2 mM $ZnSO_2$). The nitrocellulose was incubated for 30 min in GTP-binding buffer and then for 2 hr in GTP-binding buffer containing 1 μM α-$^{32}$P-GTP (800 Ci/mmol). The nitrocellulose was washed 5 times in GTP-binding buffer, dried and autoradiographed. In some samples, 20 mM unlabeled nucleotides were incubated with the nitrocellulose for 1 hr prior to the addition of α-$^{32}$P-GTP.

Figure 8A:
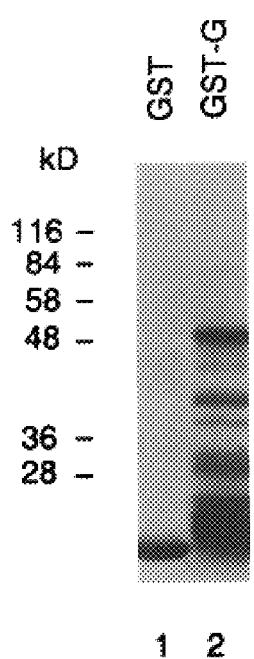
FIGS. 8A and 8B show the GTP-binding activity of rat RIZ GTPase domain (a.a. position 760–949).
Figure 8B:
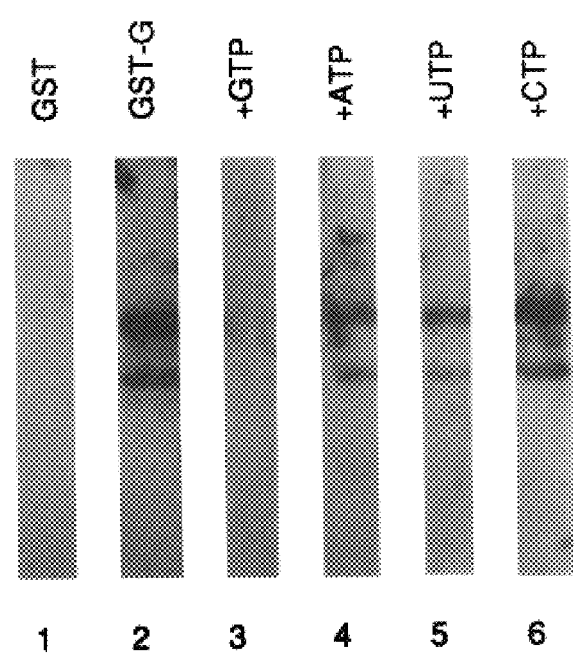

The RIZ GTPase fusion protein (GST-G), but not the control GST protein, bound to radiolabeled GTP (FIG. 8A and lanes 1 and 2 of FIG. 8B). Binding was specific for GTP, as an excess amount of unlabeled GTP inhibited binding of RIZ GTPase to radiolabeled GTP but excess unlabeled ATP, CTP, or UTP did not effect binding (FIG. 8B, lanes 3–6). These data indicate that the GTPase domain of RIZ is functionally active.

EXAMPLE V

Expression of RIZ in Cells, Tissues and Organs

This example provides methods to identify nucleic acid molecules encoding a RIZ in mammalian cells, tissues and organs.

RNA samples were obtained from rat tissues and from the mouse pituitary cell line Att-20 (ATCC #CCL 89) by extraction with RNAzol (Biotecx; Houston Tex.) following manufacturer's procedures and purification of the mRNA by oligo dT cellulose chromatography using an oligo dT mRNA kit (Qiagen) using standard procedures. mRNA was also extracted as described above from a variety of human cell lines obtained from the American Type Culture Collection (Rockville Md.). Northern blotting was performed using these various mRNAs and hybridization with a $^{32}$P-labeled rat RIZ (representing a.a. positions 245–883) according to standard procedures (Sambrook et. al., supra, 1989).

Figure 11A:
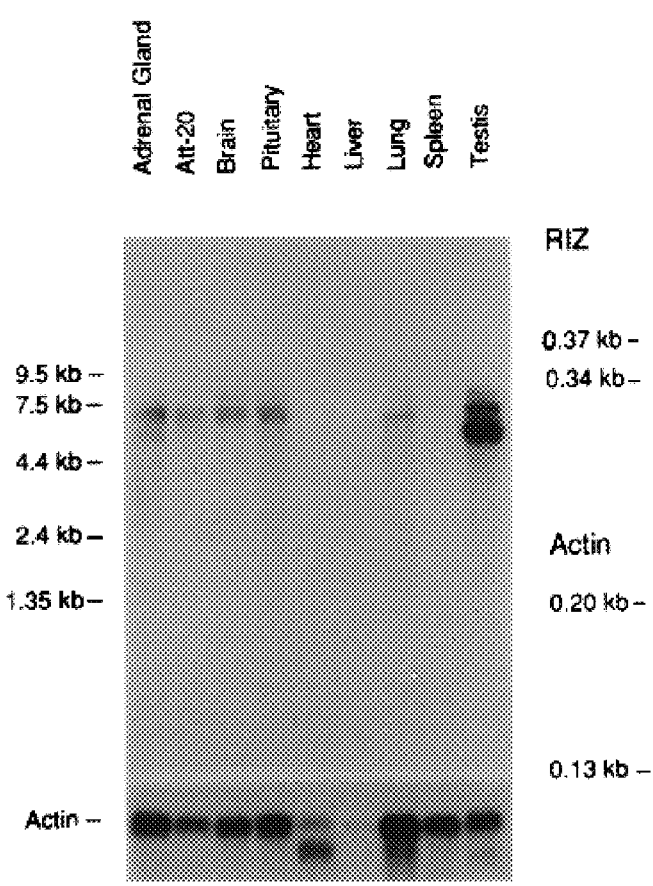
FIGS. 11A and 11B show RIZ mRNA expression in adult and fetal rat tissues, as indicated. Relative amounts of RNA loaded were compared by probing for Actin (see bottom of each blot). Numbers to the left of each figure indicate position of molecular weight markers as indicated (Kb: kilobases).

Northern blotting showed a major 7.2 kb major RIZ mRNA species primarily localized to rat neuroendocrine tissues (FIG. 11A). The testes showed a 5 kb mRNA species, which is smaller than the RIZ mRNA detected in the other organs or tissues.

Figure 11B:
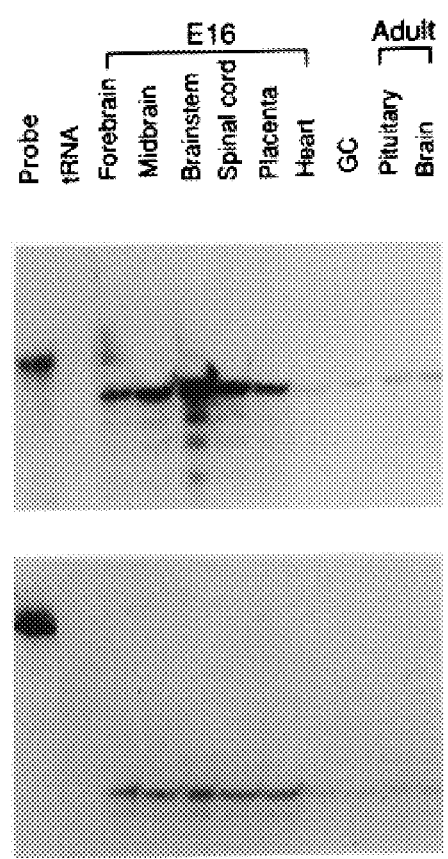

Further evaluation of mRNA expression was performed using an RNase protection method. The method was performed according to standard procedures using a $^{32}$P-labeled rat RIZ (representing a.a. position 463–574) as the probe. The results showed abundant levels of RIZ mRNA in various neural tissues of a 16 day rat fetus as well as the placenta (FIG. 11B). In contrast, little if any mRNA was detected in adult rat tissues by this method.

Figure 12:
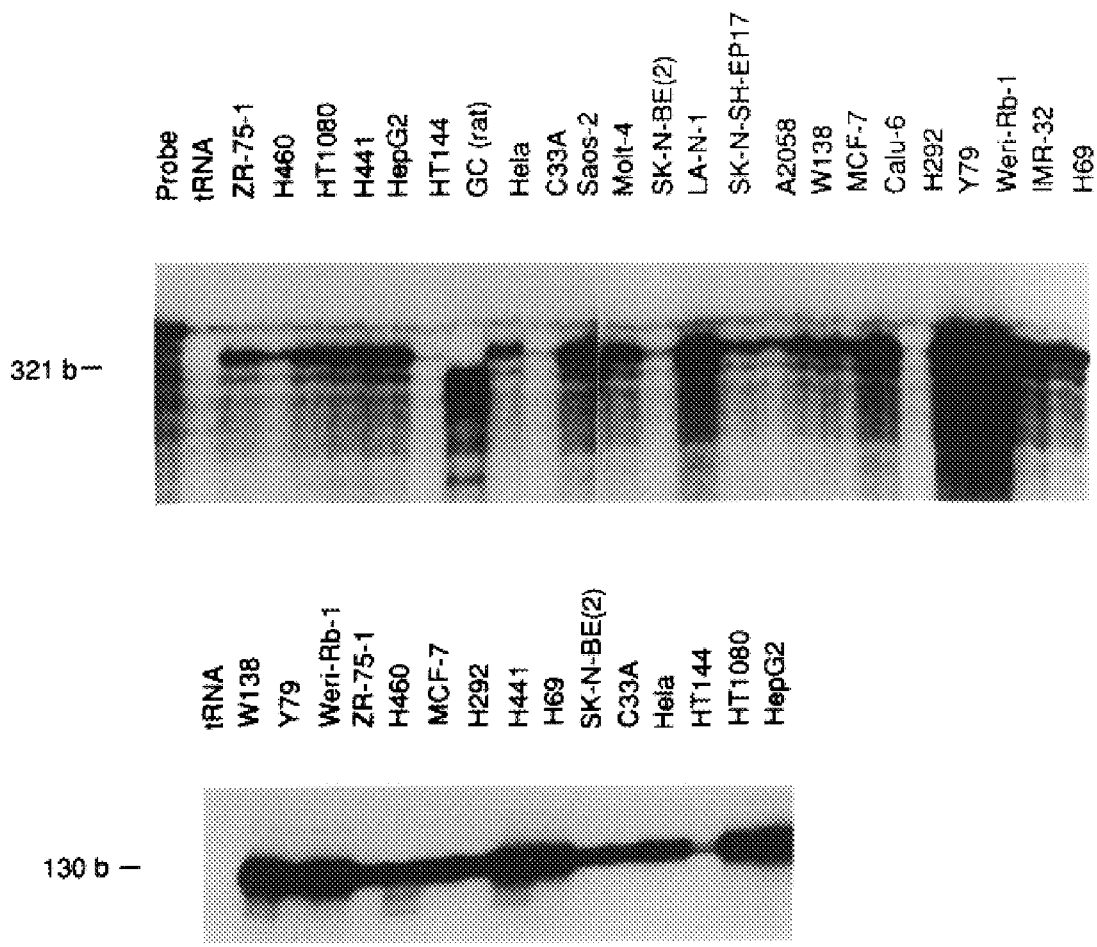
FIG. 12 presents an RNase protection experiment using mRNA from various human cell lines and from a rat cell line (indicated as GC). The 321 base pair marker (321 b) indicates protection of $^{32}$P-labeled rat RIZ (a.a. position 457–579) while the 130 base pair marker (130 b) indicates protection of Actin.

RNase protection showed that RIZ mRNA was detectable in the human retinoblastoma cell lines, Y79 and Weri-Rb-1, with lower levels of detection in a variety of other human cell lines (FIG. 12). These results indicate that RIZ mRNA is expressed in large amounts in neuroendocrine related tissues of mammals and can be involved in fetal development.

Several segments of human RIZ cDNA, encompassing the full length coding region were used as probes to screen a human placental genomic cosmid library to isolate the RIZ gene. Several genomic clones were isolated and the segments encoding RIZ were localized within the clones by restriction mapping and nucleotide sequencing. The genomic clones showed that the sequence encoding RIZ is distributed across eight exons in the gene, with the majority of RIZ sequence (4.3 kb) contained in exon 7.

EXAMPLE VI

Analysis of the RIZ Gene in Normal and Tumor Cells

This example provides methods to detect the RIZ gene by direct chromosomal analysis and to evaluate mutations in the RIZ gene in tumor cells.

A. Chromosomal Localization of the Human RIZ Gene

A cosmid clone with a 35 kb insert that contains exons 7 and 8 was used as a probe for fluorescence in situ hybridization (FISH) on R-banded metaphase chromosomes to detect the chromosomal localization of the human RIZ gene. The method for FISH was performed as described previously (Takahashi et al., Hum. Genet. 88:119–121 (1991), which is incorporated herein by reference). Cot-1 DNA (BRL; Gaithersburg Md.) was used for the suppression of repetitive sequences present in this clone according to methods described by Lichter et al., (Lichter et. al., Proc. Natl. Acad. Sci., USA 87:6634–6638 (1990), which is incorporated herein by reference) using a 20 fold excess of Cot-1 DNA. Ektachrome film (Kodak, ASA100) was used for the microphotography (filter combination, Nikon B-2A).

Of 100 R-banded metaphase plates evaluated by the FISH method, 52 plates showed hybridization of the probe to both chromatids of chromosome 1 at band p36.13–p36.23, 44 plates showed hybridization of the probe only to one chromatid of chromosome 1, and four plates showed no hybridization.

Further localization of the RIZ gene to chromosome 1p36 was accomplished at the molecular level by YAC cloning. A CEPH-derived human mega-YAC library (CEPH, France) was screened by PCR using two oligonucleotide primers to amplify a 290 bp fragment within the RIZ exon 7. YAC DNA was amplified in a total volume of 10 µl containing 1×PCR buffer (50 mM KCl/10 mM Tris-HCl, pH 8.3/1.5 mM MgCl$_2$), 200 µM of each dNTP, 0.3 µM of each primer (SSO 81: 5'CCAGAACCAGACGAGCGATT3' (SEQ ID NO: 92) and SSO 82: 5'AGTTCTGGGGATTTGCATG3' (SEQ ID NO: 93)), 0.2 U Taq DNA polymerase (Perkin Elmer, Norwalk, Conn.). One of the primers was end-labeled using $^{32}$P-γ-ATP and T4 polynucleotide kinase. The PCR fragments were analyzed by acrylamide gel electrophoresis followed by autoradiography.

PCR screening of the CEPH human mega-YAC library for RIZ gene sequences identified two YAC clones, 796H4 and 807H7. A search of Genethon human genome database (Genethon; Paris France) showed that the clones contained the polymorphic marker D1S228, which maps to chromosome 1p36 (Gyapay et al., Nat. Genet. 7:246–339 (1994); Weissenbach et al., Nature 359:794–801 (1992) and Cohen et al., Nature 366:698–701 (1993), each of which is incorporated herein by reference)). Thus, these results indicate that the RIZ gene is localized to chromosome 1p36.

B. Allele-Specific RIZ Expression in Human Melanoma Cells

Genomic DNA from blood and placental samples of normal subjects and tumor cell lines were prepared by incubating cells for 1 hr at 55° C. in 50 mM Tris-HCl, pH 8.0/100 mM EDTA/0.5% SDS/500 µg/ml Proteinase K. After phenol/chloroform and chloroform extraction, the DNA was precipitated. RNA was prepared from a pellet of 5–10×10$^6$ PBS washed cells or from fetal tissues using RNAzol (Biotecx Laboratories; Houston Tex.).

Southern blots were performed on melanoma cell DNA using a 1 kb human RIZ cDNA probe (1.1). The results showed identification of the appropriate sized bands for the RIZ gene in the melanoma cells, indicating no gross abnormalities in the RIZ gene in these cells.

To determine whether both alleles of RIZ were active in melanoma cells, the frequencies of the two allelic variants of RIZ were determined for melanoma and compared with the frequency in the population. RIZ genotyping was performed by amplification of a 290 bp fragment representing RIZ (a.a. residues from about 230–330) using PCR on genomic DNA isolated from 28 normal individuals and 69 human melanoma cell lines. PCR amplification of the 290 bp fragment was performed on 100 ng of genomic DNA in a total volume of 50 µl containing 1× PCR buffer, 200 µM of each dNTP, 0.3 µM of each primer (SSO 81+SSO 82), and 1 U of Taq DNA polymerase (Perkin Elmer). The PCR product was sequenced to determine the codons encoding RIZ a.a. position 283. The RIZ D283 allele encodes an Asp residue at a.a. position 283 by the codon GAT, while the RIZ E283 allele encodes a Glu residue at a.a. position 283 by the codon GAA.

Genotyping of DNA from 28 normal individuals showed that fifteen were homozygous for the RIZ D283 allele (53%) three were homozygous for the E283 allele (10%) and ten were heterozygous (35%). Thus, the overall frequency of the RIZ E283 allele in the population of normal individuals studies was estimated to be about 28.5%.

Genotyping the DNA of 69 melanoma cell lines showed that 40 were homozygous for the RIZ D283 allele (58%), nine were homozygous for RIZ E283 (13%) and 20 were heterozygous (29%).

RNA samples from the 20 heterozygous melanoma cell lines were sequenced to determine if both alleles were transcribed in the cell or if only one allele was transcribed (ie. monoallelic expression). Sequencing was performed on DNA products produced by reverse transcription-PCR (RT-PCR) amplification using specific RIZ primers. RT-PCR amplification was performed according to the manufacturer's instructions (GeneAmp RNA PCR kit; Perkin Elmer). A 640 bp fragment encoding RIZ exons 5–7 was obtained from transcription of 1 µg of total RNA using the SSO 82 primer (SEQ ID NO: 93) and PCR amplification using the SSO 24 primer (5'GCGAGGAGCTCCTGGTCTGG3'; SEQ ID NO: 106) and the SSO 82 primer (SEQ ID NO: 93). The amplified fragment was gel purified and sequenced using primer SSO 82 and a CircumVent™ Thermal Cycle DNA Sequencing kit (New England Biolabs; Beverly Mass.). The sequencing products were analyzed on a 6% sequencing gel.

Sequencing of amplified and transcribed RIZ mRNA from 20 heterozygous melanoma cell lines showed that transcripts representing one of the RIZ alleles were reduced or absent in four of the cell lines. These cell lines were D283/E283 RIZ heterozygotes (ie. designated 5-5/6-4). The D283 allele transcript was not detected in SK-MEL-14 cells (ATCC) while the E283 RIZ transcript was not detected in WM983C and WM1361C cell lines. The SK-MEL-23 cell line expressed reduced levels of the D283 RIZ allele. In contrast to the melanoma results, sequencing of amplified and transcribed mRNA from RIZ heterozygotes representing seven non-melanoma cell lines and two normal human placental tissues showed no loss or reduction of RIZ alelic expression.

The 4 melanoma cell lines heterozygous for RIZ were evaluated to determine the amount of RIZ protein produced by the cells. RIZ protein level was estimated qualitatively by immunoprecipitation of RIZ from cell extracts with anti-RIZ antibody followed by immunoblotting the isolated RIZ with the anti-RIZ antibody. The melanoma cell line SK-MEL-23 produced about 50% less RIZ protein than the other melanoma cell lines tested. These data indicate that the reduction in expression of the RIZ D283 allele in SK-MEL-23 resulted in a decrease in overall expression of RIZ protein in the cell.

The SK-MEL-23 melanoma cell line was cultured for 3 to 6 days with 3 uM of the demethylating agent 5-azacytidine. The reduced expression of the RIZ D283 transcripts in these cells was unaffected, indicating that the reduced levels of RIZ transcription were not due to increased DNA methylation.

SK-MEL-23 melanoma cells were transfected with an expression vector encoding full length RIZ cDNA (pCMVRIZ)to determine if increasing the level of RIZ expression can reduce the growth potential of the cells. RIZ transfected SK-MEL-23 cells showed increased expression of RIZ in the cell nucleus by immunostaining with monoclonal antibody D27 and, showed a reduced ability to form colonies in vitro. These results indicate increasing the level of RIZ in tumor cells that are deficient in RIZ expression can reduce the growth of the tumor cells.

EXAMPLE VII

RIZ Protein Represses Transcription

This example demonstrates that RIZ or an active fragment of a RIZ can repress transcription.

A fusion protein containing RIZ or deletion mutants of RIZ fused to the DNA binding domain of GAL4 was produced by subcloning the rat RIZ cDNA (SEQ ID NO: 1) or portions thereof into the plasmid pSG424 (Sadowski and Ptashne, *Nucl. Acids Res.* 17:7359 (1989), which is incorporated herein by reference). The plasmid encoding the RIZ/GAL4 fusion protein was transfected into CV1 cells, COS cells or C33A cells (ATCC) along with a plasmid containing a CAT reporter gene linked to the thymidine kinase promoter and GAL4 promotor (Shi et al., *Cell* 67:377–388 (1991), which is incorporated herein by reference).

Reporter gene (CAT) expression was decreased in cells transfected with the RIZ/GAL4 (containing RIZ a.a. 17–1706; SEQ ID NO: 2) as compared to the level of CAT expression in cells transfected with plasmid pSG424, but lacking the RIZ sequence. The repressor activity of RIZ was mapped to amino acids 17 to 900 from the amino terminus (SEQ ID NO: 2). The PR domain is required for transcriptional repression but, alone, is not sufficient for full repressor activity; a region between a.a. positions 573 to 900 also is required. These results demonstrate that RIZ or an active fragment thereof can act as a transcriptional regulator. Furthermore, the transcriptional repressor role of RIZ is independent of the regulatory effect RIZ has due to its interaction with Rb protein because C33A cells that were repressed by RIZ/GAL4 do not express Rb.

CAT reporter activity was decreased by transfection of RIZ/GAL4 containing amino acids 71–1706 (SEQ ID NO:2), however the amount of repressor activity was less than the RIZ/GAL4 containing RIZ amino acids 17–1706 (SEQ ID NO: 2). This result indicates that the PR domain is involved in RIZ-mediated transcriptional regulation and that absense of block A of the PR domain reduces but does not eliminate the RIZ repressor activity.

Although the invention has been described with reference to the above-provided examples, it should be understood that various modifications can be made without departing from the spirit of the invention. Accordingly, the invention is limited only by the claims that follow.

---

I claim:

1. A substantially purified PR domain peptide, comprising an amino acid sequence selected from the group consisting of amino acid positions 50 to 61 of RIZ (SEQ ID NO: 99), amino acid positions 88 to 99 of RIZ (SEQ ID NO: 99), amino acid positions 134 to 144 of RIZ (SEQ ID NO: 99), amino acid positions 71 to 82 of PRDI-BF1 (SEQ ID NO: 98), amino acid positions 71 to 82 of EVI-1 (SEQ ID NO: 100), amino acid positions 29 to 40 of egl-43 (SEQ ID NO: 101), amino acid positions 112 to 123 of PRDI-BF1(SEQ ID NO: 98), amino acid positions 108 to 119 of EVI-1 (SEQ ID NO: 100), amino acid positions 66 to 77 of egl-43 (SEQ ID NO: 101), amino acid positions 158 to 167 of PRDI-BF1 (SEQ ID NO: 98), amino acid positions 154 to 164 of EVI-1 (SEQ ID NO: 100), amino acid positions 108 to 117 of egl-43 (SEQ ID NO: 101) and amino acid positions 36 to 151 of SEQ ID NO: 2.

2. The PR domain peptide of claim 1, wherein said amino acid sequence is amino acid positions 50 to 61 of RIZ (SEQ ID NO: 99).

3. The PR domain peptide of claim 1, wherein said amino acid sequence is amino acid positions 88 to 99 of RIZ (SEQ ID NO: 99).

4. The PR domain peptide of claim 1, wherein said amino acid sequence is amino acid positions 134 to 144 of RIZ (SEQ ID NO: 99).

5. The PR domain peptide of claim 1, wherein said amino acid sequence is amino acid positions 71 to 82 of PRDI-BF1 (SEQ ID NO: 98).

6. The PR domain peptide of claim 1, wherein said amino acid sequence is amino acid positions 71 to 82 of EVI-1 (SEQ ID NO: 100).

7. The PR domain peptide of claim 1, wherein said amino acid sequence is amino acid positions 29 to 40 of egl-43 (SEQ ID NO: 101).

8. The PR domain peptide of claim 1, wherein said amino acid sequence is amino acid positions 112 to 123 of PRDI-BF1(SEQ ID NO: 98).

9. The PR domain peptide of claim 1, wherein said amino acid sequence is amino acid positions 108 to 119 of EVI-1 (SEQ ID NO: 100).

10. The PR domain peptide of claim 1, wherein said amino acid sequence is amino acid positions 66 to 77 of egl-43 (SEQ ID NO: 101).

11. The PR domain peptide of claim 1, wherein said amino acid sequence is amino acid positions 158 to 167 of PRDI-BF1 (SEQ ID NO: 98).

12. The PR domain peptide of claim 1, wherein said amino acid sequence is amino acid positions 154 to 164 of EVI-1 (SEQ ID NO: 100).

13. The PR domain peptide of claim 1, wherein said amino acid sequence is amino acid positions 108 to 117 of egl-43 (SEQ ID NO: 101).

14. The PR domain peptide of claim 1, wherein said amino acid sequence is amino acid positions 36 to 151 of SEQ ID NO: 2.

15. The PR domain peptide of claim 1, wherein said amino acid sequence is SEQ ID NO: 98.

16. The PR domain peptide of claim 1, wherein said amino acid sequence is SEQ ID NO: 99.

17. The PR domain peptide of claim 1, wherein said amino acid sequence is SEQ ID NO: 100.

18. The PR domain peptide of claim 1, wherein said amino acid sequence is SEQ ID NO: 101.

* * * * *

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
        (A) LENGTH: 6171 base pairs
        (B) TYPE: nucleic acid
        (C) STRANDEDNESS: double (D) TOPOLOGY: linear (ix) FEATURE:
    (A) NAME/KEY: CDS
    (B) LOCATION: 157..5275

(xi) SEQUENCE DESCRIPTION: SEQ ID NO:1:

```
GCCAAGATGG CGGCGGCGCG GCCGCGGGCG CCAGGGCGAC GGCGGCGGCT GAGGCTCTGG      60

GCTCGCTGAA GCGTTGGCAC GTCGCGCTCT GGGCTCATGT AATCAAAGAA GTTTCTTTGT     120

TGTGTGTATC TTCACAGAAC ACAACAGGAA TTGAAA ATG CAT CAG AAC ACT GAG       174
                                        Met His Gln Asn Thr Glu
                                          1               5

TCT GTG GCA GCC ACT GAG ACT CTG GCT GAG GTA CCT GAA CAT GTG CTT      222
Ser Val Ala Ala Thr Glu Thr Leu Ala Glu Val Pro Glu His Val Leu
         10                  15                  20

CGA GGA CTT CCA GAG GAA GTA AGA CTT TTC CCA TCT GCA GTC GAC AAG      270
Arg Gly Leu Pro Glu Glu Val Arg Leu Phe Pro Ser Ala Val Asp Lys
     25                  30                  35

ACT CGG ATT GGT GTC TGG GCT ACT AAA CCA ATT TTA AAA GGG AAA AAG      318
Thr Arg Ile Gly Val Trp Ala Thr Lys Pro Ile Leu Lys Gly Lys Lys
 40                  45                  50

TTT GGG CCA TTT GTT GGT GAT AAG AAG AAG AGA TCC CAG GTT AGG AAT      366
Phe Gly Pro Phe Val Gly Asp Lys Lys Lys Arg Ser Gln Val Arg Asn
 55                  60                  65                  70

AAT GTG TAC ATG TGG GAG GTC TAC TAC CCA AAT TTG GGG TGG ATG TGC      414
Asn Val Tyr Met Trp Glu Val Tyr Tyr Pro Asn Leu Gly Trp Met Cys
             75                  80                  85

ATT GAT GCC ACC GAT CCG GAG AAG GGC AAC TGG CTA CGC TAT GTG AAC      462
Ile Asp Ala Thr Asp Pro Glu Lys Gly Asn Trp Leu Arg Tyr Val Asn
             90                  95                 100

TGG GCT TGC TCA GGA GAA GAG CAG AAT TTA TTT CCA CTG GAA ATC AAC      510
Trp Ala Cys Ser Gly Glu Glu Gln Asn Leu Phe Pro Leu Glu Ile Asn
        105                 110                 115

AGA GCC ATT TAC TAT AAA ACC TTA AAG CCA ATC GCG CCT GGC GAG GAG      558
Arg Ala Ile Tyr Tyr Lys Thr Leu Lys Pro Ile Ala Pro Gly Glu Glu
        120                 125                 130

CTC CTG GTC TGG TAC AAT GGG GAA GAC AAC CCT GAG ATA GCA GCT GCG      606
Leu Leu Val Trp Tyr Asn Gly Glu Asp Asn Pro Glu Ile Ala Ala Ala
135                 140                 145                 150

ATT GAG GAA GAG CGA GCC AGC GCC CGG AGC AAG CGG AGC TCC CCG AAG      654
Ile Glu Glu Glu Arg Ala Ser Ala Arg Ser Lys Arg Ser Ser Pro Lys
                155                 160                 165

AGC CGC AGA GGG AAG AAG AAA TCA CAC GAG AAC AAA AAC AAA GGC ATC      702
Ser Arg Arg Gly Lys Lys Lys Ser His Glu Asn Lys Asn Lys Gly Ile
                170                 175                 180

AGA ACC CAC CCC ACA CAG CTG AAG GCA AGT GAG CTG GAC TCT ACC TTT      750
Arg Thr His Pro Thr Gln Leu Lys Ala Ser Glu Leu Asp Ser Thr Phe
            185                 190                 195

GCA AAC ATG AGG GGC TCT GCA GAA GGT CCA AAA GAA GAG GAT GAG AGG      798
Ala Asn Met Arg Gly Ser Ala Glu Gly Pro Lys Glu Glu Asp Glu Arg
200                 205                 210

CCT TTG GCT TCG GCA CCT GAG CAG CCA GCC CCT CTG CCG GAG GTG GGG      846
Pro Leu Ala Ser Ala Pro Glu Gln Pro Ala Pro Leu Pro Glu Val Gly
215                 220                 225                 230

AAT CAA GAT GCA GTT CCA CAG GTG GCC ATC CCT CTC CCT GCC TGC GAG      894
Asn Gln Asp Ala Val Pro Gln Val Ala Ile Pro Leu Pro Ala Cys Glu
                235                 240                 245

CCA CAG CCA GAG GTA GAT GGG AAA CAA GAA GTC ACA GAC TGT GAG GTC      942
Pro Gln Pro Glu Val Asp Gly Lys Gln Glu Val Thr Asp Cys Glu Val
            250                 255                 260
```

```
AAT GAT GTG GAG GAA GAG GAG CTG GAA GAG GAA GAG GAG CTG GAA GAG          990
Asn Asp Val Glu Glu Glu Glu Leu Glu Glu Glu Glu Glu Leu Glu Glu
            265                 270                 275

GAG GAG GAG GAG GAG TTG GGA GAA GAT GGG GTA GAA GAA GCA GAC ATG         1038
Glu Glu Glu Glu Glu Leu Gly Glu Asp Gly Val Glu Glu Ala Asp Met
        280                 285                 290

CCG AAT GAA AGC TCT GCG AAA GAG CCG GAG ATC CGG TGT GAA GAA AAG         1086
Pro Asn Glu Ser Ser Ala Lys Glu Pro Glu Ile Arg Cys Glu Glu Lys
295                 300                 305                 310

CCA GAA GAC TTA TTA GAA GAG CCA CAG AGC ATG TCG AAT GAA GCT CGT         1134
Pro Glu Asp Leu Leu Glu Glu Pro Gln Ser Met Ser Asn Glu Ala Arg
                315                 320                 325

GAA GAC TCT CCA GAC GTG ACC CCT CCT CCC CAC ACT CCC AGA GCT AGA         1182
Glu Asp Ser Pro Asp Val Thr Pro Pro Pro His Thr Pro Arg Ala Arg
            330                 335                 340

GAG GAG GCC AAC GGT GAT GTA CTT GAG ACA TTT ATG TTT CCG TGT CAG         1230
Glu Glu Ala Asn Gly Asp Val Leu Glu Thr Phe Met Phe Pro Cys Gln
        345                 350                 355

CAC TGT GAA AGA AAA TTT GCA ACG AAG CAG GGG CTA GAG CGT CAC ATG         1278
His Cys Glu Arg Lys Phe Ala Thr Lys Gln Gly Leu Glu Arg His Met
    360                 365                 370

CAC ATC CAC ATT TCT ACC ATC AAT CAT GCT TTC AAG TGC AAG TAC TGT         1326
His Ile His Ile Ser Thr Ile Asn His Ala Phe Lys Cys Lys Tyr Cys
375                 380                 385                 390

GGG AAA CGG TTT GGC ACA CAG ATT AAC AGG AGG CGG CAT GAA CGG CGC         1374
Gly Lys Arg Phe Gly Thr Gln Ile Asn Arg Arg Arg His Glu Arg Arg
                395                 400                 405

CAC GAA ACG GGG TTG AAG AGA AGA CCC AGC ATG ACT TTA CAG TCC TCA         1422
His Glu Thr Gly Leu Lys Arg Arg Pro Ser Met Thr Leu Gln Ser Ser
            410                 415                 420

GAG GAT CCA GAT GAT GGC AAG GGG GAA AAT GTT ACT TCT AAA GAT GAG         1470
Glu Asp Pro Asp Asp Gly Lys Gly Glu Asn Val Thr Ser Lys Asp Glu
        425                 430                 435

TCA AGT CCA CCT CAA CTC GGG CAA GAC TGT TTG ATA TTG AAC TCA GAG         1518
Ser Ser Pro Pro Gln Leu Gly Gln Asp Cys Leu Ile Leu Asn Ser Glu
    440                 445                 450

AAA ACC TCA CAG GAA GTA CTG AAT TCA TCT TTT GTG GAA GAA AAT GGT         1566
Lys Thr Ser Gln Glu Val Leu Asn Ser Ser Phe Val Glu Glu Asn Gly
455                 460                 465                 470

GAA GTT AAA GAA CTT CAT CCG TGC AAA TAC TGC AAA AAG GTA TTT GGA         1614
Glu Val Lys Glu Leu His Pro Cys Lys Tyr Cys Lys Lys Val Phe Gly
                475                 480                 485

ACT CAC ACC AAT ATG AGA CGA CAT CAG CGT AGA GTT CAT GAG CGC CAC         1662
Thr His Thr Asn Met Arg Arg His Gln Arg Arg Val His Glu Arg His
            490                 495                 500

CTG ATT CCC AAA GGT GTC AGG CGA AAA GGA GGA CTT CTG GAA GAG CCA         1710
Leu Ile Pro Lys Gly Val Arg Arg Lys Gly Gly Leu Leu Glu Glu Pro
        505                 510                 515

CAG CCA CCA GCA GAG CAG GCT CCA CCC TCC CAG AAT GTC TAT GTC CCA         1758
Gln Pro Pro Ala Glu Gln Ala Pro Pro Ser Gln Asn Val Tyr Val Pro
    520                 525                 530

AGC ACA GAG CCA GAG GAG GAA GGG GAA ACA GAT GAC GTG TAC ATC ATG         1806
Ser Thr Glu Pro Glu Glu Glu Gly Glu Thr Asp Asp Val Tyr Ile Met
535                 540                 545                 550

GAC ATT TCT AGC AAC ATC TCT GAA AAC CTA AAT TAC TAT ATT GAC GGT         1854
Asp Ile Ser Ser Asn Ile Ser Glu Asn Leu Asn Tyr Tyr Ile Asp Gly
                555                 560                 565

AAG ATT CAG ACC AAC AGC AGC ACT AGT AAC TGT GAT GTG ATT GAG ATG         1902
Lys Ile Gln Thr Asn Ser Ser Thr Ser Asn Cys Asp Val Ile Glu Met
```

-continued

```
             570                 575                 580
GAG TCT AAT TCT GCA CAC TTG TAT GGC ATA GAC TGT CTG CTC ACT CCA    1950
Glu Ser Asn Ser Ala His Leu Tyr Gly Ile Asp Cys Leu Leu Thr Pro
            585                 590                 595

GTG ACC GTG GAG ATT ACT CAG AAC ATA AAG AGC ACT CAG GTC TCT GTG    1998
Val Thr Val Glu Ile Thr Gln Asn Ile Lys Ser Thr Gln Val Ser Val
600                 605                 610

ACA GAT GAT CTT CTC AAA GAC TCT CCC AGC AGC ACA AAT TGT GAG TCT    2046
Thr Asp Asp Leu Leu Lys Asp Ser Pro Ser Ser Thr Asn Cys Glu Ser
615                 620                 625                 630

AAG AAA CGG AGG ACT GCC AGT CCA CCT GTG CTC CCC AAA ATT AAA ACG    2094
Lys Lys Arg Arg Thr Ala Ser Pro Pro Val Leu Pro Lys Ile Lys Thr
                635                 640                 645

GAG ACG GAG TCT GAT TCC ACA GCA CCC TCG TGT TCC TTA AGT CTG CCC    2142
Glu Thr Glu Ser Asp Ser Thr Ala Pro Ser Cys Ser Leu Ser Leu Pro
            650                 655                 660

CTG AGC ATA TCC ACA GCC GAG GTG GTG TCC TTC CAT AAA GAG AAG GGC    2190
Leu Ser Ile Ser Thr Ala Glu Val Val Ser Phe His Lys Glu Lys Gly
            665                 670                 675

GTC TAT TTG TCG TCC AAG CTC AAG CAG CTT CTT CAG ACC CAG GAC AAG    2238
Val Tyr Leu Ser Ser Lys Leu Lys Gln Leu Leu Gln Thr Gln Asp Lys
            680                 685                 690

CTG ACC CTT CCT GCA GGG TTT TCA GCA GCT GAG ATT CCT AAG TTA GGT    2286
Leu Thr Leu Pro Ala Gly Phe Ser Ala Ala Glu Ile Pro Lys Leu Gly
695                 700                 705                 710

CCC GTG TGC GCG TCT GCT CCT GCA TCC ATG TTG CCC GTG ACC TCT AGT    2334
Pro Val Cys Ala Ser Ala Pro Ala Ser Met Leu Pro Val Thr Ser Ser
                715                 720                 725

AGG TTT AAG AGA CGC ACC AGC TCT CCA CCG AGC TCT CCA CAG CAC AGC    2382
Arg Phe Lys Arg Arg Thr Ser Ser Pro Pro Ser Ser Pro Gln His Ser
            730                 735                 740

CCT GCC CTT CGA GAC TTC GGG AAA CCA AAT GAT GGG AAA GCA GCA TGG    2430
Pro Ala Leu Arg Asp Phe Gly Lys Pro Asn Asp Gly Lys Ala Ala Trp
            745                 750                 755

ACA GAC ACA GTC CTG ACT TCC AAG AAA CCC AAG TTA GAA AGT CGT AGT    2478
Thr Asp Thr Val Leu Thr Ser Lys Lys Pro Lys Leu Glu Ser Arg Ser
760                 765                 770

GAC TCA CCA GCA TGG AGT TTG TCT GGG AGA GAT GAA AGA GAA ACC GGA    2526
Asp Ser Pro Ala Trp Ser Leu Ser Gly Arg Asp Glu Arg Glu Thr Gly
775                 780                 785                 790

AGC CCT CCT TGC TTT GAT GAA TAC AAA ATA TCA AAG GAA TGG GCA GCC    2574
Ser Pro Pro Cys Phe Asp Glu Tyr Lys Ile Ser Lys Glu Trp Ala Ala
                795                 800                 805

AGT TCT ACT TTC AGC AGT GTG TGC AAC CAA CAG CCA TTG GAT TTA TCC    2622
Ser Ser Thr Phe Ser Ser Val Cys Asn Gln Gln Pro Leu Asp Leu Ser
            810                 815                 820

AGC GGG GTC AAA CAG AAG TCA GAG GGC ACA GGC AAG ACT CCA GTC CCA    2670
Ser Gly Val Lys Gln Lys Ser Glu Gly Thr Gly Lys Thr Pro Val Pro
            825                 830                 835

TGG GAA TCT GTA TTG GAT CTC AGT GTG CAT AAA AAG CCT TGC GAT TCT    2718
Trp Glu Ser Val Leu Asp Leu Ser Val His Lys Lys Pro Cys Asp Ser
            840                 845                 850

GAA GGC AAG GAA TTC AAA GAG AAC CAT TTG GCA CAG CCA GCT GCA AAG    2766
Glu Gly Lys Glu Phe Lys Glu Asn His Leu Ala Gln Pro Ala Ala Lys
855                 860                 865                 870

AAG AAA AAA CCA ACC ACC TGT ATG CTT CAA AAG GTT CTT CTC AAT GAG    2814
Lys Lys Lys Pro Thr Thr Cys Met Leu Gln Lys Val Leu Leu Asn Glu
                875                 880                 885

TAT AAT GGT GTT AGC TTA CCT ACA GAA ACC ACA CCA GAG GTG ACC AGG    2862
```

-continued

```
                    Tyr Asn Gly Val Ser Leu Pro Thr Glu Thr Thr Pro Glu Val Thr Arg
                            890                 895                 900
AGC CCA AGT CCT TGT AAA TCC CCA GAT ACA CAG CCA GAT CCT GAA CTT              2910
Ser Pro Ser Pro Cys Lys Ser Pro Asp Thr Gln Pro Asp Pro Glu Leu
            905                 910                 915

GGT CCT GAC TCA AGT TGC TCA GTC CCC ACT GCT GAG TCT CCA CCT GAA              2958
Gly Pro Asp Ser Ser Cys Ser Val Pro Thr Ala Glu Ser Pro Pro Glu
920                 925                 930

GTT GTT GGC CCT TCC TCA CCC CCT CTC CAG ACA GCC TCC TTA TCC TCC              3006
Val Val Gly Pro Ser Ser Pro Pro Leu Gln Thr Ala Ser Leu Ser Ser
935                 940                 945                 950

GGT CAG CTG CCT CCT CTC TTA ACC CCC ACA GAG CCT TCT TCC CCT CCC              3054
Gly Gln Leu Pro Pro Leu Leu Thr Pro Thr Glu Pro Ser Ser Pro Pro
                    955                 960                 965

CCC TGC CCT CCT GTG TTA ACT GTT GCC ACT CCA CCA CCT CCC CTC CTT              3102
Pro Cys Pro Pro Val Leu Thr Val Ala Thr Pro Pro Pro Pro Leu Leu
                970                 975                 980

CCA ACC GTC CCT CTC TCC CAC CCC TCT TCT GAT GCC TCC CCT CAG CAG              3150
Pro Thr Val Pro Leu Ser His Pro Ser Ser Asp Ala Ser Pro Gln Gln
            985                 990                 995

TGT CCC TCT CCG TTC TCA AAC ACC ACT GCT CAG TCT CCT CTT CCC ATT              3198
Cys Pro Ser Pro Phe Ser Asn Thr Thr Ala Gln Ser Pro Leu Pro Ile
        1000                1005                1010

CTC TCC CCA ACA GTG TCT CCC TCT CCC TCT CCC ATT CCT CCT GTA GAG              3246
Leu Ser Pro Thr Val Ser Pro Ser Pro Ser Pro Ile Pro Pro Val Glu
1015                1020                1025                1030

CCA CTT ATG TCT GCT GCT TCC CCT GGT CCC CCA ACA CTT TCT TCC TCC              3294
Pro Leu Met Ser Ala Ala Ser Pro Gly Pro Pro Thr Leu Ser Ser Ser
                1035                1040                1045

TCC TCT TCT TCC TCT TCC TTC CCT TCC TCT TCC TGC TCC TCC ACC TCC              3342
Ser Ser Ser Ser Ser Ser Phe Pro Ser Ser Ser Cys Ser Ser Thr Ser
            1050                1055                1060

CCC TCC CCA CCC CCT CTT TCA GCA GTG TCA TCT GTG GTT TCC TCT GGG              3390
Pro Ser Pro Pro Pro Leu Ser Ala Val Ser Ser Val Val Ser Ser Gly
        1065                1070                1075

GAC AAC CTG GAG GCA TCT CTG CCT GCA GTA ACT TTC AAA CAG GAG GAG              3438
Asp Asn Leu Glu Ala Ser Leu Pro Ala Val Thr Phe Lys Gln Glu Glu
    1080                1085                1090

TCA GAG AGT GAA GGT CTG AAA CCC AAG GAA GAG GCC CCA CCT GCA GGG              3486
Ser Glu Ser Glu Gly Leu Lys Pro Lys Glu Glu Ala Pro Pro Ala Gly
1095                1100                1105                1110

GGA CAG AGT GTG GTC CAA GAA ACA TTC AGC AAA AAC TTC ATT TGC AAT              3534
Gly Gln Ser Val Val Gln Glu Thr Phe Ser Lys Asn Phe Ile Cys Asn
                1115                1120                1125

GTC TGT GAA TCG CCT TTT CTT TCC ATT AAA GAC CTA ACC AAA CAT TTA              3582
Val Cys Glu Ser Pro Phe Leu Ser Ile Lys Asp Leu Thr Lys His Leu
            1130                1135                1140

TCC GTC CAT GCT GAA GAG TGG CCC TTC AAA TGT GAG TTT TGT GTG CAG              3630
Ser Val His Ala Glu Glu Trp Pro Phe Lys Cys Glu Phe Cys Val Gln
        1145                1150                1155

CTG TTT AAG GTT AAG ACT GAT CTA TCA GAG CAT CGA TTT CTG CTT CAT              3678
Leu Phe Lys Val Lys Thr Asp Leu Ser Glu His Arg Phe Leu Leu His
    1160                1165                1170

GGG GTT GGA AAT ATC TTT GTG TGT TCT GTA TGT AAG AAA GAA TTT GCC              3726
Gly Val Gly Asn Ile Phe Val Cys Ser Val Cys Lys Lys Glu Phe Ala
1175                1180                1185                1190

TTC TTA TGC AAT CTG CAG CAG CAC CAG CGT GAT CTC CAC CCA GAT GAG              3774
Phe Leu Cys Asn Leu Gln Gln His Gln Arg Asp Leu His Pro Asp Glu
                1195                1200                1205
```

```
GTA TGC ACA CAC CAC GAG TTT GAA AGT GGG ACC CTG AGG CCC CAG AAC    3822
Val Cys Thr His His Glu Phe Glu Ser Gly Thr Leu Arg Pro Gln Asn
         1210                1215                1220

TTC ACA GAC CCC AGC AAG GCC AAT GTT GAG CAT ATG CCA AGT TTG CCA    3870
Phe Thr Asp Pro Ser Lys Ala Asn Val Glu His Met Pro Ser Leu Pro
         1225                1230                1235

GAA GAG CCT TTA GAA ACT TCT AGA GAG GAG GAG TTA AAT GAT TCC TCT    3918
Glu Glu Pro Leu Glu Thr Ser Arg Glu Glu Glu Leu Asn Asp Ser Ser
         1240                1245                1250

GAA GAG CTT TAC ACG ACC ATC AAA ATA ATG GCT TCT GGA ATA AAG ACG    3966
Glu Glu Leu Tyr Thr Thr Ile Lys Ile Met Ala Ser Gly Ile Lys Thr
1255                1260                1265                1270

AAG GAT CCA GAT GTT CGA CTT GGT CTC AAC CAG CAC TAC CCG AGC TTT    4014
Lys Asp Pro Asp Val Arg Leu Gly Leu Asn Gln His Tyr Pro Ser Phe
                 1275                1280                1285

AAA CCT CCT CCA TTT CAG TAC CAC CAT CGA AAC CCT ATG GGG ATA GGG    4062
Lys Pro Pro Pro Phe Gln Tyr His His Arg Asn Pro Met Gly Ile Gly
             1290                1295                1300

GTG ACA GCC ACC AAC TTC ACC ACC CAC AAT ATT CCA CAG ACT TTC ACT    4110
Val Thr Ala Thr Asn Phe Thr Thr His Asn Ile Pro Gln Thr Phe Thr
         1305                1310                1315

ACT GCC ATC CGC TGC ACA AAG TGT GGG AAG GGC GTC GAC AAT ATG CCT    4158
Thr Ala Ile Arg Cys Thr Lys Cys Gly Lys Gly Val Asp Asn Met Pro
1320                1325                1330

GAG CTG CAT AAG CAT ATC TTG GCG TGT GCG TCT GCA AGT GAC AAG AAG    4206
Glu Leu His Lys His Ile Leu Ala Cys Ala Ser Ala Ser Asp Lys Lys
1335                1340                1345                1350

AGG TAC ACC CCT AAG AAA AAC CCA GTG CCC CTG AAA CAA ACT GTG CAG    4254
Arg Tyr Thr Pro Lys Lys Asn Pro Val Pro Leu Lys Gln Thr Val Gln
                 1355                1360                1365

CCC AAA AAT GGA GTG GTG GTT CTA GAC AAC TCT GGG AAA AAT GCC TTC    4302
Pro Lys Asn Gly Val Val Val Leu Asp Asn Ser Gly Lys Asn Ala Phe
             1370                1375                1380

AGA CGG ATG GGG CAG CCC AAG AGA CTG AGC TTC AAT GTT GAA CTG GGT    4350
Arg Arg Met Gly Gln Pro Lys Arg Leu Ser Phe Asn Val Glu Leu Gly
         1385                1390                1395

AAA ATG TCT CCA AAC AAG CTC AAG CTG AGT GCG CTG AAG AAG AAA AAC    4398
Lys Met Ser Pro Asn Lys Leu Lys Leu Ser Ala Leu Lys Lys Lys Asn
1400                1405                1410

CAG CTG GTG CAG AAG GCC ATC CTT CAG AAG AAC AGA GCC GCG AAG CAG    4446
Gln Leu Val Gln Lys Ala Ile Leu Gln Lys Asn Arg Ala Ala Lys Gln
1415                1420                1425                1430

AAG GCG GAC CTG AGG GAT ACT TCC GAG GCG TCC TCA CAC ATC TGC CCG    4494
Lys Ala Asp Leu Arg Asp Thr Ser Glu Ala Ser Ser His Ile Cys Pro
                 1435                1440                1445

TAC TGT GAC AGG GAG TTC ACA TAC ATT GGC AGC CTG AAT AAG CAT GCC    4542
Tyr Cys Asp Arg Glu Phe Thr Tyr Ile Gly Ser Leu Asn Lys His Ala
             1450                1455                1460

GCC TTC AGC TGT CCT AAA AAA CCT CTT TCT CCT TCC AAA AGA AAA GTT    4590
Ala Phe Ser Cys Pro Lys Lys Pro Leu Ser Pro Ser Lys Arg Lys Val
         1465                1470                1475

TCC CAT TCG TCT AAG AAA GGT GGC CAT GCA TCA TCT TCT AGC AGT GAC    4638
Ser His Ser Ser Lys Lys Gly Gly His Ala Ser Ser Ser Ser Ser Asp
         1480                1485                1490

AGA AAC AGC AGC TGC CAC CCC CGG AGG CGG ACT GCA GAT ACC GAG ATC    4686
Arg Asn Ser Ser Cys His Pro Arg Arg Arg Thr Ala Asp Thr Glu Ile
1495                1500                1505                1510

AAG ATG CAG AGC ACG CAG GCA CCC TTG GGC AAG ACC AGA GCT CGG AGT    4734
Lys Met Gln Ser Thr Gln Ala Pro Leu Gly Lys Thr Arg Ala Arg Ser
                 1515                1520                1525
```

-continued

| | |
|---|---|
| ACA GGC CCC GCC CAG GCC TCA CTG CCC TCC TCG TCC TTC AGA TCC AGA<br>Thr Gly Pro Ala Gln Ala Ser Leu Pro Ser Ser Ser Phe Arg Ser Arg<br>                          1530                          1535                            1540 | 4782 |
| CAG AAT GTC AAA TTT GCA GCT TCA GTG AAA TCC AAA AAA GCA AGC TCT<br>Gln Asn Val Lys Phe Ala Ala Ser Val Lys Ser Lys Lys Ala Ser Ser<br>            1545                          1550                          1555 | 4830 |
| TCA TCC TTG AGG AAT TCC AGT CCC ATA AGA ATG GCC AAA ATT ACT CAC<br>Ser Ser Leu Arg Asn Ser Ser Pro Ile Arg Met Ala Lys Ile Thr His<br>        1560                          1565                        1570 | 4878 |
| GTC GAG GGC AAA AAA CCC AAA GCT GTT GCC AAG AGT CAT TCT GCT CAG<br>Val Glu Gly Lys Lys Pro Lys Ala Val Ala Lys Ser His Ser Ala Gln<br>1575                      1580                        1585                        1590 | 4926 |
| CTC TCA AGC AAA TCC TCC CGA GGC CTG CAT GTC AGA GTG CAG AAG AGC<br>Leu Ser Ser Lys Ser Ser Arg Gly Leu His Val Arg Val Gln Lys Ser<br>            1595                          1600                          1605 | 4974 |
| AAA GCT GTC ATA CAG AGC AAG ACT GCC CTG GCC AGT AAG AGG AGA ACA<br>Lys Ala Val Ile Gln Ser Lys Thr Ala Leu Ala Ser Lys Arg Arg Thr<br>                1610                          1615                        1620 | 5022 |
| GAC CGG TTC ATA GTG AAA TCT AGA GAG CGC AGC GGG GGC CCA ATC ACC<br>Asp Arg Phe Ile Val Lys Ser Arg Glu Arg Ser Gly Gly Pro Ile Thr<br>              1625                          1630                        1635 | 5070 |
| CGA AGC CTT CAG CTG GCA GCT GCT GCG GAC CTG AGT GAA AGC AGG AGA<br>Arg Ser Leu Gln Leu Ala Ala Ala Ala Asp Leu Ser Glu Ser Arg Arg<br>      1640                        1645                        1650 | 5118 |
| GAG GAC AGC AGT GCC AGG CAT GAG CTG AAG GAC TTC AGC TAC AGT CTC<br>Glu Asp Ser Ser Ala Arg His Glu Leu Lys Asp Phe Ser Tyr Ser Leu<br>1655                      1660                        1665                        1670 | 5166 |
| CGC CTG GCA TCT CGA TGC GGC TCA TCA ACA GCC TCT TAC ATC ACC AGA<br>Arg Leu Ala Ser Arg Cys Gly Ser Ser Thr Ala Ser Tyr Ile Thr Arg<br>            1675                          1680                        1685 | 5214 |
| CAA TGC AGA AAG GTC AAG GCC GCC GCA GCA ACT CCG TTC CAG GGA CCC<br>Gln Cys Arg Lys Val Lys Ala Ala Ala Ala Thr Pro Phe Gln Gly Pro<br>                1690                          1695                        1700 | 5262 |
| TTC CTC AAA GAG T AGGCACTCTG TCTGCTCCTT AACAGCACCT GAAGTGACCT<br>Phe Leu Lys Glu<br>           1705 | 5315 |
| GGAATCAGTG AAGCCAAAGG GACCAGCAGT CTGCCCTGCA GAGAGCACTG ACCTCTCCCA | 5375 |
| GTTGTGAGAG TGAGAGAACG AGAGAGAGAG AGAGAGAGAG AGAGAGAGAG AGAGAGAGAG | 5435 |
| AGAATGAGAA TGTGTGTGTG TGTGTGCTGG TGCATGTGTG TGGTCTTCAA GCCAAGGTCC | 5495 |
| CAGCCTCAGG AGCAGGACCT TCCCATTTCC CGTCATCCTC TGGATGATCC TTGGACGTGG | 5555 |
| CCCAGAACCG TGCTCTGTGG TGCAGCCATC CTGCCCGGGA GGGGCATCTC CTTCTATGCA | 5615 |
| ATTTTTTTAA AGAGTTCCTT GGCCCTGCTT TGTGCTTCTT GAGCTGTCCG TTTGCCACCA | 5675 |
| CTGGGACTTG GATCTGGCCC TGAGGGGTGG GGAAGAGGGC CTATCTAAGG ATAACCTTTC | 5735 |
| AGAGGTCAAG CTCCCCTTCA TGCCACCCCT CCCCCCTGCC CTCACCGACC TTTTCCCCAC | 5795 |
| ACTGTCTCTG GGAATCAATA GCAGATAGCA TATAGATCCA TCAGGGTTGA GCCTGAACCT | 5855 |
| CGGCCCTAGC ACTAGGAAAT CCCCCTTTTC TCCCTAAGCA ACTGGAGCCG CCAGCTTTCA | 5915 |
| AGTCATTTCC TCCTTTGAGG TTCTAGAGTC CGAGAGTCTG CTCCGAAGTC TCTCCTGGGA | 5975 |
| ACCCGGGAGC CCTCGCACCC AGGACGCAGA CTCTGTGCCC ATTCTTAGAC CTGAGGTAGA | 6035 |
| AGAAGCAGTG TTTTGGGACG ATAGGGTGGA GGCGTGCCTA CTTTGTCTCC TCTGGTGGGA | 6095 |
| CCTCCTACAT CATTGGCATC TGAACCTTGC AAGTTCGCTG CAAAGAGAAG CAAAGGAAAA | 6155 |
| AAAAAAAAAA AAAAA | 6171 |

(2) INFORMATION FOR SEQ ID NO:2:

(i) SEQUENCE CHARACTERISTICS:
        (A) LENGTH: 1706 amino acids
        (B) TYPE: amino acid
        (D) TOPOLOGY: linear (ii) MOLECULE TYPE: protein (xi) SEQUENCE DESCRIPTION: SEQ ID NO:2:

```
Met His Gln Asn Thr Glu Ser Val Ala Ala Thr Glu Thr Leu Ala Glu
 1               5                  10                  15

Val Pro Glu His Val Leu Arg Gly Leu Pro Glu Glu Val Arg Leu Phe
                20                  25                  30

Pro Ser Ala Val Asp Lys Thr Arg Ile Gly Val Trp Ala Thr Lys Pro
            35                  40                  45

Ile Leu Lys Gly Lys Lys Phe Gly Pro Phe Val Gly Asp Lys Lys Lys
        50                  55                  60

Arg Ser Gln Val Arg Asn Asn Val Tyr Met Trp Glu Val Tyr Tyr Pro
 65                  70                  75                  80

Asn Leu Gly Trp Met Cys Ile Asp Ala Thr Asp Pro Glu Lys Gly Asn
                85                  90                  95

Trp Leu Arg Tyr Val Asn Trp Ala Cys Ser Gly Glu Glu Gln Asn Leu
                100                 105                 110

Phe Pro Leu Glu Ile Asn Arg Ala Ile Tyr Tyr Lys Thr Leu Lys Pro
            115                 120                 125

Ile Ala Pro Gly Glu Glu Leu Leu Val Trp Tyr Asn Gly Glu Asp Asn
        130                 135                 140

Pro Glu Ile Ala Ala Ala Ile Glu Glu Glu Arg Ala Ser Ala Arg Ser
145                 150                 155                 160

Lys Arg Ser Ser Pro Lys Ser Arg Arg Gly Lys Lys Ser His Glu
                165                 170                 175

Asn Lys Asn Lys Gly Ile Arg Thr His Pro Thr Gln Leu Lys Ala Ser
                180                 185                 190

Glu Leu Asp Ser Thr Phe Ala Asn Met Arg Gly Ser Ala Glu Gly Pro
            195                 200                 205

Lys Glu Glu Asp Glu Arg Pro Leu Ala Ser Ala Pro Glu Gln Pro Ala
210                 215                 220

Pro Leu Pro Glu Val Gly Asn Gln Asp Ala Val Pro Gln Val Ala Ile
225                 230                 235                 240

Pro Leu Pro Ala Cys Glu Pro Gln Pro Glu Val Asp Gly Lys Gln Glu
                245                 250                 255

Val Thr Asp Cys Glu Val Asn Asp Val Glu Glu Glu Leu Glu Glu
                260                 265                 270

Glu Glu Glu Leu Glu Glu Glu Glu Glu Glu Leu Gly Glu Asp Gly
            275                 280                 285

Val Glu Glu Ala Asp Met Pro Asn Glu Ser Ser Ala Lys Glu Pro Glu
        290                 295                 300

Ile Arg Cys Glu Glu Lys Pro Glu Asp Leu Leu Glu Glu Pro Gln Ser
305                 310                 315                 320

Met Ser Asn Glu Ala Arg Glu Asp Ser Pro Asp Val Thr Pro Pro
                325                 330                 335

His Thr Pro Arg Ala Arg Glu Glu Ala Asn Gly Asp Val Leu Glu Thr
            340                 345                 350

Phe Met Phe Pro Cys Gln His Cys Glu Arg Lys Phe Ala Thr Lys Gln
```

-continued

```
            355                 360                 365
Gly Leu Glu Arg His Met His Ile His Ile Ser Thr Ile Asn His Ala
        370                 375                 380
Phe Lys Cys Lys Tyr Cys Gly Lys Arg Phe Gly Thr Gln Ile Asn Arg
385                 390                 395                 400
Arg Arg His Glu Arg Arg His Glu Thr Gly Leu Lys Arg Arg Pro Ser
                405                 410                 415
Met Thr Leu Gln Ser Ser Glu Asp Pro Asp Gly Lys Gly Glu Asn
            420                 425                 430
Val Thr Ser Lys Asp Glu Ser Pro Pro Gln Leu Gly Gln Asp Cys
        435                 440                 445
Leu Ile Leu Asn Ser Glu Lys Thr Ser Gln Glu Val Leu Asn Ser Ser
    450                 455                 460
Phe Val Glu Glu Asn Gly Glu Val Lys Glu Leu His Pro Cys Lys Tyr
465                 470                 475                 480
Cys Lys Lys Val Phe Gly Thr His Thr Asn Met Arg Arg His Gln Arg
                485                 490                 495
Arg Val His Glu Arg His Leu Ile Pro Lys Gly Val Arg Lys Gly
            500                 505                 510
Gly Leu Leu Glu Glu Pro Gln Pro Pro Ala Glu Gln Ala Pro Pro Ser
        515                 520                 525
Gln Asn Val Tyr Val Pro Ser Thr Glu Pro Glu Glu Gly Glu Thr
    530                 535                 540
Asp Asp Val Tyr Ile Met Asp Ile Ser Ser Asn Ile Ser Glu Asn Leu
545                 550                 555                 560
Asn Tyr Tyr Ile Asp Gly Lys Ile Gln Thr Asn Ser Ser Thr Ser Asn
                565                 570                 575
Cys Asp Val Ile Glu Met Glu Ser Asn Ser Ala His Leu Tyr Gly Ile
            580                 585                 590
Asp Cys Leu Leu Thr Pro Val Thr Val Glu Ile Thr Gln Asn Ile Lys
        595                 600                 605
Ser Thr Gln Val Ser Val Thr Asp Asp Leu Leu Lys Asp Ser Pro Ser
    610                 615                 620
Ser Thr Asn Cys Glu Ser Lys Lys Arg Arg Thr Ala Ser Pro Pro Val
625                 630                 635                 640
Leu Pro Lys Ile Lys Thr Glu Thr Glu Ser Asp Ser Thr Ala Pro Ser
                645                 650                 655
Cys Ser Leu Ser Leu Pro Leu Ser Ile Ser Thr Ala Glu Val Val Ser
            660                 665                 670
Phe His Lys Glu Lys Gly Val Tyr Leu Ser Ser Lys Leu Lys Gln Leu
        675                 680                 685
Leu Gln Thr Gln Asp Lys Leu Thr Leu Pro Ala Gly Phe Ser Ala Ala
    690                 695                 700
Glu Ile Pro Lys Leu Gly Pro Val Cys Ala Ser Ala Pro Ala Ser Met
705                 710                 715                 720
Leu Pro Val Thr Ser Ser Arg Phe Lys Arg Arg Thr Ser Ser Pro Pro
                725                 730                 735
Ser Ser Pro Gln His Ser Pro Ala Leu Arg Asp Phe Gly Lys Pro Asn
            740                 745                 750
Asp Gly Lys Ala Ala Trp Thr Asp Thr Val Leu Thr Ser Lys Lys Pro
        755                 760                 765
Lys Leu Glu Ser Arg Ser Asp Ser Pro Ala Trp Ser Leu Ser Gly Arg
    770                 775                 780
```

-continued

```
Asp Glu Arg Glu Thr Gly Ser Pro Pro Cys Phe Asp Glu Tyr Lys Ile
785                 790                 795                 800

Ser Lys Glu Trp Ala Ala Ser Ser Thr Phe Ser Ser Val Cys Asn Gln
            805                 810                 815

Gln Pro Leu Asp Leu Ser Ser Gly Val Lys Gln Lys Ser Glu Gly Thr
            820                 825                 830

Gly Lys Thr Pro Val Pro Trp Glu Ser Val Leu Asp Leu Ser Val His
            835                 840                 845

Lys Lys Pro Cys Asp Ser Glu Gly Lys Glu Phe Lys Glu Asn His Leu
850                 855                 860

Ala Gln Pro Ala Ala Lys Lys Lys Pro Thr Thr Cys Met Leu Gln
865                 870                 875                 880

Lys Val Leu Leu Asn Glu Tyr Asn Gly Val Ser Leu Pro Thr Glu Thr
            885                 890                 895

Thr Pro Glu Val Thr Arg Ser Pro Ser Pro Cys Lys Ser Pro Asp Thr
            900                 905                 910

Gln Pro Asp Pro Glu Leu Gly Pro Asp Ser Ser Cys Ser Val Pro Thr
            915                 920                 925

Ala Glu Ser Pro Pro Glu Val Val Gly Pro Ser Ser Pro Pro Leu Gln
930                 935                 940

Thr Ala Ser Leu Ser Ser Gly Gln Leu Pro Pro Leu Leu Thr Pro Thr
945                 950                 955                 960

Glu Pro Ser Ser Pro Pro Cys Pro Pro Val Leu Thr Val Ala Thr
            965                 970                 975

Pro Pro Pro Pro Leu Leu Pro Thr Val Pro Leu Ser His Pro Ser Ser
            980                 985                 990

Asp Ala Ser Pro Gln Gln Cys Pro Ser Pro Phe Ser Asn Thr Thr Ala
            995                 1000                1005

Gln Ser Pro Leu Pro Ile Leu Ser Pro Thr Val Ser Pro Ser Pro Ser
            1010                1015                1020

Pro Ile Pro Pro Val Glu Pro Leu Met Ser Ala Ala Ser Pro Gly Pro
1025                1030                1035                1040

Pro Thr Leu Ser Ser Ser Ser Ser Ser Ser Ser Phe Pro Ser Ser
            1045                1050                1055

Ser Cys Ser Ser Thr Ser Pro Ser Pro Pro Leu Ser Ala Val Ser
            1060                1065                1070

Ser Val Val Ser Ser Gly Asp Asn Leu Glu Ala Ser Leu Pro Ala Val
            1075                1080                1085

Thr Phe Lys Gln Glu Glu Ser Glu Ser Glu Gly Leu Lys Pro Lys Glu
            1090                1095                1100

Glu Ala Pro Pro Ala Gly Gly Gln Ser Val Val Gln Glu Thr Phe Ser
1105                1110                1115                1120

Lys Asn Phe Ile Cys Asn Val Cys Glu Ser Pro Phe Leu Ser Ile Lys
            1125                1130                1135

Asp Leu Thr Lys His Leu Ser Val His Ala Glu Glu Trp Pro Phe Lys
            1140                1145                1150

Cys Glu Phe Cys Val Gln Leu Phe Lys Val Lys Thr Asp Leu Ser Glu
            1155                1160                1165

His Arg Phe Leu Leu His Gly Val Gly Asn Ile Phe Val Cys Ser Val
            1170                1175                1180

Cys Lys Lys Glu Phe Ala Phe Leu Cys Asn Leu Gln Gln His Gln Arg
1185                1190                1195                1200
```

-continued

```
Asp Leu His Pro Asp Glu Val Cys Thr His His Glu Phe Glu Ser Gly
            1205                1210                1215

Thr Leu Arg Pro Gln Asn Phe Thr Asp Pro Ser Lys Ala Asn Val Glu
            1220                1225                1230

His Met Pro Ser Leu Pro Glu Glu Pro Leu Glu Thr Ser Arg Glu Glu
            1235                1240                1245

Glu Leu Asn Asp Ser Ser Glu Glu Leu Tyr Thr Thr Ile Lys Ile Met
            1250                1255                1260

Ala Ser Gly Ile Lys Thr Lys Asp Pro Asp Val Arg Leu Gly Leu Asn
1265                1270                1275                1280

Gln His Tyr Pro Ser Phe Lys Pro Pro Phe Gln Tyr His His Arg
            1285                1290                1295

Asn Pro Met Gly Ile Gly Val Thr Ala Thr Asn Phe Thr Thr His Asn
            1300                1305                1310

Ile Pro Gln Thr Phe Thr Thr Ala Ile Arg Cys Thr Lys Cys Gly Lys
            1315                1320                1325

Gly Val Asp Asn Met Pro Glu Leu His Lys His Ile Leu Ala Cys Ala
            1330                1335                1340

Ser Ala Ser Asp Lys Lys Arg Tyr Thr Pro Lys Lys Asn Pro Val Pro
1345                1350                1355                1360

Leu Lys Gln Thr Val Gln Pro Lys Asn Gly Val Val Leu Asp Asn
            1365                1370                1375

Ser Gly Lys Asn Ala Phe Arg Arg Met Gly Gln Pro Lys Arg Leu Ser
            1380                1385                1390

Phe Asn Val Glu Leu Gly Lys Met Ser Pro Asn Lys Leu Lys Leu Ser
            1395                1400                1405

Ala Leu Lys Lys Lys Asn Gln Leu Val Gln Lys Ala Ile Leu Gln Lys
            1410                1415                1420

Asn Arg Ala Ala Lys Gln Lys Ala Asp Leu Arg Asp Thr Ser Glu Ala
1425                1430                1435                1440

Ser Ser His Ile Cys Pro Tyr Cys Asp Arg Glu Phe Thr Tyr Ile Gly
            1445                1450                1455

Ser Leu Asn Lys His Ala Ala Phe Ser Cys Pro Lys Lys Pro Leu Ser
            1460                1465                1470

Pro Ser Lys Arg Lys Val Ser His Ser Ser Lys Lys Gly Gly His Ala
            1475                1480                1485

Ser Ser Ser Ser Ser Asp Arg Asn Ser Ser Cys His Pro Arg Arg Arg
            1490                1495                1500

Thr Ala Asp Thr Glu Ile Lys Met Gln Ser Thr Gln Ala Pro Leu Gly
1505                1510                1515                1520

Lys Thr Arg Ala Arg Ser Thr Gly Pro Ala Gln Ala Ser Leu Pro Ser
            1525                1530                1535

Ser Ser Phe Arg Ser Arg Gln Asn Val Lys Phe Ala Ala Ser Val Lys
            1540                1545                1550

Ser Lys Lys Ala Ser Ser Ser Leu Arg Asn Ser Ser Pro Ile Arg
            1555                1560                1565

Met Ala Lys Ile Thr His Val Glu Gly Lys Lys Pro Lys Ala Val Ala
            1570                1575                1580

Lys Ser His Ser Ala Gln Leu Ser Ser Lys Ser Ser Arg Gly Leu His
1585                1590                1595                1600

Val Arg Val Gln Lys Ser Lys Ala Val Ile Gln Ser Lys Thr Ala Leu
            1605                1610                1615

Ala Ser Lys Arg Arg Thr Asp Arg Phe Ile Val Lys Ser Arg Glu Arg
```

```
              1620              1625              1630
Ser Gly Gly Pro Ile Thr Arg Ser Leu Gln Leu Ala Ala Ala Ala Asp
        1635              1640              1645

Leu Ser Glu Ser Arg Arg Glu Asp Ser Ser Ala Arg His Glu Leu Lys
    1650              1655              1660

Asp Phe Ser Tyr Ser Leu Arg Leu Ala Ser Arg Cys Gly Ser Ser Thr
1665              1670              1675              1680

Ala Ser Tyr Ile Thr Arg Gln Cys Arg Lys Val Lys Ala Ala Ala Ala
            1685              1690              1695

Thr Pro Phe Gln Gly Pro Phe Leu Lys Glu
        1700              1705

(2) INFORMATION FOR SEQ ID NO:3:

(i) SEQUENCE CHARACTERISTICS:
        (A) LENGTH: 5868 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 121..5278

(xi) SEQUENCE DESCRIPTION: SEQ ID NO:3:

GGAAAATTTA TTCCCACTGG AAATCAACAG AGCCATTTAC TATAAAACTT TAAAGGGTTC        60

ATGTAATCAA AGAAGTTTCT TGTGTGTGTG TATCTTTACA GAACACAACA GGAATTGAAA       120

ATG AAT CAG AAC ACT ACT GAG CCT GTG GCG GCC ACC GAG ACC CTG GCT        168
Met Asn Gln Asn Thr Thr Glu Pro Val Ala Ala Thr Glu Thr Leu Ala
  1               5                  10                  15

GAG GTA CCC GAA CAT GTG CTG CGA GGA CTT CCG GAG GAA GTG AGG CTT        216
Glu Val Pro Glu His Val Leu Arg Gly Leu Pro Glu Glu Val Arg Leu
                20                  25                  30

TTC CCT TCT GCT GTT GAC AAG ACC CGG ATT GGT GTC TGG GCC ACT AAA        264
Phe Pro Ser Ala Val Asp Lys Thr Arg Ile Gly Val Trp Ala Thr Lys
            35                  40                  45

CCA ATT TTA AAA GGG AAA AAA TTT GGG CCA TTT GTT GGT GAT AAG AAA        312
Pro Ile Leu Lys Gly Lys Lys Phe Gly Pro Phe Val Gly Asp Lys Lys
     50                  55                  60

AAA AGA TCT CAG GTT AAG AAT AAT GTA TAC ATG TGG GAG GTG TAT TAC        360
Lys Arg Ser Gln Val Lys Asn Asn Val Tyr Met Trp Glu Val Tyr Tyr
 65                  70                  75                  80

CCA AAT TTG GGA TGG ATG TGC ATT GAT GCC ACT GAT CCA GAG AAG GGA        408
Pro Asn Leu Gly Trp Met Cys Ile Asp Ala Thr Asp Pro Glu Lys Gly
                 85                  90                  95

AAC TGG CTG CGA TAT GTG AAT TGG GCT TGC TCA GGA GAA GAG CAA AAT        456
Asn Trp Leu Arg Tyr Val Asn Trp Ala Cys Ser Gly Glu Glu Gln Asn
            100                 105                 110

TTA TTC CCA CTG GAA ATC AAC AGA GCC ATT TAC TAT AAA ACT TTA AAG        504
Leu Phe Pro Leu Glu Ile Asn Arg Ala Ile Tyr Tyr Lys Thr Leu Lys
        115                 120                 125

CCA ATC GCG CCG GGC GAG GAG CTC CTG GTC TGG TAC AAT GGG GAA GAC        552
Pro Ile Ala Pro Gly Glu Glu Leu Leu Val Trp Tyr Asn Gly Glu Asp
    130                 135                 140

AAC CCT GAG ATA GCA GCT GCG ATT GAG GAA GAG CGA GCC AGC GCC CGG        600
Asn Pro Glu Ile Ala Ala Ala Ile Glu Glu Glu Arg Ala Ser Ala Arg
145                 150                 155                 160

AGC AAG CGG AGC TCC CCC AAG AGC CGG AAA GGG AAG AAA AAA TCC CAG        648
Ser Lys Arg Ser Ser Pro Lys Ser Arg Lys Gly Lys Lys Lys Ser Gln
                165                 170                 175
```

-continued

```
GAA AAT AAA AAC AAA GGA AAC AAA ATC CAA GAC ATA CAA CTG AAG ACA        696
Glu Asn Lys Asn Lys Gly Asn Lys Ile Gln Asp Ile Gln Leu Lys Thr
            180                 185                 190

AGT GAG CCA GAT TTC ACC TCT GCA AAT ATG AGA GAT TCT GCA GAA GGT        744
Ser Glu Pro Asp Phe Thr Ser Ala Asn Met Arg Asp Ser Ala Glu Gly
        195                 200                 205

CCT AAA GAA GAC GAA GAG AAG CCT TCA GCC TCA GCA CTT GAG CAG CCG        792
Pro Lys Glu Asp Glu Glu Lys Pro Ser Ala Ser Ala Leu Glu Gln Pro
    210                 215                 220

GCC ACC CTC CAG GAG GTG GCC AGT CAG GAG GTG CCT CCA GAA CTA GCA        840
Ala Thr Leu Gln Glu Val Ala Ser Gln Glu Val Pro Pro Glu Leu Ala
225                 230                 235                 240

ACC CCT GCC CCT GCC TGG GAG CCA CAG CCA GAA CCA GAC GAG CGA TTA        888
Thr Pro Ala Pro Ala Trp Glu Pro Gln Pro Glu Pro Asp Glu Arg Leu
                    245                 250                 255

GAA GCG GCA GCT TGT GAG GTG AAT GAT TTG GGG GAA GAG GAG GAG GAG        936
Glu Ala Ala Ala Cys Glu Val Asn Asp Leu Gly Glu Glu Glu Glu Glu
                260                 265                 270

GAA GAG GAG GAG GAT GAA GAA GAA GAA GAT GAT GAT GAT GAT GAG            984
Glu Glu Glu Glu Asp Glu Glu Glu Glu Asp Asp Asp Asp Asp Glu
            275                 280                 285

TTG GAA GAC GAG GGG GAA GAA GAA GCC AGC ATG CCA AAT GAA AAT TCT       1032
Leu Glu Asp Glu Gly Glu Glu Glu Ala Ser Met Pro Asn Glu Asn Ser
        290                 295                 300

GTG AAA GAG CCA GAA ATA CGG TGT GAT GAG AAG CCA GAA GAT TTA TTA       1080
Val Lys Glu Pro Glu Ile Arg Cys Asp Glu Lys Pro Glu Asp Leu Leu
305                 310                 315                 320

GAG GAA CCA AAA ACA ACT TCA GAA GAA ACT CTT GAA GAC TGC TCA GAG       1128
Glu Glu Pro Lys Thr Thr Ser Glu Glu Thr Leu Glu Asp Cys Ser Glu
                325                 330                 335

GTA ACA CCT GCC ATG CAA ATC CCC AGA ACT AAA GAA GAG GCC AAT GGT       1176
Val Thr Pro Ala Met Gln Ile Pro Arg Thr Lys Glu Glu Ala Asn Gly
                340                 345                 350

GAT GTA TTT GAA ACG TTT ATG TTT CCG TGT CAA CAT TGT GAA AGG AAG       1224
Asp Val Phe Glu Thr Phe Met Phe Pro Cys Gln His Cys Glu Arg Lys
            355                 360                 365

TTT ACA ACC AAA CAG GGG CTT GAG CGT CAC ATG CAT ATC CAT ATA TCC       1272
Phe Thr Thr Lys Gln Gly Leu Glu Arg His Met His Ile His Ile Ser
        370                 375                 380

ACC GTC AAT CAT GCT TTC AAA TGC AAG TAC TGT GGG AAA GCC TTT GGC       1320
Thr Val Asn His Ala Phe Lys Cys Lys Tyr Cys Gly Lys Ala Phe Gly
385                 390                 395                 400

ACA CAG ATT AAC CGG CGG CGA CAT GAG CGG CGC CAT GAA GCA GGG TTA       1368
Thr Gln Ile Asn Arg Arg Arg His Glu Arg Arg His Glu Ala Gly Leu
                405                 410                 415

AAG CGG AAA CCC AGC CAA ACA CTA CAG CCG TCA GAG GAT CTG GCT GAT       1416
Lys Arg Lys Pro Ser Gln Thr Leu Gln Pro Ser Glu Asp Leu Ala Asp
                420                 425                 430

GGC AAA GCA TCT GGA GAA AAC GTT GCT TCA AAA GAT GAT TCG AGT CCT       1464
Gly Lys Ala Ser Gly Glu Asn Val Ala Ser Lys Asp Asp Ser Ser Pro
            435                 440                 445

CCC AGT CTT GGG CCA GAC TGT CTG ATC ATG AAT TCA GAG AAG GCT TCC       1512
Pro Ser Leu Gly Pro Asp Cys Leu Ile Met Asn Ser Glu Lys Ala Ser
        450                 455                 460

CAA GAC ACA ATA AAT TCT TCT GTC GTA GAA GAG AAT GGG GAA GTT AAA       1560
Gln Asp Thr Ile Asn Ser Ser Val Val Glu Glu Asn Gly Glu Val Lys
465                 470                 475                 480

GAA CTT CAT CCG TGC AAA TAT TGT AAA AAG GTT TTT GGA ACT CAT ACT       1608
Glu Leu His Pro Cys Lys Tyr Cys Lys Lys Val Phe Gly Thr His Thr
```

```
                485                 490                 495
AAT ATG AGA CGG CAT CAG CGT AGA GTT CAC GAA CGT CAT CTG ATT CCC    1656
Asn Met Arg Arg His Gln Arg Arg Val His Glu Arg His Leu Ile Pro
            500                 505                 510

AAA GGT GTA CGG CGA AAA GGA GGC CTT GAA GAG CCC CAG CCT CCA GCA    1704
Lys Gly Val Arg Arg Lys Gly Gly Leu Glu Glu Pro Gln Pro Pro Ala
            515                 520                 525

GAA CAG GCC CAG GCC ACC CAG AAC GTG TAT GTA CCA AGC ACA GAG CCG    1752
Glu Gln Ala Gln Ala Thr Gln Asn Val Tyr Val Pro Ser Thr Glu Pro
    530                 535                 540

GAG GAG GAA GGG GAA GCA GAT GAT GTG TAC ATC ATG GAC ATT TCT AGC    1800
Glu Glu Glu Gly Glu Ala Asp Asp Val Tyr Ile Met Asp Ile Ser Ser
545                 550                 555                 560

AAT ATC TCT GAA AAC TTA AAT TAC TAT ATT GAT GGT AAA ATT CAA ACT    1848
Asn Ile Ser Glu Asn Leu Asn Tyr Tyr Ile Asp Gly Lys Ile Gln Thr
            565                 570                 575

AAT AAC AAC ACT AGT AAC TGT GAT GTG ATT GAG ATG GAG TCT GCT TCG    1896
Asn Asn Asn Thr Ser Asn Cys Asp Val Ile Glu Met Glu Ser Ala Ser
            580                 585                 590

GCA GAT TTG TAT GGT ATA AAT TGT CTG CTC ACT CCA GTT ACA GTG GAA    1944
Ala Asp Leu Tyr Gly Ile Asn Cys Leu Leu Thr Pro Val Thr Val Glu
            595                 600                 605

ATT ACT CAA AAT ATA AAG ACC ACA CAG GTC CCT GTA ACA GAA GAT CTT    1992
Ile Thr Gln Asn Ile Lys Thr Thr Gln Val Pro Val Thr Glu Asp Leu
    610                 615                 620

CCT AAA GAG CCT TTG GGC AGC ACA AAT AGT GAG GCC AAG AAG CGG AGA    2040
Pro Lys Glu Pro Leu Gly Ser Thr Asn Ser Glu Ala Lys Lys Arg Arg
625                 630                 635                 640

ACT GCG AGC CCA CCT GCA CTG CCC AAA ATT AAG GCC GAA ACA GAC TCT    2088
Thr Ala Ser Pro Pro Ala Leu Pro Lys Ile Lys Ala Glu Thr Asp Ser
            645                 650                 655

GAC CCC ATG GTC CCC TCT TGC TCT TTA AGT CTT CCT CTT AGC ATA TCA    2136
Asp Pro Met Val Pro Ser Cys Ser Leu Ser Leu Pro Leu Ser Ile Ser
            660                 665                 670

ACA ACA GAG GCA GTG TCT TTC CAC AAA GAG AAA AGT GTT TAT TTG TCA    2184
Thr Thr Glu Ala Val Ser Phe His Lys Glu Lys Ser Val Tyr Leu Ser
            675                 680                 685

TCA AAG CTC AAA CAA CTT CTT CAA ACC CAA GAT AAA CTA ACT CCT CCT    2232
Ser Lys Leu Lys Gln Leu Leu Gln Thr Gln Asp Lys Leu Thr Pro Pro
    690                 695                 700

GCA GGG ATT TCA GCA ACT GAA ATA GCT AAA TTA GGT CCT GTT TGT GTG    2280
Ala Gly Ile Ser Ala Thr Glu Ile Ala Lys Leu Gly Pro Val Cys Val
705                 710                 715                 720

TCT GCT CCT GCA TCA ATG TTG CCT GTG ACC TCA AGT AGG TTT AAG AGG    2328
Ser Ala Pro Ala Ser Met Leu Pro Val Thr Ser Ser Arg Phe Lys Arg
            725                 730                 735

CGG ACC AGC TCT CCT CCC AGT TCT CCA CAG CAC AGT CCT GCC CTT CGA    2376
Arg Thr Ser Ser Pro Pro Ser Ser Pro Gln His Ser Pro Ala Leu Arg
            740                 745                 750

GAC TTT GGA AAG CCA AGT GAT GGG AAA GCA GCA TGG ACC GAT GCC GGG    2424
Asp Phe Gly Lys Pro Ser Asp Gly Lys Ala Ala Trp Thr Asp Ala Gly
            755                 760                 765

CTG ACT TCC AAA AAA TCC AAA TTA GAA AGT CAC AGC GAC TCA CCA GCA    2472
Leu Thr Ser Lys Lys Ser Lys Leu Glu Ser His Ser Asp Ser Pro Ala
            770                 775                 780

TGG AGT TTG TCT GGG AGA GAT GAG AGA GAA ACT GTG AGC CCT CCA TGC    2520
Trp Ser Leu Ser Gly Arg Asp Glu Arg Glu Thr Val Ser Pro Pro Cys
785                 790                 795                 800

TTT GAT GAA TAT AAA ATG TCT AAA GAG TGG ACA GCT AGT CTG GCT TTT    2568
```

-continued

```
          Phe Asp Glu Tyr Lys Met Ser Lys Glu Trp Thr Ala Ser Ser Ala Phe
                          805                 810                 815

AGC AGT GTG TGC AAC CAG CAG CCA CTG GAT TTA TCC AGC GGT GTC AAA            2616
Ser Ser Val Cys Asn Gln Gln Pro Leu Asp Leu Ser Ser Gly Val Lys
            820                 825                 830

CAG AAG GCT GAG GGT ACA GGC AAG ACT CCA GTC CAG TGG GAA TCT GTC            2664
Gln Lys Ala Glu Gly Thr Gly Lys Thr Pro Val Gln Trp Glu Ser Val
835                 840                 845

TTA GAT CTC AGT GTG CAT AAA AAG CAT TGT AGT GAC TCT GAA GGC AAG            2712
Leu Asp Leu Ser Val His Lys Lys His Cys Ser Asp Ser Glu Gly Lys
    850                 855                 860

GAA TTC AAA GAA AGT CAT TCA GTG CAG CCT ACG TGT AGT GCT GTA AAG            2760
Glu Phe Lys Glu Ser His Ser Val Gln Pro Thr Cys Ser Ala Val Lys
865                 870                 875                 880

AAA AGG AAA CCA ACC ACC TGC ATG CTG CAG AAG GTT CTT CTC AAT GAA            2808
Lys Arg Lys Pro Thr Thr Cys Met Leu Gln Lys Val Leu Leu Asn Glu
                885                 890                 895

TAT AAT GGC ATC GAT TTA CCT GTA GAA AAC CCT GCA GAT GGG ACC AGG            2856
Tyr Asn Gly Ile Asp Leu Pro Val Glu Asn Pro Ala Asp Gly Thr Arg
                900                 905                 910

AGC CCA AGT CCT TGT AAA TCC CTA GAA GCT CAG CCA GAT CCT GAC CTC            2904
Ser Pro Ser Pro Cys Lys Ser Leu Glu Ala Gln Pro Asp Pro Asp Leu
            915                 920                 925

GGT CCG GGC TCT GGT TTC CCT GCC CCT ACT GTT GAG TCC ACA CCT GAT            2952
Gly Pro Gly Ser Gly Phe Pro Ala Pro Thr Val Glu Ser Thr Pro Asp
930                 935                 940

GTT TGT CCT TCA TCA CCT GCC CTG CAG ACA CCC TCC CTT TCA TCC GGT            3000
Val Cys Pro Ser Ser Pro Ala Leu Gln Thr Pro Ser Leu Ser Ser Gly
945                 950                 955                 960

CAG CTG CCT CCT CTC TTG ATC CCC ACA GAT CCC TCT TCC CCT CCA CCC            3048
Gln Leu Pro Pro Leu Leu Ile Pro Thr Asp Pro Ser Ser Pro Pro Pro
                965                 970                 975

TGT CCC CCG GTA TTA ACT GTT GCC ACT CCG CCC CCT CCC CTC CTT CCT            3096
Cys Pro Pro Val Leu Thr Val Ala Thr Pro Pro Pro Pro Leu Leu Pro
                980                 985                 990

ACC GTA CCT CTT CCA GCC CCC TCT TCC AGT GCA TCT CCA CAC CCA TGC            3144
Thr Val Pro Leu Pro Ala Pro Ser Ser Ser Ala Ser Pro His Pro Cys
            995                 1000                1005

CCC TCT CCA CTC TCA AAT GCC ACC GCA CAG TCC CCA CTT CCA ATT CTG            3192
Pro Ser Pro Leu Ser Asn Ala Thr Ala Gln Ser Pro Leu Pro Ile Leu
    1010                1015                1020

TCC CCA ACA GTG TCC CCC TCT CCC TCT CCC ATT CCT CCC GTG GAG CCC            3240
Ser Pro Thr Val Ser Pro Ser Pro Ser Pro Ile Pro Pro Val Glu Pro
1025                1030                1035                1040

CTG ATG TCT GCC GCC TCA CCC GGG CCT CCA ACA CTT TCT TCT TCC TCC            3288
Leu Met Ser Ala Ala Ser Pro Gly Pro Pro Thr Leu Ser Ser Ser Ser
                1045                1050                1055

TCT TCA TCT TCC TCC TCC TCT TCG TTT TCT TCT TCA TCT TCC TCC TCT            3336
Ser Ser Ser Ser Ser Ser Ser Phe Ser Ser Ser Ser Ser Ser Ser Ser
                1060                1065                1070

TCT CCT TCT CCA CCT CCT CTC TCC GCA ATA TCA TCT GTT GTT TCC TCT            3384
Ser Pro Ser Pro Pro Pro Leu Ser Ala Ile Ser Ser Val Val Ser Ser
                1075                1080                1085

GGT GAT AAT CTG GAG GCT TCT CTC CCC ATG ATA TCT TTC AAA CAG GAG            3432
Gly Asp Asn Leu Glu Ala Ser Leu Pro Met Ile Ser Phe Lys Gln Glu
                1090                1095                1100

GAA TTA GAG AAT GAA GGT CTG AAA CCC AGG GAA GAG CCC CAG TCT GCT            3480
Glu Leu Glu Asn Glu Gly Leu Lys Pro Arg Glu Glu Pro Gln Ser Ala
1105                1110                1115                1120
```

```
GCT GAA CAG GAT GTT GTT GTT CAG GAA ACA TTC AAC AAA AAC TTT GTT      3528
Ala Glu Gln Asp Val Val Val Gln Glu Thr Phe Asn Lys Asn Phe Val
            1125                1130                1135

TGC AAC GTC TGT GAA TCA CCT TTT CTT TCC ATT AAA GAT CTA ACC AAA      3576
Cys Asn Val Cys Glu Ser Pro Phe Leu Ser Ile Lys Asp Leu Thr Lys
            1140                1145                1150

CAT TTA TCT ATT CAT GCT GAA GAA TGG CCC TTC AAA TGT GAA TTT TGT      3624
His Leu Ser Ile His Ala Glu Glu Trp Pro Phe Lys Cys Glu Phe Cys
            1155                1160                1165

GTG CAG CTT TTT AAG GAT AAA ACG GAC TTG TCA GAA CAT CGC TTT TTG      3672
Val Gln Leu Phe Lys Asp Lys Thr Asp Leu Ser Glu His Arg Phe Leu
            1170                1175                1180

CTT CAT GGA GTT GGG AAT ATC TTT GTG TGT TCT GTT TGT AAA AAA GAA      3720
Leu His Gly Val Gly Asn Ile Phe Val Cys Ser Val Cys Lys Lys Glu
1185                1190                1195                1200

TTT GCT TTT TTG TGC AAT TTG CAG CAG CAC CAG CGA GAT CTC CAC CCA      3768
Phe Ala Phe Leu Cys Asn Leu Gln Gln His Gln Arg Asp Leu His Pro
                1205                1210                1215

GAT AAG GTG TGC ACA CAT CAC GAG TTT GAA AGC GGG ACT CTG AGG CCC      3816
Asp Lys Val Cys Thr His His Glu Phe Glu Ser Gly Thr Leu Arg Pro
            1220                1225                1230

CAG AAC TTT ACA GAT CCC AGC AAG GCC CAT GTA GAG CAT ATG CAG AGC      3864
Gln Asn Phe Thr Asp Pro Ser Lys Ala His Val Glu His Met Gln Ser
            1235                1240                1245

TTG CCA GAA GAT CCT TTA GAA ACT TCT AAA GAA GAA GAG GAG TTA AAT      3912
Leu Pro Glu Asp Pro Leu Glu Thr Ser Lys Glu Glu Glu Glu Leu Asn
            1250                1255                1260

GAT TCC TCT GAA GAG CTT TAC ACG ACT ATA AAA ATA ATG GCT TCT GGA      3960
Asp Ser Ser Glu Glu Leu Tyr Thr Thr Ile Lys Ile Met Ala Ser Gly
1265                1270                1275                1280

ATA AAG ACA AAA GAT CCA GAT GTT CGA TTG GGC CTC AAT CAG CAT TAC      4008
Ile Lys Thr Lys Asp Pro Asp Val Arg Leu Gly Leu Asn Gln His Tyr
                1285                1290                1295

CCA AGC TTT AAA CCA CCT CCA TTT CAG TAC CAT CAC CGT AAC CCC ATG      4056
Pro Ser Phe Lys Pro Pro Pro Phe Gln Tyr His His Arg Asn Pro Met
            1300                1305                1310

GGG ATT GGT GTG ACA GCC ACA AAT TTC ACT ACA CAC AAT ATT CCA CAG      4104
Gly Ile Gly Val Thr Ala Thr Asn Phe Thr Thr His Asn Ile Pro Gln
            1315                1320                1325

ACT TTC ACT ACC GCC ATT CGC TGC ACA AAG TGT GGA AAA GGT GTC GAC      4152
Thr Phe Thr Thr Ala Ile Arg Cys Thr Lys Cys Gly Lys Gly Val Asp
            1330                1335                1340

AAT ATG CCG GAG TTG CAC AAA CAT ATC CTG GCT TGT GCT TCT GCA AGT      4200
Asn Met Pro Glu Leu His Lys His Ile Leu Ala Cys Ala Ser Ala Ser
1345                1350                1355                1360

GAC AAG AAG AGG TAC ACG CCT AAG AAA AAC CCA GTA CCA TTA AAA CAA      4248
Asp Lys Lys Arg Tyr Thr Pro Lys Lys Asn Pro Val Pro Leu Lys Gln
                1365                1370                1375

ACT GTG CAA CCC AAA AAT GGC GTG GTG GTT TTA GAT AAC TCT GGG AAA      4296
Thr Val Gln Pro Lys Asn Gly Val Val Val Leu Asp Asn Ser Gly Lys
            1380                1385                1390

AAT GCC TTC CGA CGA ATG GGA CAG CCC AAA AGG CTT AAC TTT AGT GTT      4344
Asn Ala Phe Arg Arg Met Gly Gln Pro Lys Arg Leu Asn Phe Ser Val
            1395                1400                1405

GAG CTC AGC AAA ATG TCG TCG AAT AAG CTC AAA TTA AAT GCA TTG AAG      4392
Glu Leu Ser Lys Met Ser Ser Asn Lys Leu Lys Leu Asn Ala Leu Lys
            1410                1415                1420

AAA AAA AAT CAG CTA GTA CAG AAA GCA ATT CTT CAG AAA AAC AAA TCT      4440
Lys Lys Asn Gln Leu Val Gln Lys Ala Ile Leu Gln Lys Asn Lys Ser
1425                1430                1435                1440
```

```
GCA AAG CAG AAG GCC GAC TTG AAA AAT GCT TGT GAG TCA TCC TCT CAC          4488
Ala Lys Gln Lys Ala Asp Leu Lys Asn Ala Cys Glu Ser Ser Ser His
                1445                1450                1455

ATC TGC CCT TAC TGT AAT CGA GAG TTC ACT TAC ATT GGA AGC CTG AAT          4536
Ile Cys Pro Tyr Cys Asn Arg Glu Phe Thr Tyr Ile Gly Ser Leu Asn
                1460                1465                1470

AAA CAC GCC GCC TTC AGC TGT CCC AAA AAA CCC CTT TCT CCT CCC AAA          4584
Lys His Ala Ala Phe Ser Cys Pro Lys Lys Pro Leu Ser Pro Pro Lys
                1475                1480                1485

AAA AAA GTT TCT CAT TCA TCT AAG AAA GGT GGA CAC TCA TCA CCT GCA          4632
Lys Lys Val Ser His Ser Ser Lys Lys Gly Gly His Ser Ser Pro Ala
                1490                1495                1500

AGT AGT GAC AAA AAC AGT AAC AGC AAC CAC CGC AGA CGG ACA GCG GAT          4680
Ser Ser Asp Lys Asn Ser Asn Ser Asn His Arg Arg Arg Thr Ala Asp
1505                1510                1515                1520

GCG GAG ATT AAA ATG CAA AGC ATG CAG ACT CCG TTG GGC AAG ACC AGA          4728
Ala Glu Ile Lys Met Gln Ser Met Gln Thr Pro Leu Gly Lys Thr Arg
                1525                1530                1535

GCC CGC AGC TCA GGC CCC ACC CAA GTC CCA CTT CCC TCC TCA TCC TTC          4776
Ala Arg Ser Ser Gly Pro Thr Gln Val Pro Leu Pro Ser Ser Ser Phe
                1540                1545                1550

AGG TCC AAG CAG AAC GTC AAG TTT GCA GCT TCG GTG AAA TCC AAA AAA          4824
Arg Ser Lys Gln Asn Val Lys Phe Ala Ala Ser Val Lys Ser Lys Lys
                1555                1560                1565

CCA AGC TCC TCC TCT TTA AGG AAC TCC AGC CCG ATA AGA ATG GCC AAA          4872
Pro Ser Ser Ser Ser Leu Arg Asn Ser Ser Pro Ile Arg Met Ala Lys
                1570                1575                1580

ATA ACT CAT GTT GAG GGG AAA AAA CCT AAA GCT GTG GCC AAG AAT CAT          4920
Ile Thr His Val Glu Gly Lys Lys Pro Lys Ala Val Ala Lys Asn His
1585                1590                1595                1600

TCT GCT CAG CTT TCC AGC AAA ACA TCG CGG AGC CTG CAC GTG AGG GTA          4968
Ser Ala Gln Leu Ser Ser Lys Thr Ser Arg Ser Leu His Val Arg Val
                1605                1610                1615

CAG AAA AGC AAA GCT GTT TTA CAA AGC AAA TCC ACC TTG GCG AGT AAG          5016
Gln Lys Ser Lys Ala Val Leu Gln Ser Lys Ser Thr Leu Ala Ser Lys
                1620                1625                1630

AAA AGA ACA GAC CGG TTC AAT ATA AAA TCT AGA GAG CGG AGT GGG GGG          5064
Lys Arg Thr Asp Arg Phe Asn Ile Lys Ser Arg Glu Arg Ser Gly Gly
                1635                1640                1645

CCA GTC ACC CGG AGC CTT CAG CTG GCA GCT GCT GCT GAC TTG AGT GAG          5112
Pro Val Thr Arg Ser Leu Gln Leu Ala Ala Ala Ala Asp Leu Ser Glu
                1650                1655                1660

AAC AAG AGA GAG GAC GGC AGC GCC AAG CAG GAG CTG AAG GAC TTC AGC          5160
Asn Lys Arg Glu Asp Gly Ser Ala Lys Gln Glu Leu Lys Asp Phe Ser
1665                1670                1675                1680

TAC AGC CTC CGC TTG GCG TCC CGA TGC TCT CCA CCA GCC GCC TCT TAC          5208
Tyr Ser Leu Arg Leu Ala Ser Arg Cys Ser Pro Pro Ala Ala Ser Tyr
                1685                1690                1695

ATC ACC AGG CAG TAT AGG AAG GTC AAA GCT CCG GCT GCA GCC CAG TTC          5256
Ile Thr Arg Gln Tyr Arg Lys Val Lys Ala Pro Ala Ala Ala Gln Phe
                1700                1705                1710

CAG GGA CCA TTC TTC AAA GAG T AGACACTCTG GCTGCTCCCT GACAGCACCT          5308
Gln Gly Pro Phe Phe Lys Glu
                1715

GAAGTGACCT GGAATCAGTG AAGCCAAAGG GACTGGCAGT CTGCCTGCAG GGAGTACCGA          5368

CCTATCCCAG TTGTGTGAGG CTGCGAGAGA AAGGGAGTGC ATGTGCGCGC GTGCATGTGT          5428

GCGTGCGTGT GTGTTCACGT GTTCTCGTGC GGGCCGTGAG TGGTCTTCAA ACGAGGGTCC          5488
```

```
CGAACCCCGG GGCGGCAGGA AGGGGGCCGA CTCCACGCTG TCCTTTGGGA TGATACTTGG     5548

ATGTCAGCTC TTGGGACCGT GTCTGCAGCC CAGCCTTCCT GTTGGGGTGG GGCCTCTCCT     5608

ACTATGCAAT TTTTCAAGAG CTCCTTGACC CTGCTTTTTG CTTCTTGAGT TGTCTTTTGC     5668

CATTATGGGG ACTTTGGTTT GACCCAGGGG TCAGCCCTTT AGGAAGGCCT TCAGGAGGAG     5728

GCCGAGTTCC CCTTCAGTAC CACCCCTCTC TCCCCACCTG CCCGCTCCCG GCAACATCTC     5788

TGGGAATCAA CAGCATATTG ACACGTTGGA GCCGAGCCTG AACATGCCCT GACCCCAGCA     5848

CATGGAAAAC CCCCTTCCTT                                                5868
```

(2) INFORMATION FOR SEQ ID NO:4:

(i) SEQUENCE CHARACTERISTICS:
        (A) LENGTH: 1719 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asn Gln Asn Thr Thr Glu Pro Val Ala Ala Thr Glu Thr Leu Ala
  1               5                  10                  15

Glu Val Pro Glu His Val Leu Arg Gly Leu Pro Glu Glu Val Arg Leu
                 20                  25                  30

Phe Pro Ser Ala Val Asp Lys Thr Arg Ile Gly Val Trp Ala Thr Lys
             35                  40                  45

Pro Ile Leu Lys Gly Lys Lys Phe Gly Pro Phe Val Gly Asp Lys Lys
         50                  55                  60

Lys Arg Ser Gln Val Lys Asn Asn Val Tyr Met Trp Glu Val Tyr Tyr
 65                  70                  75                  80

Pro Asn Leu Gly Trp Met Cys Ile Asp Ala Thr Asp Pro Glu Lys Gly
                 85                  90                  95

Asn Trp Leu Arg Tyr Val Asn Trp Ala Cys Ser Gly Glu Glu Gln Asn
                100                 105                 110

Leu Phe Pro Leu Glu Ile Asn Arg Ala Ile Tyr Tyr Lys Thr Leu Lys
            115                 120                 125

Pro Ile Ala Pro Gly Glu Glu Leu Leu Val Trp Tyr Asn Gly Glu Asp
        130                 135                 140

Asn Pro Glu Ile Ala Ala Ala Ile Glu Glu Arg Ala Ser Ala Arg
145                 150                 155                 160

Ser Lys Arg Ser Ser Pro Lys Ser Arg Lys Gly Lys Lys Ser Gln
                165                 170                 175

Glu Asn Lys Asn Lys Gly Asn Lys Ile Gln Asp Ile Gln Leu Lys Thr
                180                 185                 190

Ser Glu Pro Asp Phe Thr Ser Ala Asn Met Arg Asp Ser Ala Glu Gly
            195                 200                 205

Pro Lys Glu Asp Glu Glu Lys Pro Ser Ala Ser Ala Leu Glu Gln Pro
        210                 215                 220

Ala Thr Leu Gln Glu Val Ala Ser Gln Glu Val Pro Pro Glu Leu Ala
225                 230                 235                 240

Thr Pro Ala Pro Ala Trp Glu Pro Gln Pro Glu Pro Asp Glu Arg Leu
                245                 250                 255

Glu Ala Ala Ala Cys Glu Val Asn Asp Leu Gly Glu Glu Glu Glu
                260                 265                 270

Glu Glu Glu Glu Asp Glu Glu Glu Glu Asp Asp Asp Asp Glu
            275                 280                 285
```

```
Leu Glu Asp Glu Gly Glu Glu Ala Ser Met Pro Asn Glu Asn Ser
    290                 295                 300
Val Lys Glu Pro Glu Ile Arg Cys Asp Glu Lys Pro Glu Asp Leu Leu
305                 310                 315                 320
Glu Glu Pro Lys Thr Thr Ser Glu Glu Thr Leu Glu Asp Cys Ser Glu
                325                 330                 335
Val Thr Pro Ala Met Gln Ile Pro Arg Thr Lys Glu Glu Ala Asn Gly
                340                 345                 350
Asp Val Phe Glu Thr Phe Met Phe Pro Cys Gln His Cys Glu Arg Lys
            355                 360                 365
Phe Thr Thr Lys Gln Gly Leu Glu Arg His Met His Ile His Ile Ser
    370                 375                 380
Thr Val Asn His Ala Phe Lys Cys Lys Tyr Cys Gly Lys Ala Phe Gly
385                 390                 395                 400
Thr Gln Ile Asn Arg Arg Arg His Glu Arg Arg His Glu Ala Gly Leu
                405                 410                 415
Lys Arg Lys Pro Ser Gln Thr Leu Gln Pro Ser Glu Asp Leu Ala Asp
                420                 425                 430
Gly Lys Ala Ser Gly Glu Asn Val Ala Ser Lys Asp Asp Ser Ser Pro
            435                 440                 445
Pro Ser Leu Gly Pro Asp Cys Leu Ile Met Asn Ser Glu Lys Ala Ser
    450                 455                 460
Gln Asp Thr Ile Asn Ser Ser Val Val Glu Glu Asn Gly Glu Val Lys
465                 470                 475                 480
Glu Leu His Pro Cys Lys Tyr Cys Lys Lys Val Phe Gly Thr His Thr
                485                 490                 495
Asn Met Arg Arg His Gln Arg Arg Val His Glu Arg His Leu Ile Pro
                500                 505                 510
Lys Gly Val Arg Arg Lys Gly Leu Glu Glu Pro Gln Pro Ala
            515                 520                 525
Glu Gln Ala Gln Ala Thr Gln Asn Val Tyr Val Pro Ser Thr Glu Pro
    530                 535                 540
Glu Glu Glu Gly Glu Ala Asp Asp Val Tyr Ile Met Asp Ile Ser Ser
545                 550                 555                 560
Asn Ile Ser Glu Asn Leu Asn Tyr Tyr Ile Asp Gly Lys Ile Gln Thr
                565                 570                 575
Asn Asn Asn Thr Ser Asn Cys Asp Val Ile Glu Met Glu Ser Ala Ser
            580                 585                 590
Ala Asp Leu Tyr Gly Ile Asn Cys Leu Leu Thr Pro Val Thr Val Glu
    595                 600                 605
Ile Thr Gln Asn Ile Lys Thr Thr Gln Val Pro Val Thr Glu Asp Leu
610                 615                 620
Pro Lys Glu Pro Leu Gly Ser Thr Asn Ser Glu Ala Lys Lys Arg Arg
625                 630                 635                 640
Thr Ala Ser Pro Pro Ala Leu Pro Lys Ile Lys Ala Glu Thr Asp Ser
                645                 650                 655
Asp Pro Met Val Pro Ser Cys Ser Leu Ser Leu Pro Leu Ser Ile Ser
                660                 665                 670
Thr Thr Glu Ala Val Ser Phe His Lys Glu Lys Ser Val Tyr Leu Ser
            675                 680                 685
Ser Lys Leu Lys Gln Leu Leu Gln Thr Gln Asp Lys Leu Thr Pro Pro
    690                 695                 700
```

-continued

```
Ala Gly Ile Ser Ala Thr Glu Ile Ala Lys Leu Gly Pro Val Cys Val
705                 710                 715                 720

Ser Ala Pro Ala Ser Met Leu Pro Val Thr Ser Ser Arg Phe Lys Arg
            725                 730                 735

Arg Thr Ser Ser Pro Pro Ser Ser Pro Gln His Ser Pro Ala Leu Arg
            740                 745                 750

Asp Phe Gly Lys Pro Ser Asp Gly Lys Ala Ala Trp Thr Asp Ala Gly
            755                 760                 765

Leu Thr Ser Lys Lys Ser Lys Leu Glu Ser His Ser Asp Ser Pro Ala
            770                 775                 780

Trp Ser Leu Ser Gly Arg Asp Glu Arg Glu Thr Val Ser Pro Pro Cys
785                 790                 795                 800

Phe Asp Glu Tyr Lys Met Ser Lys Glu Trp Thr Ala Ser Ser Ala Phe
                805                 810                 815

Ser Ser Val Cys Asn Gln Gln Pro Leu Asp Leu Ser Ser Gly Val Lys
            820                 825                 830

Gln Lys Ala Glu Gly Thr Gly Lys Thr Pro Val Gln Trp Glu Ser Val
            835                 840                 845

Leu Asp Leu Ser Val His Lys Lys His Cys Ser Asp Ser Glu Gly Lys
850                 855                 860

Glu Phe Lys Glu Ser His Ser Val Gln Pro Thr Cys Ser Ala Val Lys
865                 870                 875                 880

Lys Arg Lys Pro Thr Thr Cys Met Leu Gln Lys Val Leu Leu Asn Glu
                885                 890                 895

Tyr Asn Gly Ile Asp Leu Pro Val Glu Asn Pro Ala Asp Gly Thr Arg
            900                 905                 910

Ser Pro Ser Pro Cys Lys Ser Leu Glu Ala Gln Pro Asp Pro Asp Leu
            915                 920                 925

Gly Pro Gly Ser Gly Phe Pro Ala Pro Thr Val Glu Ser Thr Pro Asp
            930                 935                 940

Val Cys Pro Ser Ser Pro Ala Leu Gln Thr Pro Ser Leu Ser Ser Gly
945                 950                 955                 960

Gln Leu Pro Pro Leu Leu Ile Pro Thr Asp Pro Ser Pro Pro Pro
            965                 970                 975

Cys Pro Pro Val Leu Thr Val Ala Thr Pro Pro Pro Leu Leu Pro
            980                 985                 990

Thr Val Pro Leu Pro Ala Pro Ser Ser Ser Ala Ser Pro His Pro Cys
            995                 1000                1005

Pro Ser Pro Leu Ser Asn Ala Thr Ala Gln Ser Pro Leu Pro Ile Leu
            1010                1015                1020

Ser Pro Thr Val Ser Pro Ser Pro Ser Pro Ile Pro Pro Val Glu Pro
1025                1030                1035                1040

Leu Met Ser Ala Ala Ser Pro Gly Pro Pro Thr Leu Ser Ser Ser Ser
                1045                1050                1055

Ser Ser Ser Ser Ser Ser Ser Ser Phe Ser Ser Ser Ser Ser Ser Ser
            1060                1065                1070

Ser Pro Ser Pro Pro Pro Leu Ser Ala Ile Ser Ser Val Val Ser Ser
            1075                1080                1085

Gly Asp Asn Leu Glu Ala Ser Leu Pro Met Ile Ser Phe Lys Gln Glu
            1090                1095                1100

Glu Leu Glu Asn Glu Gly Leu Lys Pro Arg Glu Glu Pro Gln Ser Ala
1105                1110                1115                1120

Ala Glu Gln Asp Val Val Val Gln Glu Thr Phe Asn Lys Asn Phe Val
```

-continued

```
            1125               1130               1135

Cys Asn Val Cys Glu Ser Pro Phe Leu Ser Ile Lys Asp Leu Thr Lys
            1140               1145               1150

His Leu Ser Ile His Ala Glu Glu Trp Pro Phe Lys Cys Glu Phe Cys
            1155               1160               1165

Val Gln Leu Phe Lys Asp Lys Thr Asp Leu Ser Glu His Arg Phe Leu
    1170               1175               1180

Leu His Gly Val Gly Asn Ile Phe Val Cys Ser Val Cys Lys Lys Glu
1185               1190               1195               1200

Phe Ala Phe Leu Cys Asn Leu Gln Gln His Gln Arg Asp Leu His Pro
            1205               1210               1215

Asp Lys Val Cys Thr His His Glu Phe Glu Ser Gly Thr Leu Arg Pro
            1220               1225               1230

Gln Asn Phe Thr Asp Pro Ser Lys Ala His Val Glu His Met Gln Ser
            1235               1240               1245

Leu Pro Glu Asp Pro Leu Glu Thr Ser Lys Glu Glu Glu Leu Asn
    1250               1255               1260

Asp Ser Ser Glu Glu Leu Tyr Thr Thr Ile Lys Ile Met Ala Ser Gly
1265               1270               1275               1280

Ile Lys Thr Lys Asp Pro Asp Val Arg Leu Gly Leu Asn Gln His Tyr
            1285               1290               1295

Pro Ser Phe Lys Pro Pro Phe Gln Tyr His His Arg Asn Pro Met
            1300               1305               1310

Gly Ile Gly Val Thr Ala Thr Asn Phe Thr Thr His Asn Ile Pro Gln
            1315               1320               1325

Thr Phe Thr Thr Ala Ile Arg Cys Thr Lys Cys Gly Lys Gly Val Asp
            1330               1335               1340

Asn Met Pro Glu Leu His Lys His Ile Leu Ala Cys Ala Ser Ala Ser
1345               1350               1355               1360

Asp Lys Lys Arg Tyr Thr Pro Lys Lys Asn Pro Val Pro Leu Lys Gln
            1365               1370               1375

Thr Val Gln Pro Lys Asn Gly Val Val Val Leu Asp Asn Ser Gly Lys
            1380               1385               1390

Asn Ala Phe Arg Arg Met Gly Gln Pro Lys Arg Leu Asn Phe Ser Val
            1395               1400               1405

Glu Leu Ser Lys Met Ser Ser Asn Lys Leu Lys Leu Asn Ala Leu Lys
    1410               1415               1420

Lys Lys Asn Gln Leu Val Gln Lys Ala Ile Leu Gln Lys Asn Lys Ser
1425               1430               1435               1440

Ala Lys Gln Lys Ala Asp Leu Lys Asn Ala Cys Glu Ser Ser Ser His
            1445               1450               1455

Ile Cys Pro Tyr Cys Asn Arg Glu Phe Thr Tyr Ile Gly Ser Leu Asn
            1460               1465               1470

Lys His Ala Ala Phe Ser Cys Pro Lys Lys Pro Leu Ser Pro Pro Lys
            1475               1480               1485

Lys Lys Val Ser His Ser Ser Lys Lys Gly Gly His Ser Ser Pro Ala
            1490               1495               1500

Ser Ser Asp Lys Asn Ser Asn Ser Asn His Arg Arg Arg Thr Ala Asp
1505               1510               1515               1520

Ala Glu Ile Lys Met Gln Ser Met Gln Thr Pro Leu Gly Lys Thr Arg
            1525               1530               1535

Ala Arg Ser Ser Gly Pro Thr Gln Val Pro Leu Pro Ser Ser Ser Phe
            1540               1545               1550
```

```
Arg Ser Lys Gln Asn Val Lys Phe Ala Ala Ser Val Lys Ser Lys Lys
        1555                1560                1565

Pro Ser Ser Ser Leu Arg Asn Ser Ser Pro Ile Arg Met Ala Lys
    1570                1575                1580

Ile Thr His Val Glu Gly Lys Lys Pro Lys Ala Val Ala Lys Asn His
1585            1590                1595                1600

Ser Ala Gln Leu Ser Ser Lys Thr Ser Arg Ser Leu His Val Arg Val
                1605                1610                1615

Gln Lys Ser Lys Ala Val Leu Gln Ser Lys Ser Thr Leu Ala Ser Lys
            1620                1625                1630

Lys Arg Thr Asp Arg Phe Asn Ile Lys Ser Arg Glu Arg Ser Gly Gly
            1635                1640                1645

Pro Val Thr Arg Ser Leu Gln Leu Ala Ala Ala Ala Asp Leu Ser Glu
        1650                1655                1660

Asn Lys Arg Glu Asp Gly Ser Ala Lys Gln Leu Lys Asp Phe Ser
1665                1670                1675                1680

Tyr Ser Leu Arg Leu Ala Ser Arg Cys Ser Pro Pro Ala Ala Ser Tyr
                1685                1690                1695

Ile Thr Arg Gln Tyr Arg Lys Val Lys Ala Pro Ala Ala Ala Gln Phe
            1700                1705                1710

Gln Gly Pro Phe Phe Lys Glu
        1715
```

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:5:

```
Leu Xaa Cys Xaa Glu
1               5
```

(2) INFORMATION FOR SEQ ID NO:6:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:6:

```
Glu Ile Arg Cys Glu Glu Lys Pro Glu Asp Leu
1               5                   10
```

(2) INFORMATION FOR SEQ ID NO:7:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:7:

```
Lys Pro Glu Asp Leu Leu Glu Glu Pro Gln Ser
1               5                   10
```

(2) INFORMATION FOR SEQ ID NO:8:

(i) SEQUENCE CHARACTERISTICS:
        (A) LENGTH: 9 amino acids
        (B) TYPE: amino acid (D) TOPOLOGY: linear (xi) SEQUENCE DESCRIPTION: SEQ ID NO:8:

Glu Glu Glu Glu Tyr Met Pro Met Glu
    1               5

(2) INFORMATION FOR SEQ ID NO:9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:9:

AATCGATGAA GAAGAAGAAT ATATGCCTAT GGAACA                              36

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:10:

TTCCATAGGC ATATATTCTT CTTCTTCATC GATTTG                              36

(2) INFORMATION FOR SEQ ID NO:11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:11:

CCGGAGATCC GGGCTGAAGA AAAGCCA                                        27

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:12:

TTCACACCGG ATCCCCGGCT CTTTCGC                                        27

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:13:

TGGCTCTTCT AATAAGTC                                                  18

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear

```
    (ix) FEATURE:
          (A) NAME/KEY: Peptide
          (B) LOCATION: 15
          (D) OTHER INFORMATION: /note= "Xaa = (I/V)"

(xi) SEQUENCE DESCRIPTION: SEQ ID NO:14:

Gly Xaa Xaa Xaa Xaa Gly Lys Xaa Xaa Xaa Xaa Xaa Xaa Xaa Xaa
    1               5                   10                  15

(2) INFORMATION FOR SEQ ID NO:15:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (xi) SEQUENCE DESCRIPTION: SEQ ID NO:15:

TCTCCACAGC ACAGCCCT                                                   18

(2) INFORMATION FOR SEQ ID NO:16:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (xi) SEQUENCE DESCRIPTION: SEQ ID NO:16:

GGATAAGGAG GCTGTCTG                                                   18

(2) INFORMATION FOR SEQ ID NO:17:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (xi) SEQUENCE DESCRIPTION: SEQ ID NO:17:

GTGGTCCAAG AAACATTC                                                   18

(2) INFORMATION FOR SEQ ID NO:18:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (xi) SEQUENCE DESCRIPTION: SEQ ID NO:18:

TCGTGTAAAG CTCTTCAG                                                   18

(2) INFORMATION FOR SEQ ID NO:19:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (xi) SEQUENCE DESCRIPTION: SEQ ID NO:19:

GATACATTCC ACAGCCTG                                                   18

(2) INFORMATION FOR SEQ ID NO:20:
```

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:20:

Glu Asp Leu Leu Glu Glu
1               5

(2) INFORMATION FOR SEQ ID NO:21:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:21:

Glu Asp Leu Leu Asn Glu
1               5

(2) INFORMATION FOR SEQ ID NO:22:

(i) SEQUENCE CHARACTERISTICS:
        (A) LENGTH: 8 amino acids
        (B) TYPE: amino acid
        (D) TOPOLOGY: linear (ix) FEATURE:
        (A) NAME/KEY: Peptide
        (B) LOCATION: 8
        (D) OTHER INFORMATION: /note= "Xaa = S or T"

(xi) SEQUENCE DESCRIPTION: SEQ ID NO:22:

Gly Xaa Xaa Xaa Xaa Gly Lys Xaa
1               5

(2) INFORMATION FOR SEQ ID NO:23:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:23:

Asp Xaa Xaa Gly
1

(2) INFORMATION FOR SEQ ID NO:24:

(i) SEQUENCE CHARACTERISTICS:
        (A) LENGTH: 4 amino acids
        (B) TYPE: amino acid
        (D) TOPOLOGY: linear (ix) FEATURE:
        (A) NAME/KEY: Protein
        (B) LOCATION: 1
        (D) OTHER INFORMATION: /note= "Xaa = N or T"

(ix) FEATURE:
        (A) NAME/KEY: Protein
        (B) LOCATION: 2
        (D) OTHER INFORMATION: /note= "Xaa = K or Q"

(xi) SEQUENCE DESCRIPTION: SEQ ID NO:24:

Xaa Xaa Xaa Asp
1

(2) INFORMATION FOR SEQ ID NO:25:

(i) SEQUENCE CHARACTERISTICS:
            (A) LENGTH: 8 amino acids
            (B) TYPE: amino acid
            (D) TOPOLOGY: linear (xi) SEQUENCE DESCRIPTION: SEQ ID NO:25:

Gly Gly Thr Gly Thr Gly Ala Ala
    1               5

(2) INFORMATION FOR SEQ ID NO:26:

(i) SEQUENCE CHARACTERISTICS:
            (A) LENGTH: 6 amino acids
            (B) TYPE: amino acid
            (D) TOPOLOGY: linear (xi) SEQUENCE DESCRIPTION: SEQ ID NO:26:

Asp Leu Gly Ile Leu Thr
    1               5

(2) INFORMATION FOR SEQ ID NO:27:

(i) SEQUENCE CHARACTERISTICS:
            (A) LENGTH: 5 amino acids
            (B) TYPE: amino acid
            (D) TOPOLOGY: linear (xi) SEQUENCE DESCRIPTION: SEQ ID NO:27:

Asp Ser Leu Ile Thr
    1               5

(2) INFORMATION FOR SEQ ID NO:28:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:28:

Asp Val Arg Thr
    1

(2) INFORMATION FOR SEQ ID NO:29:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:29:

Asp Ala Phe Gly
    1

(2) INFORMATION FOR SEQ ID NO:30:

(i) SEQUENCE CHARACTERISTICS:
            (A) LENGTH: 4 amino acids
            (B) TYPE: amino acid
            (D) TOPOLOGY: linear (xi) SEQUENCE DESCRIPTION: SEQ ID NO:30:

Asp Leu Ser Gly
    1

(2) INFORMATION FOR SEQ ID NO:31:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:31:

Thr Ser Leu Asp
1

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:32:

Gly Asp Gly Ala Val Gly Lys Thr
1               5

(2) INFORMATION FOR SEQ ID NO:33:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:33:

Tyr Val Pro Thr
1

(2) INFORMATION FOR SEQ ID NO:34:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:34:

Asp Thr Ala Gly
1

(2) INFORMATION FOR SEQ ID NO:35:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:35:

Thr Gln Ile Asp
1

(2) INFORMATION FOR SEQ ID NO:36:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:36:

Gly Val Asn Gly Val Gly Lys Ser
1               5

(2) INFORMATION FOR SEQ ID NO:37:

(i) SEQUENCE CHARACTERISTICS:

```
        (A) LENGTH: 4 amino acids
        (B) TYPE: amino acid
        (D) TOPOLOGY: linear (xi) SEQUENCE DESCRIPTION: SEQ ID NO:37:

Thr Lys Phe Asp
1

(2) INFORMATION FOR SEQ ID NO:38:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:38:

Gly His Val Asp His Gly Lys Thr
1               5

(2) INFORMATION FOR SEQ ID NO:39:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:39:

Asp Xaa Xaa Xaa Xaa Xaa Xaa Xaa Xaa Xaa Xaa Thr
1               5                  10

(2) INFORMATION FOR SEQ ID NO:40:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:40:

Asp Cys Pro Gly
1

(2) INFORMATION FOR SEQ ID NO:41:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:41:

Asn Lys Cys Asp
1

(2) INFORMATION FOR SEQ ID NO:42:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:42:

Gly Ala Gly Gly Val Gly Lys Ser
1               5

(2) INFORMATION FOR SEQ ID NO:43:

(i) SEQUENCE CHARACTERISTICS:
        (A) LENGTH: 3 amino acids
```

```
              (B) TYPE: amino acid
              (D) TOPOLOGY: linear (xi) SEQUENCE DESCRIPTION: SEQ ID NO:43:

Asp Pro Thr
    1

(2) INFORMATION FOR SEQ ID NO:44:

(i) SEQUENCE CHARACTERISTICS:
              (A) LENGTH: 29 amino acids
              (B) TYPE: amino acid
              (D) TOPOLOGY: linear (xi) SEQUENCE DESCRIPTION: SEQ ID NO:44:

Thr Ala Pro Glu Asp Pro Asn Glu Glu Ala Val Ser Gln Ile Phe Pro
    1               5                  10                  15

Asp Ser Val Met Leu Ala Val Gln Glu Gly Ile Asp Leu
                20                  25

(2) INFORMATION FOR SEQ ID NO:45:

(i) SEQUENCE CHARACTERISTICS:
              (A) LENGTH: 29 amino acids
              (B) TYPE: amino acid
              (D) TOPOLOGY: linear (xi) SEQUENCE DESCRIPTION: SEQ ID NO:45:

Thr Ala Pro Glu Asp Pro Asn Glu Glu Ala Val Ser Gln Ile Phe Pro
    1               5                  10                  15

Asp Ser Val Met Leu Ala Val Gln Glu Gly Ile Asp Leu
                20                  25

(2) INFORMATION FOR SEQ ID NO:46:

(i) SEQUENCE CHARACTERISTICS:
              (A) LENGTH: 29 amino acids
              (B) TYPE: amino acid
              (D) TOPOLOGY: linear (xi) SEQUENCE DESCRIPTION: SEQ ID NO:46:

Asp Gly Pro Glu Asp Pro Asn Glu Gly Ala Val Asn Gly Phe Phe Thr
    1               5                  10                  15

Asp Ser Met Leu Leu Ala Ala Asp Glu Gly Leu Asp Ile
                20                  25

(2) INFORMATION FOR SEQ ID NO:47:

(i) SEQUENCE CHARACTERISTICS:
              (A) LENGTH: 29 amino acids
              (B) TYPE: amino acid
              (D) TOPOLOGY: linear (xi) SEQUENCE DESCRIPTION: SEQ ID NO:47:

Ser Ala Gly Glu Asp Asn Asn Glu Gln Ala Val Asn Glu Phe Phe Pro
    1               5                  10                  15

Glu Ser Leu Ile Leu Ala Ala Ser Glu Gly Leu Phe Leu
                20                  25

(2) INFORMATION FOR SEQ ID NO:48:

(i) SEQUENCE CHARACTERISTICS:
              (A) LENGTH: 29 amino acids
              (B) TYPE: amino acid
              (D) TOPOLOGY: linear
```

(xi) SEQUENCE DESCRIPTION: SEQ ID NO:48:

Thr Gly Gln Glu Asp Glu Asn Glu Ala Val Asp Gly Val Phe Ser
1               5                   10                  15

Asp Ala Met Leu Leu Ala Ala Glu Glu Gly Ile Glu Met
            20                  25

(2) INFORMATION FOR SEQ ID NO:49:

(i) SEQUENCE CHARACTERISTICS:
       (A) LENGTH: 30 amino acids
       (B) TYPE: amino acid
       (D) TOPOLOGY: linear (xi) SEQUENCE DESCRIPTION: SEQ ID NO:49:

Asp Gly Phe Glu Glu Asp Ala Asn Gln Glu Ala Val Asp Gly Met Phe
1               5                   10                  15

Pro Glu Arg Leu Leu Ser Glu Ala Glu Ser Ala Ala Glu Ser
            20                  25                  30

(2) INFORMATION FOR SEQ ID NO:50:

(i) SEQUENCE CHARACTERISTICS:
       (A) LENGTH: 50 amino acids
       (B) TYPE: amino acid
       (D) TOPOLOGY: linear (xi) SEQUENCE DESCRIPTION: SEQ ID NO:50:

Ala Lys Tyr Asp Phe Lys Ala Thr Ala Asp Asp Glu Leu Ser Phe Lys
1               5                   10                  15

Arg Gly Asp Ile Leu Lys Tyr Leu Asn Glu Glu Cys Asp Gln Asn Trp
            20                  25                  30

Tyr Lys Ala Glu Leu Asn Gly Lys Asp Gly Phe Ile Pro Lys Asn Tyr
        35                  40                  45

Ile Glu
    50

(2) INFORMATION FOR SEQ ID NO:51:

(i) SEQUENCE CHARACTERISTICS:
       (A) LENGTH: 49 amino acids
       (B) TYPE: amino acid
       (D) TOPOLOGY: linear (xi) SEQUENCE DESCRIPTION: SEQ ID NO:51:

Ala Leu Phe Asp Phe Asp Pro Gln Glu Asp Gly Glu Leu Gly Phe Arg
1               5                   10                  15

Arg Gly Asp Phe Ile His Val Met Asp Asn Ser Asp Pro Asn Trp Trp
            20                  25                  30

Lys Gly Ala Cys His Gly Gln Thr Gly Met Phe Pro Arg Asn Tyr Val
        35                  40                  45

Thr (2) INFORMATION FOR SEQ ID NO:52:

(i) SEQUENCE CHARACTERISTICS:
       (A) LENGTH: 66 amino acids
       (B) TYPE: amino acid
       (D) TOPOLOGY: linear (xi) SEQUENCE DESCRIPTION: SEQ ID NO:52:

Ala Leu Tyr Asp Tyr Lys Lys Glu Arg Glu Glu Asp Ile Asp Leu His

```
            1               5                  10                 15
    Leu Gly Asp Ile Leu Thr Val Asn Lys Gly Ser Leu Val Ala Leu Gly
                    20                  25                  30

Phe Ser Asp Gly Gln Glu Ala Arg Pro Glu Ile Gly Trp Leu Asn
            35                  40                  45

Gly Tyr Asn Glu Thr Thr Gly Glu Arg Gly Asp Phe Pro Gly Thr Tyr
        50                  55                  60

Val Glu
    65
```

(2) INFORMATION FOR SEQ ID NO:53:

(i) SEQUENCE CHARACTERISTICS:
        (A) LENGTH: 49 amino acids
        (B) TYPE: amino acid
        (D) TOPOLOGY: linear (xi) SEQUENCE DESCRIPTION: SEQ ID NO:53:

```
    Ala Leu Tyr Asp Phe Val Ala Ser Gly Asp Asn Thr Leu Ser Ile Thr
    1               5                  10                  15

Lys Gly Glu Lys Leu Arg Val Leu Tyr Asn His Asn Gly Glu Trp Cys
                    20                  25                  30

Glu Ala Gln Thr Lys Asn Gly Gln Gly Trp Val Pro Ser Asn Tyr Ile
            35                  40                  45

Thr
```

(2) INFORMATION FOR SEQ ID NO:54:

(i) SEQUENCE CHARACTERISTICS:
        (A) LENGTH: 51 amino acids
        (B) TYPE: amino acid
        (D) TOPOLOGY: linear (xi) SEQUENCE DESCRIPTION: SEQ ID NO:54:

```
    Ala Leu Tyr Asp Tyr Glu Ser Arg Thr Glu Thr Asp Leu Ala Phe Lys
    1               5                  10                  15

Lys Gly Glu Arg Leu Gln Ile Val Met Asn Thr Glu Gly Asp Trp Trp
                    20                  25                  30

Leu Ala His Ser Leu Thr Thr Gly Gln Thr Gly Tyr Ile Pro Ser Asn
            35                  40                  45

Tyr Val Ala
        50
```

(2) INFORMATION FOR SEQ ID NO:55:

(i) SEQUENCE CHARACTERISTICS:
        (A) LENGTH: 52 amino acids
        (B) TYPE: amino acid
        (D) TOPOLOGY: linear (xi) SEQUENCE DESCRIPTION: SEQ ID NO:55:

```
    Ala Ile Leu Pro Tyr Thr Lys Val Pro Asp Thr Asp Glu Ile Ser Phe
    1               5                  10                  15

Leu Lys Gly Asp Met Phe Ile Val His Asn Glu Leu Glu Asp Gly Trp
                    20                  25                  30

Met Trp Val Thr Asn Leu Arg Thr Asp Glu Gln Gly Leu Ile Val Glu
            35                  40                  45

Asp Leu Val Glu
        50
```

(2) INFORMATION FOR SEQ ID NO:56:

(i) SEQUENCE CHARACTERISTICS:
        (A) LENGTH: 50 amino acids
        (B) TYPE: amino acid
        (D) TOPOLOGY: linear (xi) SEQUENCE DESCRIPTION: SEQ ID NO:56:

```
Ala Leu Phe Asp Tyr Lys Ala Gln Arg Glu Asp Glu Leu Thr Phe Thr
1               5                   10                  15

Lys Ser Ala Ile Ile Gln Asn Val Glu Lys Gln Glu Gly Gly Trp Trp
            20                  25                  30

Arg Gly Asp Tyr Gly Gly Lys Lys Gln Leu Trp Phe Pro Ser Asn Tyr
        35                  40                  45

Val Glu
    50
```

(2) INFORMATION FOR SEQ ID NO:57:

(i) SEQUENCE CHARACTERISTICS:
        (A) LENGTH: 50 amino acids
        (B) TYPE: amino acid
        (D) TOPOLOGY: linear (xi) SEQUENCE DESCRIPTION: SEQ ID NO:57:

```
Ala Leu Phe Asp Phe Lys Gly Asn Asp Glu Asp Leu Pro Phe Lys
1               5                   10                  15

Lys Gly Asp Ile Leu Lys Ile Arg Asp Lys Pro Glu Glu Gln Trp Trp
            20                  25                  30

Asn Ala Glu Asp Met Asp Gly Lys Arg Gly Met Ile Pro Val Pro Tyr
        35                  40                  45

Val Glu
    50
```

(2) INFORMATION FOR SEQ ID NO:58:

(i) SEQUENCE CHARACTERISTICS:
        (A) LENGTH: 28 amino acids
        (B) TYPE: amino acid
        (D) TOPOLOGY: linear (xi) SEQUENCE DESCRIPTION: SEQ ID NO:58:

```
Ala Pro Pro Thr Pro Pro Pro Leu Pro Pro Leu Ile Pro Pro Pro
1               5                   10                  15

Pro Pro Leu Pro Pro Gly Leu Gly Pro Leu Pro Pro
            20                  25
```

(2) INFORMATION FOR SEQ ID NO:59:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO:59:

```
Ala Pro Thr Met Pro Pro Pro Leu Pro Pro Val Pro Pro Gln Pro Ala
1               5                   10                  15

Arg Arg Gln Ser Arg
            20
```

(2) INFORMATION FOR SEQ ID NO:60:

(i) SEQUENCE CHARACTERISTICS:
    (A) LENGTH: 40 amino acids
    (B) TYPE: amino acid
    (D) TOPOLOGY: linear (xi) SEQUENCE DESCRIPTION: SEQ ID NO:60:

Pro Pro Ala Tyr Pro Pro Pro Val Pro Val Pro Arg Lys Pro Ala
1               5                   10                  15

Phe Ser Asp Leu Pro Arg Ala His Ser Phe Thr Ser Lys Ser Pro Ser
            20                  25                  30

Pro Leu Leu Pro Pro Pro Pro Pro
            35              40

(2) INFORMATION FOR SEQ ID NO:61:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:61:

Pro Pro Ala Leu Pro Pro Pro Pro Arg Pro Val Pro
1               5                   10

(2) INFORMATION FOR SEQ ID NO:62:

(i) SEQUENCE CHARACTERISTICS:
        (A) LENGTH: 84 amino acids
        (B) TYPE: amino acid
        (D) TOPOLOGY: linear (xi) SEQUENCE DESCRIPTION: SEQ ID NO:62:

Cys Asn Val Cys Ala Lys Thr Phe Gly Gln Leu Ser Asn Leu Lys Val
1               5                   10                  15

His Leu Arg Val His Ser Gly Glu Arg Pro Phe Lys Cys Gln Thr Cys
            20                  25                  30

Asn Lys Gly Phe Thr Gln Leu Ala His Leu Gln Lys His Tyr Leu Val
            35                  40                  45

His Thr Gly Glu Lys Pro His Glu Cys Gln Val Cys His Lys Arg Phe
        50                  55                  60

Ser Ser Thr Ser Asn Leu Lys Thr His Leu Arg Leu His Ser Gly Glu
65                  70                  75                  80

Lys Pro Tyr Gln (2) INFORMATION FOR SEQ ID NO:63:

(i) SEQUENCE CHARACTERISTICS:
        (A) LENGTH: 80 amino acids
        (B) TYPE: amino acid
        (D) TOPOLOGY: linear (xi) SEQUENCE DESCRIPTION: SEQ ID NO:63:

Glu Val Ile Gly Val Met Ser Lys Glu Tyr Ile Pro Lys Gly Thr Arg
1               5                   10                  15

Phe Gly Pro Leu Ile Gly Glu Ile Tyr Thr Asn Asp Thr Val Pro Lys
            20                  25                  30

Asn Ala Asn Arg Lys Tyr Phe Trp Arg Ile Tyr Ser Arg Gly Glu Leu
            35                  40                  45

His His Phe Ile Asp Gly Phe Asn Glu Glu Lys Ser Asn Trp Met Arg
        50                  55                  60

Tyr Val Asn Pro Ala His Ser Pro Arg Glu Gln Asn Leu Ala Ala Cys

```
              65                  70                  75                  80
```

(2) INFORMATION FOR SEQ ID NO:64:

(i) SEQUENCE CHARACTERISTICS:
        (A) LENGTH: 30 amino acids
        (B) TYPE: amino acid
        (D) TOPOLOGY: linear (xi) SEQUENCE DESCRIPTION: SEQ ID NO:64:

```
Gln Asn Gly Met Asn Ile Tyr Phe Tyr Thr Ile Lys Pro Ile Pro Ala
1               5                   10                  15

Asn Gln Glu Leu Leu Val Trp Tyr Cys Arg Asp Phe Ala Glu
            20                  25                  30
```

(2) INFORMATION FOR SEQ ID NO:65:

(i) SEQUENCE CHARACTERISTICS:
        (A) LENGTH: 23 amino acids
        (B) TYPE: amino acid
        (D) TOPOLOGY: linear (xi) SEQUENCE DESCRIPTION: SEQ ID NO:65:

```
Val Glu Glu Ala Asp Met Pro Asn Glu Ser Ser Ala Lys Glu Pro Glu
1               5                   10                  15

Ile Arg Cys Glu Glu Lys Pro
            20
```

(2) INFORMATION FOR SEQ ID NO:66:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:66:

```
Leu Gly Pro Val Ser Met Pro Asn Leu Val Pro Glu Val Ile Asp Leu
1               5                   10                  15

Thr Cys His Glu Ala Gly
            20
```

(2) INFORMATION FOR SEQ ID NO:67:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:67:

```
Leu Gly Pro Val Ser Met Pro Asn Leu Val Pro Glu Val Ile Asp Leu
1               5                   10                  15

Thr Cys His Glu Ala Gly
            20
```

(2) INFORMATION FOR SEQ ID NO:68:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:68:

```
Leu Gly Ala Ala Glu Met Asp Leu Arg Cys Tyr Glu Glu Gly
1               5                   10
```

(2) INFORMATION FOR SEQ ID NO:69:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:69:

Leu His Pro Glu Asp Met Asp Leu Leu Cys Tyr Glu Met Gly
1              5                   10

(2) INFORMATION FOR SEQ ID NO:70:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:70:

Val Gly Gly Gly Glu Met Pro Glu Leu Gln Pro Glu Glu Glu Asp Leu
1              5                   10                15

Phe Cys Tyr Glu Asp Gly
              20

(2) INFORMATION FOR SEQ ID NO:71:

(i) SEQUENCE CHARACTERISTICS:
        (A) LENGTH: 18 amino acids
        (B) TYPE: amino acid
        (D) TOPOLOGY: linear (xi) SEQUENCE DESCRIPTION: SEQ ID NO:71:

Val Gly Glu Glu Leu Leu Pro Val Asp Leu Asp Leu Lys Cys Tyr Glu
1              5                   10                15

Asp Gly (2) INFORMATION FOR SEQ ID NO:72:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:72:

Glu Asp Leu Leu Glu Glu Pro Gln Ser
1              5

(2) INFORMATION FOR SEQ ID NO:73:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO:73:

Glu Asp Leu Leu Asn Glu Ser Gly Gln Pro
1              5                   10

(2) INFORMATION FOR SEQ ID NO:74:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:74:

```
        Glu Asp Leu Leu Asn Glu Pro Gly Gln
        1               5
```

(2) INFORMATION FOR SEQ ID NO:75:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:75:

```
        Glu Asp Leu Leu Glu Gly Gly Asp
        1               5
```

(2) INFORMATION FOR SEQ ID NO:76:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:76:

```
        Leu Asp Leu Ile Gln Glu Glu Glu Arg
        1               5
```

(2) INFORMATION FOR SEQ ID NO:77:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:77:

```
        His Asp Leu Ile Glu Glu Val Glu Gln
        1               5
```

(2) INFORMATION FOR SEQ ID NO:78:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO:78:

```
        Glu Asp Leu Leu Glu Glu Asp Pro Thr
        1               5
```

(2) INFORMATION FOR SEQ ID NO:79:

(i) SEQUENCE CHARACTERISTICS:
        (A) LENGTH: 50 amino acids
        (B) TYPE: amino acid
        (D) TOPOLOGY: linear (xi) SEQUENCE DESCRIPTION: SEQ ID NO:79:

```
        Ser Ala Pro Glu Gln Pro Ala Pro Leu Pro Glu Val Gly Asn Gln Asp
        1               5                   10                  15

Ala Val Pro Gln Val Ala Ile Pro Leu Pro Ala Cys Glu Pro Gln Pro
                        20                  25                  30

Glu Val Asp Gly Lys Gln Glu Val Thr Asp Cys Glu Val Asn Asp Val
                        35                  40                  45

Glu Glu
            50
```

(2) INFORMATION FOR SEQ ID NO:80:

(i) SEQUENCE CHARACTERISTICS:
        (A) LENGTH: 55 amino acids
        (B) TYPE: amino acid
        (D) TOPOLOGY: linear (xi) SEQUENCE DESCRIPTION: SEQ ID NO:80:

```
Ala Leu Arg Asp Phe Gly Lys Pro Asn Asp Gly Lys Ala Ala Trp Thr
 1               5                  10                  15

Asp Thr Val Leu Thr Ser Lys Lys Pro Lys Leu Glu Ser Arg Ser Asp
            20                  25                  30

Ser Pro Ala Trp Ser Leu Ser Gly Arg Asp Glu Pro Glu Thr Gly Ser
        35                  40                  45

Pro Pro Cys Phe Asp Glu Tyr
        50                  55
```

(2) INFORMATION FOR SEQ ID NO:81:

(i) SEQUENCE CHARACTERISTICS:
        (A) LENGTH: 92 amino acids
        (B) TYPE: amino acid
        (D) TOPOLOGY: linear (xi) SEQUENCE DESCRIPTION: SEQ ID NO:81:

```
Leu Pro Pro Leu Leu Thr Pro Thr Glu Pro Ser Ser Pro Pro Pro Cys
 1               5                  10                  15

Pro Pro Val Leu Thr Val Ala Thr Pro Pro Pro Leu Leu Pro Pro Thr
            20                  25                  30

Val Pro Leu Ser His Pro Ser Ser Asp Ala Ser Pro Gln Gln Cys Pro
        35                  40                  45

Ser Pro Phe Ser Asn Thr Thr Ala Gln Ser Pro Leu Pro Ile Leu Ser
        50                  55                  60

Pro Thr Val Ser Pro Ser Pro Ser Pro Ile Pro Pro Val Glu Pro Leu
65                  70                  75                  80

Met Ser Ala Ala Ser Pro Gly Pro Pro Thr Leu Ser
                85                  90
```

(2) INFORMATION FOR SEQ ID NO:82:

(i) SEQUENCE CHARACTERISTICS:
        (A) LENGTH: 86 amino acids
        (B) TYPE: amino acid
        (D) TOPOLOGY: linear (xi) SEQUENCE DESCRIPTION: SEQ ID NO:82:

```
Cys Asn Val Cys Glu Ser Pro Phe Leu Ser Ile Lys Asp Leu Thr Lys
 1               5                  10                  15

His Leu Ser Val His Ala Glu Glu Trp Pro Phe Lys Cys Glu Phe Cys
            20                  25                  30

Val Gln Leu Phe Lys Val Lys Thr Asp Leu Ser Glu His Arg Phe Leu
        35                  40                  45

Leu His Gly Val Gly Asn Ile Phe Val Cys Ser Val Cys Lys Lys Glu
        50                  55                  60

Phe Ala Phe Leu Cys Asn Leu Gln Gln His Gln Arg Asp Leu His Pro
65                  70                  75                  80

Asp Glu Val Cys Thr His
                85
```

(2) INFORMATION FOR SEQ ID NO:83:

(i) SEQUENCE CHARACTERISTICS:
    (A) LENGTH: 77 amino acids
    (B) TYPE: amino acid
    (D) TOPOLOGY: linear (xi) SEQUENCE DESCRIPTION: SEQ ID NO:83:

Thr Arg Ile Gly Val Trp Ala Thr Lys Pro Ile Leu Lys Gly Lys Lys
1               5                   10                  15

Phe Gly Pro Phe Val Gly Asp Lys Lys Arg Ser Gln Val Arg Asn
            20                  25                  30

Asn Val Tyr Met Trp Glu Val Tyr Tyr Pro Asn Leu Gly Trp Met Cys
            35                  40                  45

Ile Asp Ala Thr Asp Pro Glu Lys Gly Asn Trp Leu Arg Tyr Val Asn
50                      55                  60

Trp Ala Cys Ser Gly Glu Glu Gln Asn Leu Phe Pro Leu
65                  70                  75

(2) INFORMATION FOR SEQ ID NO:84:

(i) SEQUENCE CHARACTERISTICS:
       (A) LENGTH: 30 amino acids
       (B) TYPE: amino acid
       (D) TOPOLOGY: linear (xi) SEQUENCE DESCRIPTION: SEQ ID NO:84:

Glu Ile Asn Arg Ala Ile Tyr Tyr Lys Thr Leu Lys Pro Ile Ala Pro
1               5                   10                  15

Gly Glu Glu Leu Leu Val Trp Tyr Asn Gly Glu Asp Asn Pro
            20                  25                  30

(2) INFORMATION FOR SEQ ID NO:85:

(i) SEQUENCE CHARACTERISTICS:
       (A) LENGTH: 8 amino acids
       (B) TYPE: amino acid
       (D) TOPOLOGY: linear (xi) SEQUENCE DESCRIPTION: SEQ ID NO:85:

Gly Lys Pro Asn Asp Gly Lys Ala
1               5

(2) INFORMATION FOR SEQ ID NO:86:

(i) SEQUENCE CHARACTERISTICS:
       (A) LENGTH: 5 amino acids
       (B) TYPE: amino acid
       (D) TOPOLOGY: linear (xi) SEQUENCE DESCRIPTION: SEQ ID NO:86:

Asp Glu Arg Glu Thr
1               5

(2) INFORMATION FOR SEQ ID NO:87:

(i) SEQUENCE CHARACTERISTICS:
       (A) LENGTH: 14 amino acids
       (B) TYPE: amino acid
       (D) TOPOLOGY: linear (xi) SEQUENCE DESCRIPTION: SEQ ID NO:87:

Asp Xaa Xaa Xaa Xaa Xaa Xaa Xaa Xaa Xaa Xaa Xaa Xaa Thr
1               5                   10

(2) INFORMATION FOR SEQ ID NO:88:

(i) SEQUENCE CHARACTERISTICS:
        (A) LENGTH: 13 amino acids
        (B) TYPE: amino acid
        (D) TOPOLOGY: linear (xi) SEQUENCE DESCRIPTION: SEQ ID NO:88:

Asp Xaa Xaa Xaa Xaa Xaa Xaa Xaa Xaa Xaa Xaa Xaa Thr
    1               5                   10

(2) INFORMATION FOR SEQ ID NO:89:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:89:

Asp Ser Glu Gly
    1

(2) INFORMATION FOR SEQ ID NO:90:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:90:

Thr Gln Pro Asp
    1

(2) INFORMATION FOR SEQ ID NO:91:

(i) SEQUENCE CHARACTERISTICS:
        (A) LENGTH: 11 amino acids
        (B) TYPE: amino acid
        (D) TOPOLOGY: linear (xi) SEQUENCE DESCRIPTION: SEQ ID NO:91:

Glu Ile Arg Cys Asp Glu Lys Pro Glu Asp Leu
    1               5                   10

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:92:

CCAGAACCAG ACGAGCGATT                                          20

(2) INFORMATION FOR SEQ ID NO:93:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:93:

AGTTCTGGGG ATTTGCATG                                           19

(2) INFORMATION FOR SEQ ID NO:94:

(i) SEQUENCE CHARACTERISTICS:
        (A) LENGTH: 121 base pairs
        (B) TYPE: nucleic acid
        (C) STRANDEDNESS: double
        (D) TOPOLOGY: linear (xi) SEQUENCE DESCRIPTION: SEQ ID NO:94:

GAATTCCCGG CTCACTGAAG CTTGGCACGT GCGCTCTGGA ATATCTGAAT GATCTCAGTA            60

CAATGAAGGA GTGCCTTTTC CCTTTCTACC CTGCCTCCTT GAAGCATGCA TTAGAGTCGT           120

T                                                                          121

(2) INFORMATION FOR SEQ ID NO:95:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:95:

GGAGTGGGGG CCAGTCACCC GGAGCCTTCA GCGCAGCACC AAGCAGGAGC TGAAGGACTT            60

GCAG                                                                        64

(2) INFORMATION FOR SEQ ID NO:96:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:96:

GGGGCCGGCG AAACAGCGGC GGCGGCGGCG GCCCTCGGTG CTCTGAGGCT GGGCCGGCGG            60

GCGCGG                                                                      66

(2) INFORMATION FOR SEQ ID NO:97:

(i) SEQUENCE CHARACTERISTICS:
        (A) LENGTH: 474 base pairs
        (B) TYPE: nucleic acid
        (C) STRANDEDNESS: single
        (D) TOPOLOGY: linear (xi) SEQUENCE DESCRIPTION: SEQ ID NO:97:

CCTACAGCTA CCCTCACAAG CATGAAGTGC TGTGGCTGTT CCTTATCCTA ATGATGCGCT            60

TTTGTCCCGT AAATGTTAAC ACTCATGAAG CATACCCCGG CCTCTCAGTT CTTGAGGGCC           120

TCCCCACCGC AGCAGCAAGG AAAGCTCACG AACCCCAAAC CTGGCAAGTC ACCTGCAGCC           180

CATGGTGAGC TCTGGGAAGT GTGGTTGAGC CCTTGGGGTC ACTCCTTTTT TGCATGTGCA           240

AATGTGCTGG TCACCCTTCA ACGCTCCCAG ACGGTCAGGA AAACTGTTCC AATCATGAAA           300

AGGGGGGATG ATTTTGTAAA GTGGCATTTC CTGGTCAGTG GTGGTCTTCA AGACGACAGC           360

TCTGTATCTG CCATGTGAAG AGAATTAACA ATAAAAGTGT GAAGAGCGAA AAAAAAAAA            420

AAAAAAAAAA AAAAAAAAAA AAAAAAAAAA AAAAAAAAAA AAAGCGCCGG CCGC                 474

(2) INFORMATION FOR SEQ ID NO:98:

(i) SEQUENCE CHARACTERISTICS:
        (A) LENGTH: 118 amino acids
        (B) TYPE: amino acid
        (D) TOPOLOGY: linear (xi) SEQUENCE DESCRIPTION: SEQ ID NO:98:

Asn Ser Glu Glu Val Ile Gly Val Met Ser Lys Glu Tyr Ile Pro Lys
1               5                   10                  15

Gly Thr Arg Phe Gly Pro Leu Ile Gly Glu Ile Tyr Thr Asn Asp Thr
            20                  25                  30

Val Pro Lys Asn Ala Asn Arg Lys Tyr Phe Trp Arg Ile Tyr Ser Arg
        35                  40                  45

Gly Glu Leu His His Phe Ile Asp Gly Phe Asn Glu Glu Lys Ser Asn
        50                  55                  60

Trp Met Arg Tyr Val Asn Pro Ala His Ser Pro Arg Glu Gln Asn Leu
65                  70                  75                  80

Ala Ala Cys Gln Asn Gly Met Asn Ile Tyr Phe Tyr Thr Ile Lys Pro
            85                  90                  95

Ile Pro Ala Asn Gln Glu Leu Leu Val Trp Tyr Cys Arg Asp Phe Ala
            100                 105                 110

Glu Arg Leu His Tyr Pro
            115

(2) INFORMATION FOR SEQ ID NO:99:

(i) SEQUENCE CHARACTERISTICS:
        (A) LENGTH: 116 amino acids
        (B) TYPE: amino acid
        (D) TOPOLOGY: linear (xi) SEQUENCE DESCRIPTION: SEQ ID NO:99:

Val Asp Lys Thr Arg Ile Gly Val Trp Ala Thr Lys Pro Ile Leu Lys
1               5                   10                  15

Gly Lys Lys Phe Gly Pro Phe Val Gly Asp Lys Lys Arg Ser Gln
            20                  25                  30

Val Lys Asn Asn Val Tyr Met Trp Glu Val Tyr Tyr Pro Asn Leu Gly
            35                  40                  45

Trp Met Cys Ile Asp Ala Thr Asp Pro Glu Lys Gly Asn Trp Leu Arg
        50                  55                  60

Tyr Val Asn Trp Ala Cys Ser Gly Glu Glu Gln Asn Leu Phe Pro Leu
65                  70                  75                  80

Glu Ile Asn Arg Ala Ile Tyr Tyr Lys Thr Leu Lys Pro Ile Ala Pro
            85                  90                  95

Gly Glu Glu Leu Leu Val Trp Tyr Asn Gly Glu Asp Asn Pro Glu Ile
            100                 105                 110

Ala Ala Ala Ile
            115

(2) INFORMATION FOR SEQ ID NO:100:

(i) SEQUENCE CHARACTERISTICS:
        (A) LENGTH: 115 amino acids
        (B) TYPE: amino acid
        (D) TOPOLOGY: linear (xi) SEQUENCE DESCRIPTION: SEQ ID NO:100:

Met Pro Gly Ala Gly Leu Gly Ile Trp Thr Lys Arg Lys Ile Glu Val
1               5                   10                  15

Gly Glu Lys Phe Gly Pro Tyr Val Gly Glu Gln Arg Ser Asn Leu Lys
            20                  25                  30

Asp Pro Ser Tyr Gly Trp Glu Ile Leu Asp Glu Phe Tyr Asn Val Lys
            35                  40                  45

```
    Phe Cys Ile Asp Ala Ser Gln Pro Asp Val Gly Ser Trp Leu Lys Tyr
         50                  55                  60

Ile Arg Phe Ala Gly Cys Tyr Asp Gln His Asn Leu Val Ala Cys Gln
    65                  70                  75                  80

Ile Asn Asp Gln Ile Phe Tyr Arg Val Val Ala Asp Ile Ala Pro Gly
                         85                  90                  95

Glu Glu Leu Leu Leu Phe Met Lys Ser Glu Asp Tyr Pro His Glu Thr
                    100                 105                 110

Met Ala Pro
            115

(2) INFORMATION FOR SEQ ID NO:101:

(i) SEQUENCE CHARACTERISTICS:
        (A) LENGTH: 110 amino acids
        (B) TYPE: amino acid
        (D) TOPOLOGY: linear (xi) SEQUENCE DESCRIPTION: SEQ ID NO:101:

Asp Glu Leu His Gly Asn Val Leu Ile Ala Val Thr Gln Ile Ala Leu
    1               5                  10                  15

Gly Arg Thr Ile Gly Val Ile Asp Lys Ala Thr Pro Asn Asp Ser Asn
                    20                  25                  30

Ala Leu Leu Ile Leu Asn Leu Ile Lys Glu Ala Asp Asp Gly Glu Asp
                35                  40                  45

Ala Asn Ile Cys Met Arg Gln Glu Asp Arg Lys Thr Phe Leu Gln Thr
            50                  55                  60

Ser Lys Ile Ile Asn Ile Gly Glu Arg Leu Leu Leu Gln Arg Leu Ser
    65                  70                  75                  80

Glu Glu Glu Cys Asp Glu Glu Asp Gln Asp Asp Leu Glu Asn Leu Ile
                    85                  90                  95

Leu Leu Lys Asp Glu Asp Arg Pro Asp Ser Thr Gln Ser Cys
                    100                 105                 110

(2) INFORMATION FOR SEQ ID NO:102:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO:102:

Glu Trp Gly Pro Val Thr Arg Ser Leu Gln Arg Ser Thr Lys Gln Glu
    1               5                  10                  15

Leu Lys Asp Leu Gln
                    20

(2) INFORMATION FOR SEQ ID NO:103:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO:103:

Gly Ala Glu Glu Thr Ala Ala Ala Ala Ala Leu Gly Ala Leu Arg
    1               5                  10                  15

Leu Gly Arg Arg Ala Arg
                    20
```

(2) INFORMATION FOR SEQ ID NO:104:

(i) SEQUENCE CHARACTERISTICS:
        (A) LENGTH: 391 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..391

(xi) SEQUENCE DESCRIPTION: SEQ ID NO:104:

```
GTG TAC TAC CCA AAT TTG GGG TGG ATG TGC ATT GAT GCC ACT GAT CCG       48
Val Tyr Tyr Pro Asn Leu Gly Trp Met Cys Ile Asp Ala Thr Asp Pro
 1               5                  10                  15

GAG AAG GGC AAC TGG CTC CGC TAT GTG AAC TGG GCT TGC TCA GGA GAA       96
Glu Lys Gly Asn Trp Leu Arg Tyr Val Asn Trp Ala Cys Ser Gly Glu
                20                  25                  30

GAA CAG AAT TTA TTT CCA CTG GAA ATC AAC AGA GCC ATT TAC TAT AAA      144
Glu Gln Asn Leu Phe Pro Leu Glu Ile Asn Arg Ala Ile Tyr Tyr Lys
            35                  40                  45

ACC TTA AAG CCA ATC GCG CCT GGC GAG GAG CTC CTG GTC TGG TAC AAT      192
Thr Leu Lys Pro Ile Ala Pro Gly Glu Glu Leu Leu Val Trp Tyr Asn
         50                  55                  60

GGG GAA GAC AAC CCC GAG ATA GCA GCT GCG ATT GAG GAA GAG CGA GCC      240
Gly Glu Asp Asn Pro Glu Ile Ala Ala Ala Ile Glu Glu Glu Arg Ala
 65                  70                  75                  80

AGC GCC CGG AGC AAG CGG AGC TCC CCG AAG AGC CGG AGA GGG AAG AAG      288
Ser Ala Arg Ser Lys Arg Ser Ser Pro Lys Ser Arg Arg Gly Lys Lys
                 85                  90                  95

AAA TCA CAG GAG AAT AAA AAC AAA GGC ATC AGA ACC CAG GCT GCA GCG      336
Lys Ser Gln Glu Asn Lys Asn Lys Gly Ile Arg Thr Gln Ala Ala Ala
                100                 105                 110

CGG AAG GCG AGC GAG CTG GAC TCC ACC TCT GCA AAC ATG AGG GGC TCT      384
Arg Lys Ala Ser Glu Leu Asp Ser Thr Ser Ala Asn Met Arg Gly Ser
            115                 120                 125

GCA GAA G                                                            391
Ala Glu
    130
```

(2) INFORMATION FOR SEQ ID NO:105:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO:105:

```
Val Tyr Tyr Pro Asn Leu Gly Trp Met Cys Ile Asp Ala Thr Asp Pro
 1               5                  10                  15

Glu Lys Gly Asn Trp Leu Arg Tyr Val Asn Trp Ala Cys Ser Gly Glu
                20                  25                  30

Glu Gln Asn Leu Phe Pro Leu Glu Ile Asn Arg Ala Ile Tyr Tyr Lys
            35                  40                  45

Thr Leu Lys Pro Ile Ala Pro Gly Glu Glu Leu Leu Val Trp Tyr Asn
         50                  55                  60

Gly Glu Asp Asn Pro Glu Ile Ala Ala Ala Ile Glu Glu Glu Arg Ala
 65                  70                  75                  80

Ser Ala Arg Ser Lys Arg Ser Ser Pro Lys Ser Arg Arg Gly Lys Lys
```

```
                          85                      90                      95
Lys Ser Gln Glu Asn Lys Asn Lys Gly Ile Arg Thr Gln Ala Ala Ala
                100                 105                 110
Arg Lys Ala Ser Glu Leu Asp Ser Thr Ser Ala Asn Met Arg Gly Ser
        115                 120                 125

Ala Glu
    130

(2) INFORMATION FOR SEQ ID NO:106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:106:

GCGAGGAGCT CCTGGTCTGG                                                      20
```